United States Patent
Bushkin et al.

(10) Patent No.: US 10,900,072 B2
(45) Date of Patent: Jan. 26, 2021

(54) RAPID ASSAYS FOR T-CELL ACTIVATION BY RNA MEASUREMENTS USING FLOW CYTOMETRY

(71) Applicant: Rutgers, The State University of New Jersey, New Brunswick, NJ (US)

(72) Inventors: Yuri Bushkin, Hudson, NY (US); Maria L. Gennaro, New York, NY (US); Sanjay Tyagi, New York, NY (US); Richard Pine, Pelham, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 438 days.

(21) Appl. No.: 14/411,224

(22) PCT Filed: Jun. 26, 2013

(86) PCT No.: PCT/US2013/047774
§ 371 (c)(1),
(2) Date: Dec. 24, 2014

(87) PCT Pub. No.: WO2014/004609
PCT Pub. Date: Jan. 3, 2014

(65) Prior Publication Data
US 2016/0201122 A1    Jul. 14, 2016

Related U.S. Application Data

(60) Provisional application No. 61/665,231, filed on Jun. 27, 2012, provisional application No. 61/784,802, filed on Mar. 14, 2013.

(51) Int. Cl.
*C12Q 1/6841* (2018.01)
(52) U.S. Cl.
CPC ................... *C12Q 1/6841* (2013.01)
(58) Field of Classification Search
None
See application file for complete search history.

(56) References Cited

U.S. PATENT DOCUMENTS

| | | | |
|---|---|---|---|
| 4,994,369 A * | 2/1991 | Krensky | C07K 14/47 435/6.1 |
| 7,514,232 B2 | 4/2009 | Maino et al. | |
| 7,709,198 B2 | 5/2010 | Luo et al. | |
| 7,879,609 B2 | 2/2011 | Morin et al. | |
| 8,604,182 B2 | 12/2013 | Luo et al. | |
| 2009/0081688 A1 | 3/2009 | Luo et al. | |
| 2010/0068814 A1* | 3/2010 | Zhu | C12N 15/111 435/455 |
| 2012/0171161 A1* | 7/2012 | Abramson | A61K 35/16 424/93.3 |
| 2013/0052642 A1* | 2/2013 | Nogueira Ivarez | C12N 5/0637 435/6.11 |
| 2015/0018226 A1* | 1/2015 | Hansen | G01N 1/34 506/9 |

FOREIGN PATENT DOCUMENTS

| | | |
|---|---|---|
| EA | 013466 B1 | 4/2010 |
| EP | 2186827 A1 | 5/2010 |
| JP | 2005524395 A | 8/2005 |
| JP | 2008539705 A | 11/2008 |
| JP | 2010004750 A | 1/2010 |
| RU | 2258710 C2 | 8/2005 |
| WO | 2000053761 A2 | 9/2000 |
| WO | 2003/089903 A2 | 10/2003 |
| WO | 2005118788 A2 | 12/2005 |
| WO | 2006/117327 A2 | 11/2006 |
| WO | 2007001986 A2 | 1/2007 |
| WO | 2007002006 A2 | 1/2007 |
| WO | 2007028573 A1 | 3/2007 |
| WO | 2012/037937 A2 | 3/2012 |

OTHER PUBLICATIONS

Hess et al. (Leukemia 2004 vol. 18 p. 1981-1988) (Year: 2004).*
Caserta et al., "Synthetic CD4(sup)(+) T Cell-Targeted Antigen-Presenting Cells Elicit Protective Antitumor Responses," Cancer Research (Apr. 15, 2008) 68:3010-3018.
Butler et al., "Ex Vivo Expansion of Human CD8(sup)(+) T Cells Using Autologous CD4 (sup)(+) T Cell Help," PLoS one (Jan. 12, 2012): 7(a30229):1-11.
Lorenzi et al., "Intranasal Vaccination With Messenger RNA as a new Approach in Gene Therapy: Use Against Tuberculosis," BMC Biotechnology (Oct. 20, 2010) 10:1-11.
Hanley et al., "Detection of Low Abundance RNA Molecules in Individual Cells by Flow Cytometry," PLOS ONE (Feb. 2013); 8(2):e57002 (8 pages).
Raj et al., "Imaging individual mRNA molecules using multiple singly labeled probes," Nature Methods (Oct. 2008); 5(10):877-879.
Pennline et al., "Detection of In Vivo-Induced IL-1 mRNA in Murine Cells by Flow Cytometry (FC) and Fluorescent In Situ Hybridization (FISH)," Lymphokine and Cyotkine Research (1992); 11(1):65-71.
Liu & Heckman, "The Sevenfold Way of PKC Regulation," Cell. Signal., (1998) 10(8):529-542.

\* cited by examiner

*Primary Examiner* — Katherine D Salmon
(74) *Attorney, Agent, or Firm* — Fox Rothschild LLP

(57) ABSTRACT

The present invention relates to a method for rapidly detecting copies of at least one RNA molecule expressed in individual cells and uses thereof.

30 Claims, 11 Drawing Sheets

Specification includes a Sequence Listing.

RAPID ASSAYS FOR T-CELL ACTIVATION BY RNA MEASUREMENTS USING FLOW CYTOMETRY

CROSS REFERENCE TO RELATED APPLICATIONS

This application is a U.S. National Phase of International Application No. PCT/US2013/047774, filed Jun. 26, 2013, which claims priority of U.S. Provisional Application No. 61/665,231 filed Jun. 27, 2012 and U.S. Provisional Application No. 61/784,802 filed Mar. 14, 2013. The contents of the applications are incorporated herein by reference in their entirety.

GOVERNMENT INTERESTS

The invention disclosed herein was made at least in part with Government support under Grant Nos. AI045761, AI106036, MH079197, and HL106788 from the National Institutes of Health. The United States government has certain rights in the invention.

FIELD OF THE INVENTION

This invention relates to methods that rapidly detect gene expression in individual cells.

BACKGROUND

Many pathological conditions provoke T cell-mediated immune responses. These include cancer, autoimmunity, transplantation, and infectious diseases, including, for example, tuberculosis (TB). In all these conditions, activation of T cells involving interaction of a T cell receptor (TCR) with a specific antigen (Ag) as a common denominator, while the functional consequences of this interaction vary. In any given T cell, the TCR signaling cascade may stimulate expression of different sets of genes depending on the physical nature of the Ag, its presentation, the TCR repertoire, and the strength of Ag-induced activation. These induced differences in gene expression patterns during cell activation, proliferation and differentiation may ultimately contribute to functional heterogeneity among the clonally expanded effector cells. An additional element of cell-to-cell diversity arises during T-cell homeostasis. When the Ag is cleared, most expanded effector cells die by apoptosis, while a small fraction of cells survive as long-lived memory cells. The responses that occur upon re-exposure to Ag are governed by the factors listed above, and are further influenced by the prior differentiation process. As a result, for each Ag encountered, the immune response generates functionally distinct subsets of T cells (for example, effector vs. central memory vs. effector memory cells) sharing the same Ag specificity. At any given time in the natural history of an immunopathological condition, the relative representation of these different subsets varies; they may determine or reflect the disease process. T-cell subsets correlate with Ag and pathogen load in vivo and, as exemplified by studies of chronic viral infections and TB, quantitative analysis of these key subsets is promising for diagnostics and measurements of protective immunity. Tell-tale changes in T cell subsets should also be seen during treatment, since treatment outcome is associated with a particular evolution of the immunopathological condition. Such signatures of evolving states (natural or treatment-mediated) escape ensemble measurements and can only be detected at the single T cell level. The properties of individual T cells are only fully revealed by their response to Ag stimulation.

Current, blood-based clinical immunoassays can typically recognize the presence of non-infectious and infectious pathology, but may not reveal progression of the pathology. In contrast, single-cell, functional analysis of Ag-specific immune cells in peripheral blood should unravel multiple, intersecting immunopathological states associated with evolution of infection and disease. Such analysis would help advance prognostic capability and foster effective intervention. A compelling example is provided by infection with *Mycobacterium tuberculosis*. With current methods, TB is typically diagnosed after the diseased subject has already transmitted infection to his/her contacts. Yet diagnosis of asymptomatic infection per se does not warrant medical intervention. The ability to distinguish stable latent infection (LTBI) from early active disease (before it is contagious) is greatly needed. Existing immunodiagnostic assays fail to address this need, as they are not geared to distinguish between Ag-specific, functional T cell subsets known to differ between infection states. Moreover, these assays do not assess responses that may reflect stage-specific expression of mycobacterial Ags.

The hallmark of *M. tuberculosis* infection is the huge number of people infected asymptomatically with this pathogen (2 billion). In the absence of immunocompromise, 90-95% of latently infected individuals will not develop active TB. However, given the size of the reservoir, *M. tuberculosis* infection still causes 9.4 million new cases of active TB and 1.7 million deaths per year. Transmission of infection would be greatly reduced if it were possible to identify and treat infected individuals as they progress to active disease before they become symptomatic and infectious. Detecting tubercle bacilli or bacillary products is exceedingly difficult during early active disease, due to very low bacillary numbers. The standard, microbiological diagnosis of active TB detects individuals who already bear tubercle bacilli in their respiratory secretion and are therefore infectious.

Methods based on ensemble measurements are simply not geared to revealing the complexity of the cell-mediated immune response and cannot reveal rare or transient cell states associated with disease stage and evolution. The most common immunoassay formats for single T cell analysis are the enzyme-linked immunospot assay (ELISPOT) method and quantitative flow cytometric (FC) analysis. In a commercial ELISPOT test from Oxford Immunotech (United Kingdom), peripheral blood mononuclear cells (PBMCs) are first isolated from a blood sample, washed and counted. Then a predetermined number (such as 250,000) of PBMCs and *M. tuberculosis*-specific Ags are added to plate wells pre-coated with antibodies to interferon gamma (IFNγ) and incubated overnight (16-20 hours). IFNγ released from activated T cells is captured in the wells. This is followed by incubation with a second antibody (Ab) conjugated to a color-forming enzyme, after which the wells are washed and a color-forming substrate is added. Spots are produced where IFNγ was secreted by T cells giving a characteristic appearance of a colored ring surrounding the cytokine-releasing cell. Finally, spots are counted, either by naked eye or using a plate reader. ELISPOT is highly sensitive (its detection limit is $10/10^6$ in PBMCs). However, it fails to provide the desired discrimination among functional T cell subsets for several reasons. First, it is not typically amenable to simultaneous detection of several targets. Second, the format limits the number of cells for analysis (e.g., 250,000 cells per well in the commercial T-SPOT.TB test mentioned above). Conventional FC has multi-parameter capability. Cells in whole blood or PBMCs are stimulated by incubation for 6 hours or more with specific Ags, for example *M tuberculosis*-specific peptides or proteins, and extracellular secretion inhibitor such as brefeldin or monensin. Permeabilized T cells are then stained with fluorophor-labeled anti-cytokine Ab (for example, FITC-conjugated anti-IFNγ) and analyzed by FC. Staining of proteins with Ab reduces the versatility of conventional FC, particularly in the case of intracellular proteins. Moreover, assays are limited by protocols that require prolonged stimulation of T cells by endogenous antigen presenting cells (APCs), which increases turn-around time and reduces clinical usefulness.

The existing methods for cytokine analysis of individual cells lack the ability to rapidly identify low-frequency T cell populations present in small samples of peripheral blood. The commercial ELISPOT test does not distinguish between TB and LTBI. Moreover, a positive result in an asymptomatic individual (in the absence of microbiological evidence of active TB) is uninformative for reactivation risk. Thus, while accurately reflecting the presence of *M. tuberculosis* infection, a positive result is not considered an indication for therapeutic intervention. This diminishes the acceptability of the test, particularly in low-resource, high-burden countries, where most of the population is infected (up to 80% in regions of South Africa). Moreover, even in low burden, high-resource countries such as the US, the side effects of LTBI treatment often lead to its refusal when it is recommended without an indication of reactivation risk. Clearly, the limitations of current immunodiagnostics have enormous public health consequences worldwide.

Thus, there is an unmet need for methods that rapidly detect gene expression in individual cells.

SUMMARY

This invention relates to novel rapid methods for detecting various RNA molecules in individual cells.

Accordingly, one aspect of this invention provides a method for detecting copies of at least one RNA molecule expressed in individual cells. The method includes (a) providing a sample containing a population of cells (e.g., at least 100 or at least 10,000 cells) that express specific receptors capable of initiating signal cascades leading to gene expression upon binding to them of ligands or stimulating molecules; (b) inducing gene expression in the cells ex vivo, either immediately or after culturing, by incubating the cells with at least one compound, for example, a peptide or mixture of peptides derived from a microorganism (such as *M. tuberculosis*) that will bind specific receptors or otherwise initiate signaling and initiate gene expression; (c) fixing and permeabilizing the cells; (d) labeling copies of at least one RNA molecule expressed by the cells with a set of fluorescently labeled oligonucleotide hybridization probes, and washing away unbound probes; and (e) detecting cells having expression events by flow cytometry (FC), an expression event being one or more fluorescence measurements categorized by fluorescence intensity gating.

The aforementioned method can be used for detecting various RNA molecules in individual cells. In particular, it can be used for detecting RNA molecules encoded by cytokine genes, such as IL-2, TNFα, or IFNγ.

In the method, the step of inducing can include stimulating T-cell receptor (TCR) signaling and down-stream gene expression by antigen presenting cells (APCs) that are present in the cell population or by artificial APC (aAPC). The induction can be carried out for a period of from 30 minutes to 6 hours. In either case, the step of inducing can also include co-stimulating with at least one monoclonal antibody (mAb). The monoclonal antibody can be bound to or added to the aAPC or APCs.

In one embodiment of the method, the cell population can be a population of T cells obtained from human PBMCs. In that case, the at least one RNA molecule can be one encoded by a cytokine gene. And, cells in the cell population can be induced by APCs or aAPCs with one or more peptide-loaded MHC molecules that interact with TCR.

In the method, the compound or stimulatory molecules can be derived from a microorganism, such as *M. tuberculosis*-derived immunogenic peptides. In one example, the compound can contain a peptide or mixture of peptides, such as those that associate with MHC class I or MHC class II molecules. These peptide or mixture of peptides can be added to the APC or aAPC mentioned above at various concentrations, e.g., between 1-20 μg/ml.

In the above-described method, the step of inducing can include stimulating toll-like receptor signaling and down-stream gene expression in a cell containing such receptors with a stimulus, examples of which include cytokines, microbial products or synthetic compounds. Examples of the microbial product include a lipid, glycan, glycolipid, sulfolipid, glycoprotein, protein, peptide, or nucleic acid (e.g., RNA or DNA). The stimulation can be carried out for a period of from 30 minutes to 72 hours (e.g., 30 minutes to 6 hours, 6 hours to 24 hours, 24 hours to 72 hours). The stimulus can be present at a concentration between 1-20 μg/ml (e.g., 1-100 ng/ml or 100-1000 ng/ml). The compound or stimulus can be a cytokine, such as IFNγ, IL-2, IL-15, TNFα, or a cytokine other than IFNγ, IL-2, IL-15, or TNFα. In the method, more than one compound or stimulus can be provided either at the same time or at different times.

In step (d) of the method, the probe set can include 20-60 probes, each singly labeled with the same fluorescent moiety.

In another embodiment, the detected cells having expression events can be separated (e.g., by fluorescence-activated cell sorting) from cells not having expression events. The separated cells can include only one cell or more than one cell (e.g., 10, 100, 1000, 10,000 or 100,000 cells). Gene expression can then be measured in the separated cells by, e.g., RT-PCR or a transcriptomic analysis of RNA in the cells.

The details of one or more embodiments of the invention are set forth in the description below. Other features, objects, and advantages of the invention will be apparent from the description and from the claims.

DETAILED DESCRIPTION OF THE INVENTION

Figure 1:
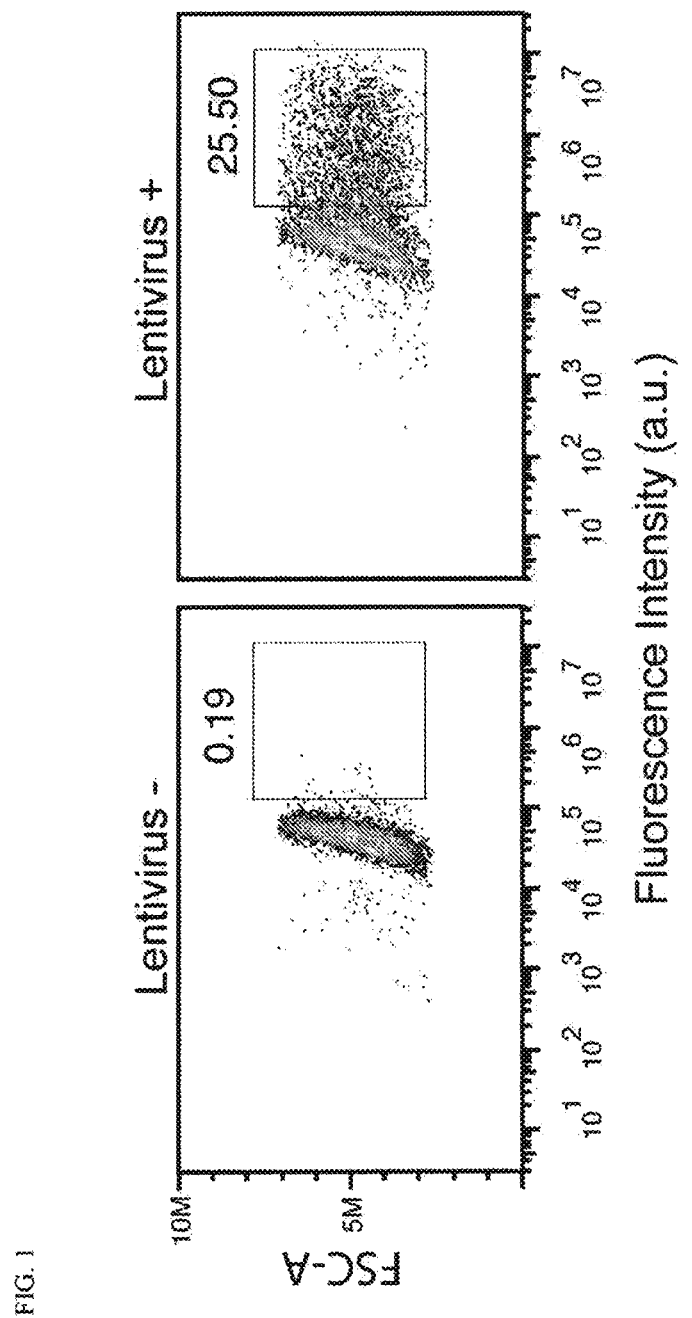
FIG. 1 is a graph of fluorescence intensity versus forward scattered channel A (FSC-A) for the FC readouts described in Example 2.

This invention discloses a method for measuring and assessing expression of one or more genes, including RNA transcripts that code for proteins, for example, messenger RNA (mRNA) and pre-mRNA, and those that do not.

As disclosed herein, the method can be used to assessing RNA transcripts in cells the gene expression of which changes in response to various inductions. Induction may be naturally occurring or stimulated by any known ligands for cellular receptors including but not limited to TCRs and involve, in principle, any receptor or ligand (for example, Toll receptor-like or chemokine receptors and their ligands) or compound that initiates a signaling cascade and may result in transcript synthesis and expression of certain genes, for example, at least one cytokine gene such as IL-2, TNFα, or IFNγ.

In some embodiments, the induction is stimulation by a compound or compounds that bind specific receptors and thereby initiate gene expression, for example, a peptide or mixture of peptides associated with MHC I or MHC II molecules. The compound or compounds may be derived from a microorganism, for example, stimulatory molecules that are *M. tuberculosis*-derived immunogenic peptides. Induction of gene expression, for example stimulation of T-cell receptor signaling and downstream gene expression may be by APCs that are present in the cell population being investigated. Alternatively, stimulation may be by artificial APC (aAPC). A peptide or mixture of peptides that associate with MHC class I or class II molecules may be added to APC or aAPC, preferably at a concentration in the range of 1-20 µg/ml to produce peptide-loaded MHC molecules that interact with TCRs. Certain embodiments of methods of this invention include co-stimulation with at least one monoclonal antibody in addition to APC or aAPC. With aAPC, the mAb may be bound to the aAPCs.

The method of this invention allows one to carry out rapid and sensitive measurements of changes in cell population composition and function that occur during evolution of infectious or non-infectious disease and associated progression of pathology. These measurements can characterize the properties of neoplastic and/or malignant cells of hematopoietic and non-hematopoietic origin, and of cells involved in autoimmune disease.

The method can also be used in monitoring of response during therapy to treat the disease state. For infectious disease, immune control in response to antibiotic therapy can be determined by correlating progress in eradicating a pathogen, for example *M tuberculosis*, with changes in cellular responses to stimulation, such as responses of functional T-cell subsets to antigenic peptides.

Methods of this invention are generally applicable to virtually all cells, mammalian (including but not limited to human) and lower eukaryotic species, that express specific receptors capable of initiating signaling cascades upon ligand/stimulatory molecule binding. They can be applied to populations of bacteria as well as to multicellular organisms. Certain preferred embodiments are the application of methods of this invention to animal cells, including but not limited to human cells. A suitable source provides a sufficient number of cells for detection of rare events and/or for statistical analysis. In some embodiments that is as few as 1000 or even 100 cells. In many embodiments, for example where the cells are T cells, a source that provides at least 10,000 cells is preferred. More preferably, the source provides at least 100,000 cells or at least one million cells. Suitable sources include blood samples and tissue samples, for example, biopsy samples. Tissue samples must be separated into individual cells, that is, disaggregated tissue is required for processing.

As mentioned above, methods of this invention include rapid induction, not exceeding 5 days and preferably less, for example 4, 3, 2, or 1 day, or 16, 12, 10, 8, 6, or 4 hours. A preferred induction time is from 30 minutes to 8 hours, preferably from 30 minutes to 6 hours, more preferably from 30 minutes to 4 hours, and even more preferably from 30 minutes to 2 hours.

Methods of this invention include rapidly measuring expression of one or more genes in immune and non-immune cells based on activation and functional consequences induced by ion fluxes, including but not limited to those caused by ionophores and/or mitogens, or by signaling through cell surface or intracellular receptors, including but not limited to pattern recognition receptors, including toll-like receptors and NOD and NOD-Like receptors, G protein coupled receptors, including chemokine receptors, polypeptide hormone receptors, cytokine receptors, B cell receptors, or TCR. Methods according to this invention are believed to advance medical care for various infectious and non-infectious pathologies. Preferred embodiments comprise detecting expression of RNA, including both mRNA and pre-mRNA, for one or more cytokines in individual lymphocytes, whether in isolated PBMC, T cells, or in whole-blood samples (rather than isolated PBMC) and also other types of cells as indicated below. Methods according to this invention apply, for example, to analyzing $CD3^+$ $CD4^+$ T cells (T helper 1 or Th1 cells) that produce IL-2, IFNγ, and TNFα; $CD3^+CD4^+$ T cells (T helper 2 or Th2 cells) that produce IL-4, IL-5, IL-6, IL-10, and IL-13; CD3+CD8+ T cells that produce (IL-2, IFNγ, TNFα, MIP-1α and other chemokines) and other specialized T-cell subsets, including but not limited to Th17 and Treg cells, or other lymphocyte subsets, including but not limited to NK cells, NKT cells, subpopulations of macrophages and dendritic cells, cells comprising endothelia and epithelia of various body organs or cells of the nervous system, including but not limited to neurons and glia, and the pre-mRNA and mRNA for cytokines, chemokines and functional molecules (for example, see Table 2) produced by these cells.

Certain methods according to this invention comprise ex vivo stimulation of cells, or induction of specific molecular interactions leading to expression of activation markers and modulating cellular functions. Stimulation may be performed immediately or performed on cells after culturing in a culture medium. Stimulation may be natural, that is, simply incubating the cells in culture. Preferably, stimulation may be promoted by incubating the cells in culture with one or more compounds that trigger specific receptors/ligands and induce signaling cascades. These compounds may be synthetic or derived from microorganisms, including but not limited to bacteria, viruses and fungi, for example, lipopolysaccharides, lipoarabinomannans, peptidoglycans, mycolic acids of bacterial origin, or proteins of viral origin, including but not limited to Epstein Barr virus or cytomegalovirus (for example, proteins ebvIL-10, cmvIL-10 and UL146, respectively), or fungal (for example, *Cryptococcus-* and *Aspergillus*-associated) galactoxylo- and galactomannans and soluble antigens; polypeptide hormones, for example, platelet-derived growth factor or VEGF; cytokines; and antigens, including antigenic peptides. A preferred method of stimulation is with artificial antigen presenting cells (aAPC; see below).

Methods according to this invention further include detection of individual cells, including particularly activated cells, having a biomarker signature, preferably a multiple biomarker signature, namely one or more RNAs, including particularly mRNAs or pre-mRNAs in situ in intact cells.

Preferred methods according to this invention comprise detecting induced gene expression, for example for cytokines, and most preferably for multiple cytokines, in individual cells, for example activated T cells, by labeling expressed RNA molecules, including mRNA or pre-mRNA molecules, in fixed, permeabilized cells utilizing sets of fluorescently labeled hybridization probes and washing away unbound probes. Single-molecule sensitivity is obtained by employing multiple nucleic acid hybridization probes that provide multiple fluorescent labels for each RNA target. These may be a small number of probes multiply labeled with a particular fluorophore or probes labeled to produce fluorescence by fluorescence resonance energy transfer (FRET) when they are hybridized to cognate mRNA or pre-mRNA. Preferred methods of this invention utilize a larger number, for example, 10-100, more preferably 20-60, even more preferably 30-50, for example about 50, shorter oligonucleotide probes, each labeled with a single fluorescent dye, that bind simultaneously to a target sequence. The attachment of many labels to each RNA molecule renders the cell sufficiently fluorescent above background that it can be detected by FC methods.

Further, methods according to this invention include detection and analysis of individual cells expressing target RNA or RNAs by FC. Certain preferred methods of this invention comprise using quantitative FC to detect cells that include RNA expression products of cytokine genes induced in desired cells by APC or aAPC stimulation.

FC comprises a fluidics system for hydrodynamic focusing to create a single file of cells. Single cells can then be interrogated for fluorescence emission at one or multiple wavelengths. FC is a routine technique in clinical pathology laboratories. For example, immune phenotyping by FC is an important tool in the diagnosis and staging of various haematologic neoplasms. Essential FC steps are labeling cells with one or more fluorescent moieties, for example fluorophores, introducing labeled cells into a flow cytometer, illuminating each cell with an excitation light source such as a laser that emits at a wavelength that excites the fluorescent moieties, and detecting emitted fluorescent light using filters and mirrors that distinguish specific emitted wavelengths for each fluorescent moiety being used, so as to acquire data that reveal the presence and, preferably, the amount of each fluorescent moiety associated with each cell based on the excitation and emission.

As disclosed herein, FC can be used for detecting cells expressing RNA by utilization of multiple singly-labeled fluorescent hybridization probes. A most preferred embodiment is detection of RNA (mRNA or pre-mRNA) expressed from cytokine genes in the T-cell fraction of isolated. PBMC that had been stimulated by presentation of *M tuberculosis* Ags by either endogenous APC or, more preferably, aAPC. RNA for multiple cytokines can be detected by use of probes that are specific for each species of RNA and that are labeled with a different fluorescent moiety (for example, a different fluorophore) for each species of RNA detected.

In methods of this invention, FC is performed on populations of cells (from as few as 10,000 cells to more than one million cells). Data are acquired for one or more events. An event is a set of measurements for one cell. The data for each event are categorized into user-defined windows, for example, signal for fluorophore A, or signal for fluorophore A that is between an intensity level X and an intensity level Y. The categorization of FC readings is a process called gating, and the events are thus gated, or selected, typically as above a certain threshold or bounded by certain threshold limits. Results can then be presented as absolute numbers of cells in a certain window or, preferably, as a fraction of cells in one or more windows, that is, frequency. For example, in analyzing a disease state, the results might be that 10% of the cells were positive for mRNA A and mRNA B, 7% of the cells were positive for mRNA B and mRNA C, and 2% of the cells were positive for all three of mRNA A, mRNA B and mRNA C. If 10,000 cells are analyzed, the lowest possible positive result is that a certain event occurred once in 10,000 cells. If, on the other hand, one million cells are analyzed, the lowest possible positive result is that a certain event occurred once in one million cells.

Analysis of FC results may include analysis of variance (ANOVA), which is a collection of statistical models for analyzing variances, generally to test significant differences between means for groups or variables by partitioning total variances into components due to true random error and components due to differences between means.

This invention also discloses reagent kits for carrying out the foregoing methods. Kits according to this invention include at least one stimulatory compound, for example proteins or peptides that will stimulate expression of one or more cytokines, as a response characteristic of the disease state to be tested, or aAPC that are loaded with such peptides and that carry co-stimulatory molecules as described below, and one or more sets of oligonucleotide probes that each hybridize specifically to a single sequence present in mRNA or pre-mRNA, preferably wherein each set comprises 20-60 oligonucleotides of 16-20 bases each and each oligonucleotide is labeled with a single flourophore. The kit may additionally comprise other than mRNA-specific probes such as fluorophore-conjugated Abs recognizing cellular proteins or chemical probes tagged with fluorophores binding to targets of interest, reagents for fixation and permeabilization of cells to be analyzed, reagents for hybridization of the included probes with the cells, and reagents for post-hybridization processing, such as washes to remove excess, non-hybridized probe(s) or other unbound labeled probes.

In a preferred embodiment, the method of this invention includes stimulation of TCR signaling and down-stream gene expression by APCs that are present in a cell population or by synthetic beads, which are referred to herein as aAPC. Synthetic beads serve as a mechanical support, i.e., a platform to which proteins (MHC and/or co-stimulatory receptors and ligands) can be attached via chemical, charge or any other type of bonding. Therefore, for example, any plastic surface could be used with or without chemical modification or derivatization as necessary, to serve as a mechanical support, or platform, for aAPC.

The APC interact (or react) with added peptides (or proteins) so that they are associated with (or endogenously processed and presented by) MHC molecules and then can stimulate TCR. The aAPC interact with added peptides that bind to MHC molecules and these peptide-loaded aAPC can then stimulate TCR. The aAPC thus carry one or more classes of peptide-loaded MHC molecules to interact with TCR, with or without one or more antibodies or other type of ligands that interact with co-stimulatory receptors expressed on T cells, such as CD28 and/or CD49d. In certain preferred embodiments stimulatory peptides are *M. tuberculosis*-derived immunogens. The step of stimulating TCRs comprises incubation of TCR-expressing cells with APC or aAPC that comprise MHC class I or class II molecules loaded with appropriate peptides, and, in some embodiments, with co-stimulatory proteins or functional equivalents such as antibodies, peptides, various carbohydrate- and lipid-bearing molecules that bind their targets on co-stimulatory receptors that enhance signaling, resulting in T cell activation.

Functionally different T-cell subsets are often expressed at frequencies close to current detection limits (generally 0.01-0.1%). Thus, their detection requires potent TCR stimulation and highly sensitive detection methods so that even rare T-cell subsets can be directly detected or expanded to numbers above the detection limit of the particular assay method. Methods of this invention comprise inducing effective TCR stimulation by APC that are present in a cell population or by or aAPC, a synthetic bead-based platform containing (i) MHC class I or class II molecules loaded with appropriate peptides and, in certain preferred embodiments, (ii) co-stimulatory proteins (anti-CD28 and/or anti-CD49d monoclonal antibody) that provide additional signals (Oelke et al., 2003, Nature Medicine 9(5):619-24]. Virtually any MHC allele can be attached to the bead platform and any co-stimulatory signal can be provided as a bead-attached specific monoclonal antibody (mAb) or co-receptor ligand, whether naturally occurring or chemically defined. In addition to their superior properties of stimulation, aAPC are very stable: the final cell-sized aAPC, with or without bound synthetic peptides, have a long shelf life in a lyophilized form, and are readily transportable.

In methods of this invention, the procedure for stimulation generally includes obtaining the desired cells from a subject, incubating the cells in culture media, and adding compounds for stimulation of the cultured cells for various times, such as 30 minutes, 1 h, 2 h, 4 h, 6 h, 8 h, 10 h, 12 h, 14 h, 16 h, or longer periods (e.g., 1, 2, 3, 4, or 5 days). Cells might be obtained by biopsy of solid tissue or aspiration of cells in liquid from a site of interest, such as by bronchoalveolar lavage, or the source of the cells may be peripheral blood. Desired cells may be cultured after separating them from unwanted cells by lysing those cells and separating the intact desired cells from the remnants of lysed cells, or by separating the desired cells from the undesired cells based on specific cell characteristics. For example, PBMCs from blood may be cultured either after lysis of red blood cells (RBC) or after recovery based on cell density by sedimentation on Ficoll and removal of Ficoll prior to incubating in culture media. Stimulation can be achieved by adding a stimulating compound as described above (such as a bacterial, fungal, or viral product, or a host protein or peptide) in an amount sufficient to produce the response that will be detected and incubating for a time sufficient to produce the response. The response may be synthesis of a pre-mRNA or mRNA by the cultured, stimulated cells. The response may be interpreted as a signature characteristic of the desired cells' response to the stimulus given.

For obtaining signatures of *M. tuberculosis* infection, for example, HLA-A*0201-based aAPC can be loaded with HLA-A*0201 epitopes (peptides) known to bind to the human HLA-A-0201 MHC class I protein derived from known Ags such as Rv1886c, Rv3874 and Rv3875, and the Ag loaded, A2-based aAPC can be mixed with PBMC at a 1:1 ratio under standard culture conditions for detection of CD8+ T effectors. HLA-DRB1*04-based aAPC can be similarly loaded and used for detection of CD4+ T effectors.

For detection of cells containing copies of one or more specific RNAs, one can utilize for each RNA a set of multiple, fluorescently labeled, oligonucleotide hybridization probes. The oligonucleotide probes may be DNA, RNA, or mixtures of DNA and RNA. They may include non-natural nucleotides, nucleotide analogs and non-natural inter-nucleotide linkages. Each probe may be labeled with multiple fluorescent moieties, for example, multiple copies of a fluorophore, Quantum Dot, or other fluorescent moiety. For example, WO/1997/014816 describes detection of beta- and gamma-actin mRNAs by a single-step in situ hybridization utilizing five probes per target, the probes being about 50-nucleotide long single-stranded DNA labeled with a fluorophore (Fluorescein or Cy3) every tenth nucleotide, that is, five fluorophores per probe. Preferred methods of this invention utilize a larger number, for example, 10-100, more preferably 20-60, even more preferably 30-50, for example about 50, shorter oligonucleotide probes, each labeled with a single fluorescent dye, that bind simultaneously to a target sequence. The attachment of many labels to each RNA molecule renders the cell sufficiently fluorescent above background that it can be detected by FC methods. In most embodiments, each probe set will have a single fluorescent moiety, and each fluorescent moiety will be detectably distinguishable from other fluorescent moieties that are present. If one is detecting whether or not each cell expresses a first RNA or a second RNA, however, both probe sets could be labeled with the same fluorescent moiety.

Background fluorescence presents a different problem for methods of this invention, which utilize FC, than from microscopic smFISH methods, which utilize microscopic visualization of individual RNAs as bright spots in cells. Methods of this invention may employ background reduction techniques. One such technique is to employ FRET between probes that align adjacently on a target RNA. Considering, for example, a first probe and a second probe that align adjacently with the 5' end of the first probe adjacent (within appropriate FRET distance, as is known) to the 3' end of the second probe, one may add a FRET donor to the 5' end of the first probe and add a FRET acceptor to the 3' end of the second probe. With this combination, cells are excited at the absorption wavelength of the donor fluorophore, for example Fluorescein, but signal is detected at the emission wavelength of the acceptor fluorophore, for example Texas Red. Because Texas-Red fluorophores are not excited directly, unhybridized probes or mis-hybridized probes do not fluoresce. Another technique is to employ FRET between a double-strand DNA dye and a fluorophore of a probe set, as is performed in probing with Resonsense probes. In this case a dsDNA dye such as SYBR Green is included (SYBR Green has absorption and emission wavelengths very similar to Fluorescein), and a probe set is labeled with a fluorophore that accepts emission from SYBR Green, for example, TMR. With this combination one can excite the cells at the absorption wavelength of SYBR Green, but detect emission at the emission wavelength of the fluorophore. Because the fluorophore is not excited directly, unhybridized probes do not fluoresce.

Although all regions of an RNA can serve as targets for probes, several factors should be considered in the selection of such probes. Preferably the target region should not be expressed in the cell from other regions of the genome, or more preferably, the target region should not be present elsewhere in the genome. This can be ensured by checking the sequence of the desired target against the databases that list the expressed genes and the entire genome sequences for the organism being studied. This "filtration" of the potentially background-generating sequences can be performed using publically available computer programs such as "repeat masker." The probes can be selected from immediately adjacent regions of the targets or there can be some space between adjacent probes. The length of the probes can vary depending upon the stringency of hybridization.

As shown below, Example 1 demonstrates induction and probing in distinguishing characteristic signatures of gene expression in single cells.

More specifically, assays were carried out to test differentiated THP-1 cells stimulated with irradiated *M. tuberculosis*. Cells were fixed by incubation for 20 minutes with 4% paraformaldehyde after 24 hours of stimulation and then hybridized with probes for two mRNA targets. One was TNFα, a key target for analysis of activated T cells and macrophages. The other was ACSL1 (a lipid metabolism gene, GenBank Accession #BC050073.1), which is also expected to be induced by the stimulus. The probe set specific for TNFα (Ensembl Sequence ID ENST00000376122) comprised 48 probes, each about 20 nucleotides long and terminally labeled with a tetramethylrhodamine fluorophore. The probe set specific for ACSL1 comprised 48 probes, each about 20 nucleotides long and labeled with an optically distinguishable fluorophore, namely, AlexaFluor 596.

For Example 1, expressed RNA products were detected using the known microscopic technique described in Raj et al., 2010, Methods in Enzymology 472:365-386; and Raj et al., 2008 Nature Methods 5: 877-879, namely, smFISH. This technique comprises detection of fluorescent spots as an indication of hybridization of a probe set to an individual RNA molecule. In Example 1, spots corresponding to both mRNAs were detected. Images for TNFα and ACSL1 were merged 3-D stacks for each channel for the same set of cells. Interpretation comprised image processing using a computer program to identify the diffraction-limited spots, corresponding to the individual molecules of mRNA, overlaying them on a DIC image of the cells, and obtaining a cell-by-cell count of the number of mRNA molecules, as described in the references. A large cell-to-cell variation in the number of transcripts for each gene was observed, consistent with previous observation that mRNA synthesis in mammalian cells is highly stochastic. The results, the average spot number for TNFα in stimulated and unstimulated cells based on the total number of spots counted in 50 consecutively analyzed cells, showed that single cell measurements are far more informative than ensemble measurements.

FC data acquisition for methods of this invention can be carried out by conventional FC techniques. Light can be detected in both a forward scatter channel (FSC) and a side scatter channel (SSC). Data can be presented as either or both of density plots and contour diagrams. To visualize cells of interest while eliminating results from unwanted particles, for example debris, FC gating is used. Gates and windows, or regions, are determined in the conventional manner such that positive events appear in a window. To assist in gating to discriminate true positive events from false positives, use of a negative control, that is, probing for something that the cells could not express, is helpful. In principle this is analogous to FC for proteins, where an isotype negative control and/or unstained cells are utilized.

FC detection reveals the number of positive events in a sample, for example, one positive event in 10,000 cells (1/10,000), three positive events in 100,000 cells (3/100,000), or two positive events in one million cells ($2/10^6$). The frequency of an event may lead to a conclusion as to a biological state, for example, a disease state. Alternatively, combinations may do so; for example, 10% of cells in a sample are positive for a first cytokine (cytokine A) and also positive for a second cytokine (cytokine B). As another example, a disease state might be characterized by the following combination: 10% or more of cells being positive for cytokines A and B; 7% or more of cells being positive for cytokine B and a third cytokine (cytokine C); and 2% or more of cells being positive for all three cytokines.

As disclosed herein, it was demonstrated that FC is useful as a read-out for methods of this invention. The experiment described below in Example 2 was designed to test whether signals generated by probe sets hybridized to RNA targets in individual cells can be detected by FC. That example describes steps to detect HIV GAG mRNA in cell cultures expressing it from a lentiviral construct. More specifically, 293T cells were transfected with three plasmids that together allow expression of a recombinant lentiviral construct and hybridized with probes specific for GAG mRNA. FC results are presented in FIG. 1, graphs of fluorescence intensity versus forward scattered channel A (FSC-A) obtained from cells that were not transfected, on the left, and cells transfected with the three plasmids from a lentiviral packaging system, on the right. Both sets of cells were hybridized with a probe set for GAG mRNA. The population of transfected cells produced signals of intensity that was 1-2 orders of magnitude greater than seen with the signals from the outlier untransfected cells (i.e., those above the set threshold). As a control, image-based analysis of smFISH results indicated that about 25% of the cells were expressing the construct. The FC analysis on the same population found the same fraction of cells to be fluorescent. These results demonstrate that mRNA expression is readily detected by FC. Moreover, the data provide guidance for distinguishing a low frequency of strongly stimulated (brightly fluorescent) T cells from outliers in the non-stimulated population. Receiver operating curve (ROC) analysis can define an optimal threshold. ROC analysis is well known to those versed in the art of test development. See, for example, Zweig et al., 1993, Clinical Chemistry 39 (8): 561-577 and Pepe, 2003, The statistical evaluation of medical tests for classification and prediction. New York, N.Y.: Oxford.

The challenges in the detection of transcriptional signatures of T cell activation are two fold—only a small subset of cells are induced and the induced cells express only a few copies of mRNAs per cell. In experiments described in Example 7, the inventors were able to demonstrate both sensitive detection of low frequency responses and simultaneous detection of several mRNA targets by methods of this invention. The assay, which included stimulation, probing of fixed cells and FC, was able to detect cells expressing the IL-2/IFNγ pair with frequency of 3.46% (FIG. 2, right panel), while cells expressing IL-2/TNFα and IFNγ/TNFα cytokine pairs were detected with frequencies of 3.35% and 6.37%, respectively. Comparisons of single- and double-cytokine populations, e.g., IFNγ (4.76-5.40%) vs. IL-2/IFNγ (3.46%), suggested that not all IFNγ producers could produce IL-2. In contrast, most IFNγ producers (5.40%) seemed to also express TNFα, as suggested by the size of IFNγ/TNFα-producing population (6.37%). This result is expected for a population of T cells non-specifically activated by combined TCR triggering and lectin-mediated stimulation (anti-CD3 mAb and phytohemagglutinin). Thus, the assay according to this invention gave results consistent with known T cell biology.

Figure 3:
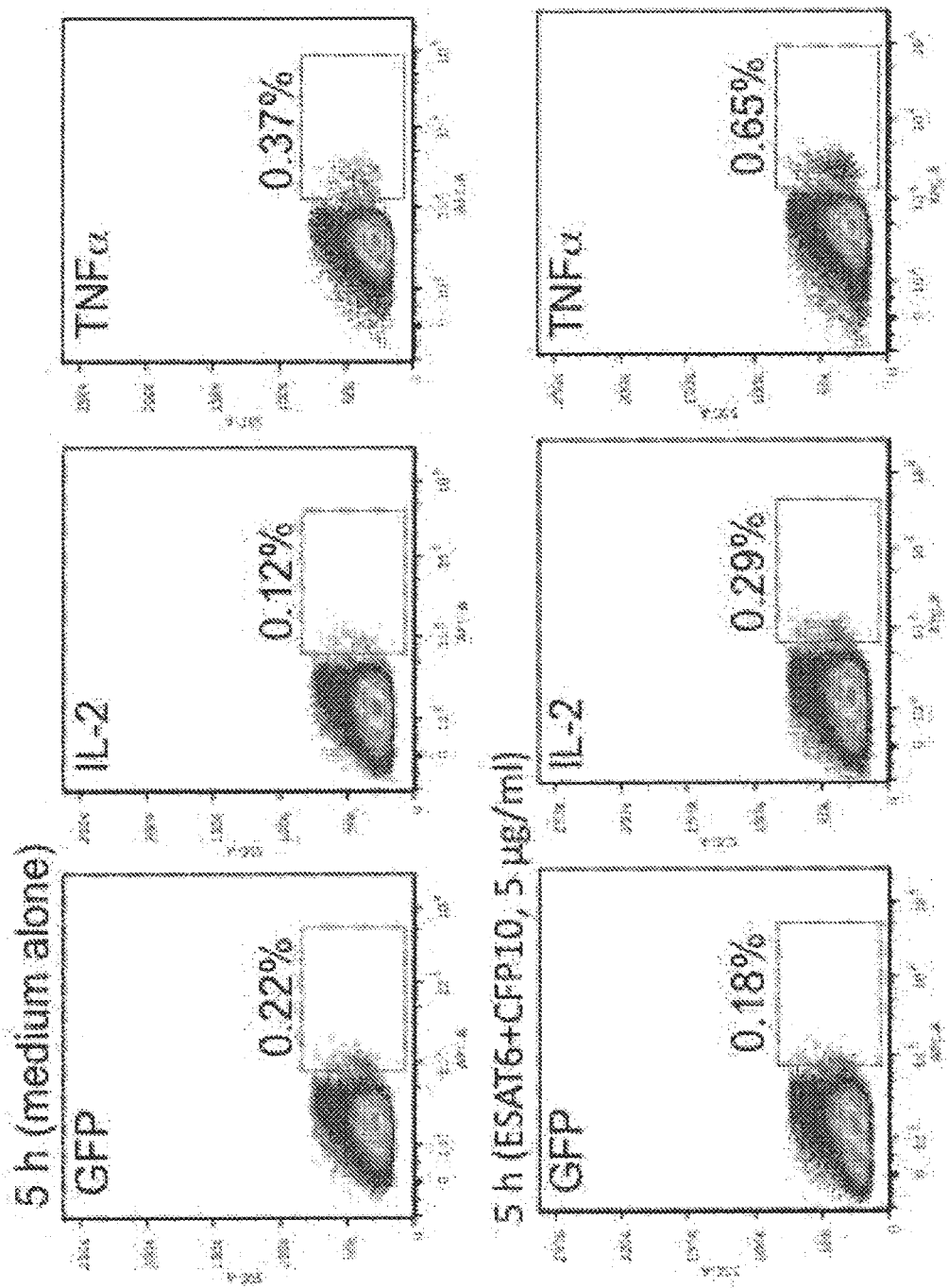
FIG. 3 is a set of six frequency plots from FC detection of samples described in Example 8.

As shown in Example 8, a method according to this invention was applied for the detection of M. tuberuclosis-specific cells stimulated ex vivo. PBMC were incubated for 5 h with a mixture of ESAT6- and CFP10-derived peptides (T-SPOT.TB, Oxford Immunotec, UK) at 5 μg/ml. As shown in FIG. 3, there was a ~2-fold increase in cells expressing cytokine mRNAs in Ag-specific T cells after this stimulation. Therefore, even in the absence of co-stimulation provided by anti-CD28 mAb, the assay detected low frequencies of circulating M. tuberculosis-specific T cells present in this LTBI donor. This result demonstrates the utility of assays according to this invention.

Figure 4:
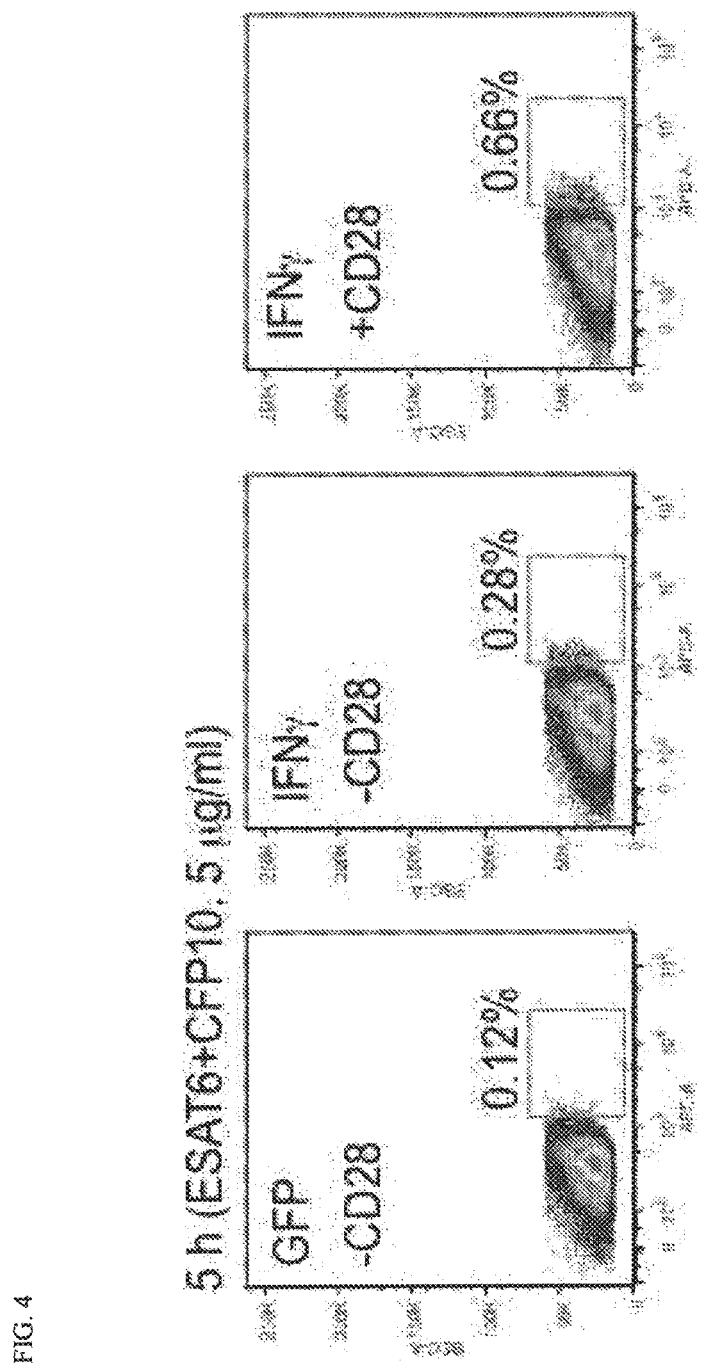
FIG. 4 is a set of three frequency plots from FC detection of samples described in Example 9.

Example 9 describes a method according to this invention with increased signal as compared to Example 8. Engagement of CD28 co-receptor of TCR by mAb was used to deliver superior stimulation of Ag-specific T cells. As shown in Example 8, PBMC were incubated for 5 h with a mixture of ESAT6- and CFP10-derived peptides (T-SPOT.TB, Oxford Immunotec, UK) at 5 μg/ml, but this time with or without anti-CD28 mAb 53D10. Fixed and washed cells were incubated with Cy5-labeled DNA probes specific for green fluorescent protein (GFP, negative control) or IFNγ, and then analyzed by FC. The frequencies of cytokine producers are shown in FIG. 4. More than a 2-fold increase in expression of IFNγ mRNA occurred in Ag-specific T cells of LTBI donor in the presence of anti-CD28 mAb. Non-specific hybridization with control GFP and HIV-1 GAG probes was not affected by CD28 co-stimulation. Example 9 illustrates a distinct strategy to amplify the signal, namely, by providing co-stimulatory signals to TCR specifically engaged by cognate Ag. Furthermore, since co-stimulation mediated by anti-CD28 mAb did not affect non-specific binding of control probes (GFP and HIV-1 GAG), co-stimulation can be used to increase the strength of a specific signal over background noise.

Several strategies are particularly helpful for optimization of assays according to this invention. They include the following:

i) Kinetics of Signal Detection.

Kinetics of mRNA analyte expression for each of the RNA targets (for example, mRNA for cytokines IL-2, IFNγ and TNFα) are determined with cells of a given source (for example, Ficoll-separated PBMC obtained from blood samples of LTBI+ and LTBI– donors) that are stimulated with an appropriate inducer or inducers (for example, a mixture of Ags (for example, ESAT6- and CFP10-derived peptides (T-SPOT.TB, Oxford Immunotec, UK) present at 5 μg/ml), as in Example 8. Expression of each cytokine is then assayed separately in Ag-stimulated. PBMC at various times (for example, 30 min, 2, 4, 8, 12, and 16 h). Particularly for cytokines, PBMC non-specifically stimulated with anti-CD3 mAb and phytohemagglutinin (PHA) serve as positive controls of stimulation. In an assay for analysis of specific PBMC response, a preferred method for measuring non-specific response utilizes and compares PBMC from populations that comprise individuals known to be unaffected and affected by the condition for which the specific response is measured.

ii) Dose Response.

Dose response to Ag stimulation can be similarly determined (for example, for each of the three cytokines) by varying concentrations (1 to 20 μg/ml) of ESAT6 and CFP10 peptide mixture at the optimal signal detection time point. Additionally, non-specific stimulation (anti-CD3+PHA) of PBMC from any donors can be optimized by testing various concentrations, separate and in combination, to provide a standard positive control for a particular assay. In an assay for analysis of specific PBMC response, a preferred method for measuring non-specific response utilizes and compares PBMC from populations that comprise individuals known to be unaffected and affected by the condition for which specific response will be measured.

iii) Signal to Noise Amplification.

Probe sets with more or more highly intense fluorophores can be designed. This goal will also be achieved through several improvement strategies. Additionally, probe labeling methods can be modified as described earlier. Hybridization stringency can be optimized empirically in order to increase signal/noise ratio.

A distinct strategy to amplify the signal is by providing co-stimulatory signals to TCR specifically engaged by cognate Ag, as described in connection with Example 9. Conditions for co-stimulation can be optimized as outlined above for kinetics and dose-response to achieve robust detection of multiple RNAs (for example, three cytokines) by assay described herein.

iv) Threshold Determination.

Initial evaluation of a threshold for RNA detection can serve to standardize the optimized assay, although the clinically accepted threshold for a particular assay can be determined at a later point of commercial assay development. In the research phase, one can evaluate the threshold of RNA detection (cytokine expression) in Ag-specific T cells obtained from donors and stimulated ex vivo. The Ag-specific responses can be calculated by subtracting signal from unstimulated PBMC from the values obtained with Ag-stimulated PBMC at optimal time and Ag dose. For each cytokine read-out, a ROC (receiver operating characteristic) curve is estimated to show the trade-off between sensitivity and specificity at various cut points (including the mean of the donors plus two standard deviations), and optimal threshold values are selected to identify Ag-specific responses.

v) Reduction of Blood Volume and Processing Time.

Currently, $2\times10^6$ cells/parameter (for example, each cytokine) that corresponds, on average, to 0.8 ml of blood, are analyzed. By introducing red blood cell lysis of the whole blood instead of Ficol separation in PBMC preparation, and further blood processing modifications such as vacuum-driven sedimentation (96-well format) instead of centrifugation, one can reduce sample volumes and shorten the time of assay. Preliminary experiments indicate that the hybridization time can be reduced to 2 hours (hrs) without a significant loss of signal.

Assay development can proceed by conventional methods. For example, PBMC from three donor groups (active TB, LTBI, and non-infected controls) can be stimulated with HLA-A2- and HLA-DR4-based aAPC loaded with ESAT6 and CFP10 peptides, as in Example 4. Each assay can test a panel of 4 markers of response to stimulation (assayed together based on expression properties) chosen from a group including but not limited to genes shown in Table 1 using 4-color FC for analysis. This allows all targets to be assessed for each donor. Markers selected in initial tests can be re-tested in combinations chosen to group together genes expressed at similar levels in each group. Statistical analysis can be performed as described in Example 4. Where desired, one can also measure expression of targets induced by conventional APC stimulation to confirm the ability of aAPC to improve detection sensitivity for multiple analytes within single cells. Further, an assay can also be tested by fluorescence microscopy. Statistical analysis can be performed as described in Example 5.

The experiment described in Example 10 demonstrates that the same methodology, which is referred to as "FISH-Flow" used for detection of cytokine mRNAs expression in T cells, can be successfully utilized in other types of cells, including but not limited to primary macrophages. Moreover, the experiment demonstrates that responses to different stimuli can be distinguished in primary macrophages by monitoring expression of a single gene at different times.

Figure 5:
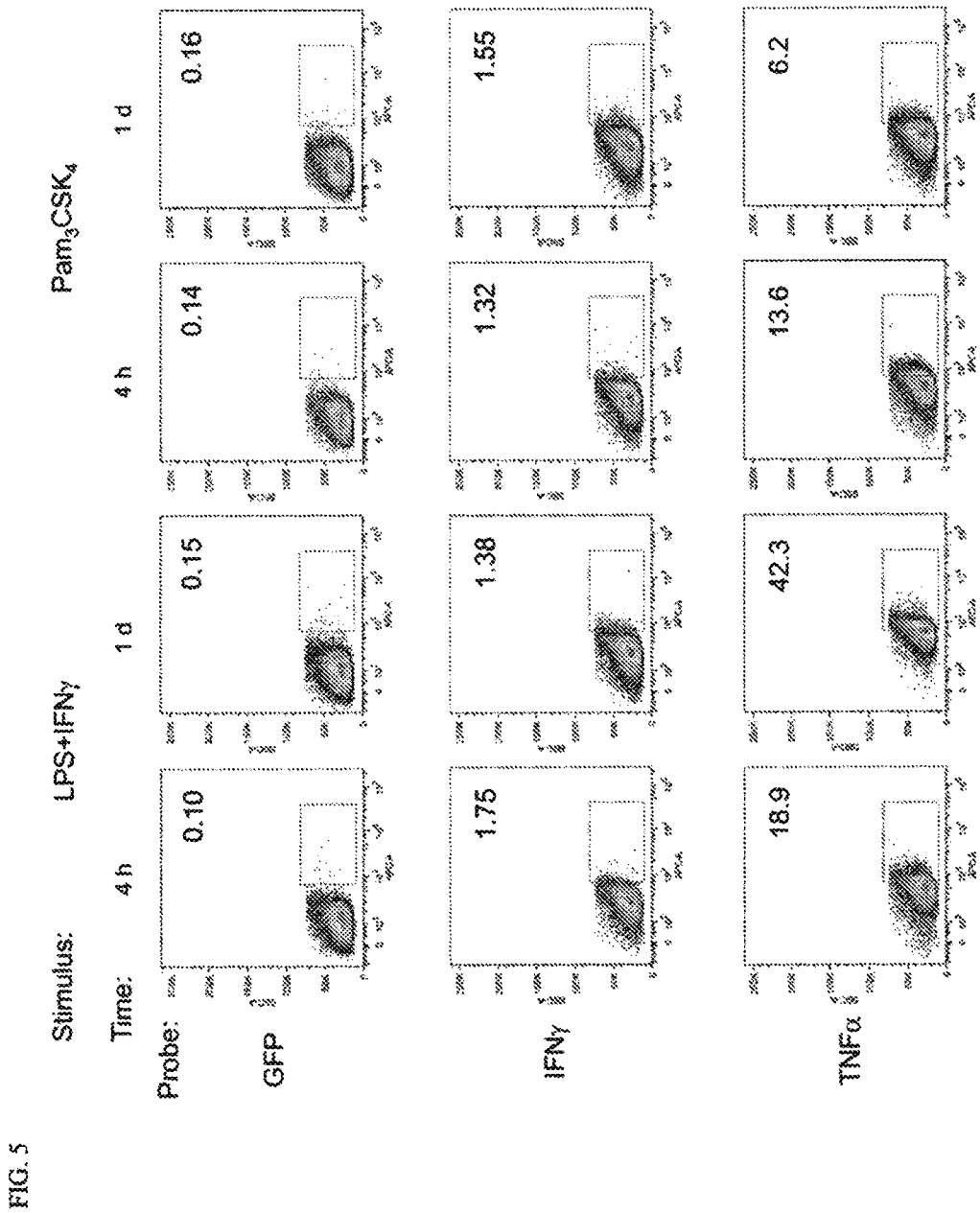
FIG. 5 is a set of twelve frequency plots from FC detection of samples described in Example 10.

The results shown in FIG. 5 show that background expression assessed by a GFP negative control remained constant but negligible (approx. 0.1-0.2% of gated cells). Treatment with a mixture of lipopolysaccharide (LPS) and IFNγ or N-palmitoyl-S-[2,3-bis(palmitoyloxy)-propyl]-(R)-cysteinyklysyl)3-lysine (Pam$_3$CSK$_4$) readily induced expression of TNFα transcripts in these cultured macrophages to levels of 6 to 42% of all cells being positive. Robust expression of TNFα transcripts is expected in activated macrophages and contrasted with a modest (less than 2%) expression of IFNγ mRNA, which was unaffected by the choice of stimuli and/or length of stimulation and thus may reflect an unusually high background in these cells rather than the real expression profile. The kinetics of TNFα mRNA expression induced by LPS and IFNγ appears to be different from that induced by Pam$_3$CSK$_4$, with the former stimulation resulting in a sustained prolonged elevation of mRNA levels. In contrast, stimulation of the same mRNA by Pam$_3$CSK$_4$ was significantly less persistent.

Figure 6A:
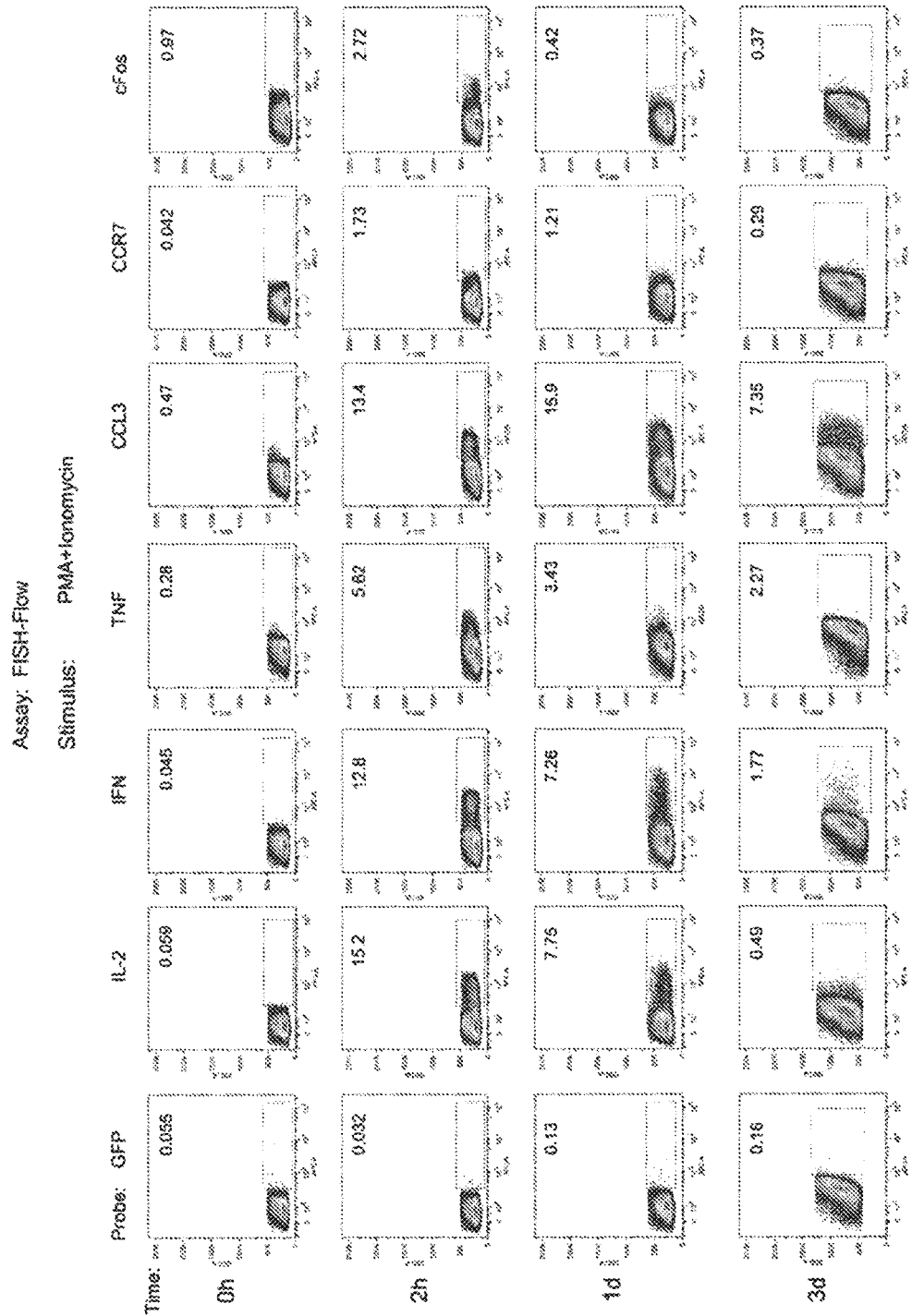
FIGS. 6A and 6B are (A) a set of twenty-eight frequency plots from FC detection of samples probed with mRNA probe sets as described in Example 11 and (B) a set of sixteen frequency plots from FC detection of samples probed with mAbs as described in Example 11.
Figure 6B:
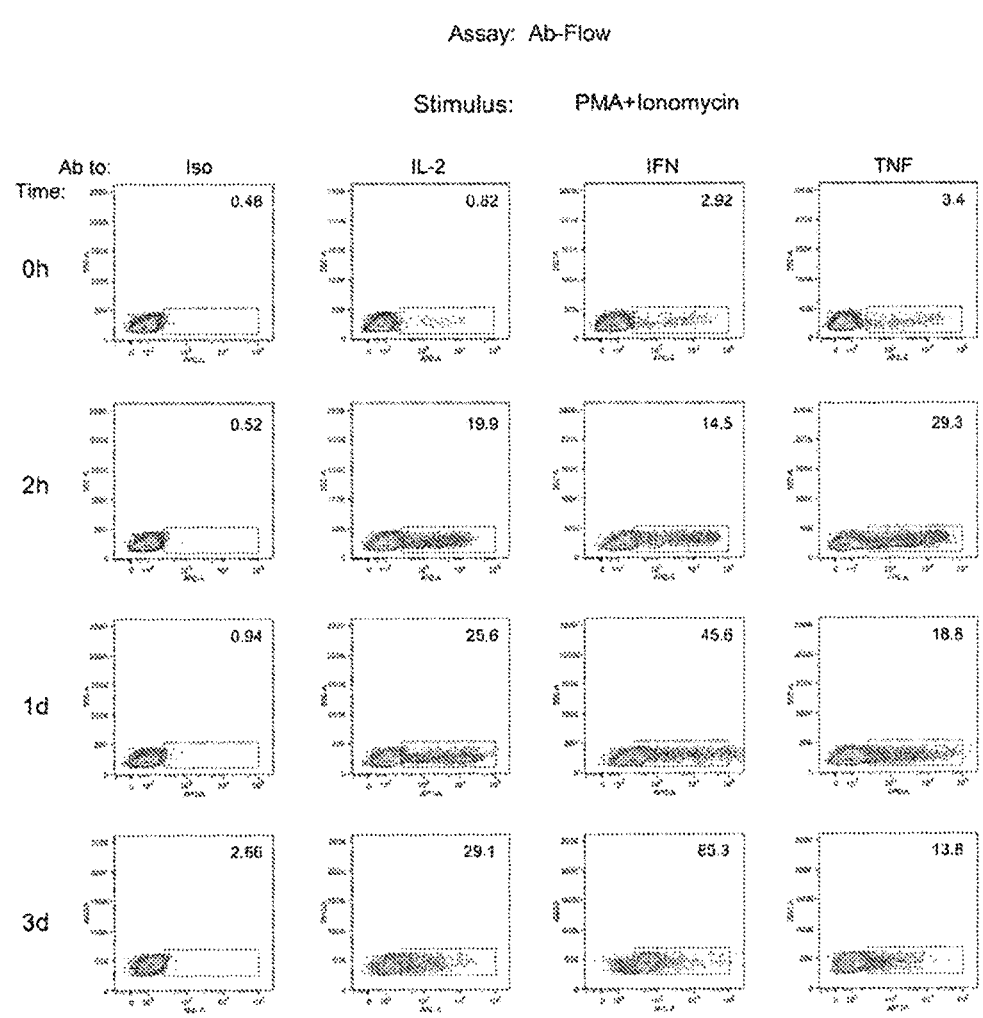

Example 11 demonstrates identification of temporal profiles of gene expression for cytokines, chemokines, and chemokine receptors, which are markers of T cell activation, in stimulated human T cells, comparing flow cytometry results obtained using FISH probes specific for the indicated mRNAs (FIG. 6A) or using mAbs recognizing their protein products (FIG. 6B). The frequencies of cytokine producers by FISH-Flow (FIG. 6A) showed that expression of IL-2, IFNγ, TNFα, CCL3, CCR7 and cFos mRNAs in non-stimulated cells is either negligible (control GFP, IL-2, IFNγ and CCR7) or very low (TNFα, CCL3 and cFos), occurring in <1% of gated cells. Unexpectedly, induced expression of these mRNAs seems to peak at 2 hours after stimulation and then to decline through 1 day and 3 day time points. This is in contrast to the parallel data obtained with the same cells (in the presence of 1 µg/ml brefeldin A) by conventional mAb immunostaining and flow cytometry. Here, non-stimulated cells clearly show basal levels (1-3%) of protein expression detected for at least some markers such as IL-2, IFNγ and TNFα in comparison to a negative control— isotype-matched (Iso) mAb. Furthermore, all the targets are induced at 2 hours and remain elevated in the 3 day time period examined. Thus, no distinct temporal profiles could be detected with mAbs that bind to the cytokines. Example 11 demonstrates differences in kinetics that provide superior profile discrimination with FISH-Flow versus conventional mAb staining and flow cytometry and suggests that the former method provides greatly improved sensitivity for detection of activation.

In order to fully define any cell type functional signatures (i.e., capability to perform specialized biological functions), knowing expression of all other mRNAs in activated cells vs. non-activated (non-responding) cells may be important. The study reported in Example 12 demonstrates that FISH-Flow enables labeling of cells that express one or multiple targets in response to stimulation, and that such responders could be isolated from the whole cellular population for the purpose of interrogating their gene expression profiles.

Figure 7A:
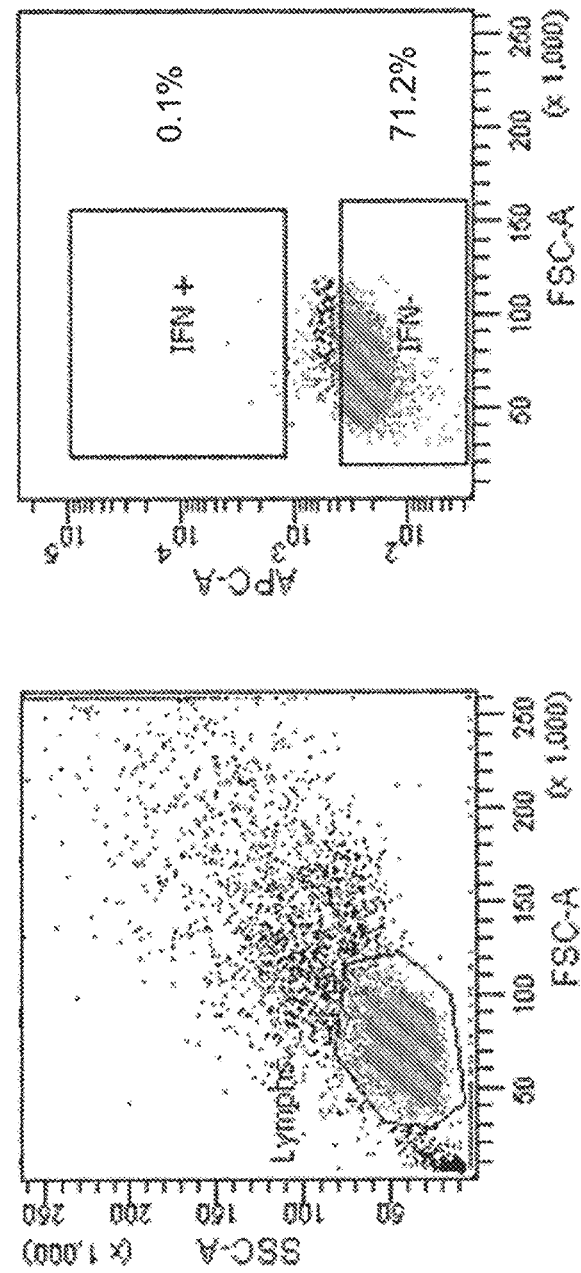
FIGS. 7A and 7B are (A) a set of two frequency plots from FC detection of samples probed with a probe for green fluorescent protein, before (left panel) and after (right panel) additional gating to distinguish the cells as cytokine-positive and cytokine-negative populations, as described in Example 12 and (B) a set of two frequency plots from FC detection of samples probed simultaneously with four mRNA probe sets, before (left panel) and after (right panel) additional gating to distinguish the cells as cytokine-positive and cytokine-negative populations, as described in Example 12.
Figure 7B:
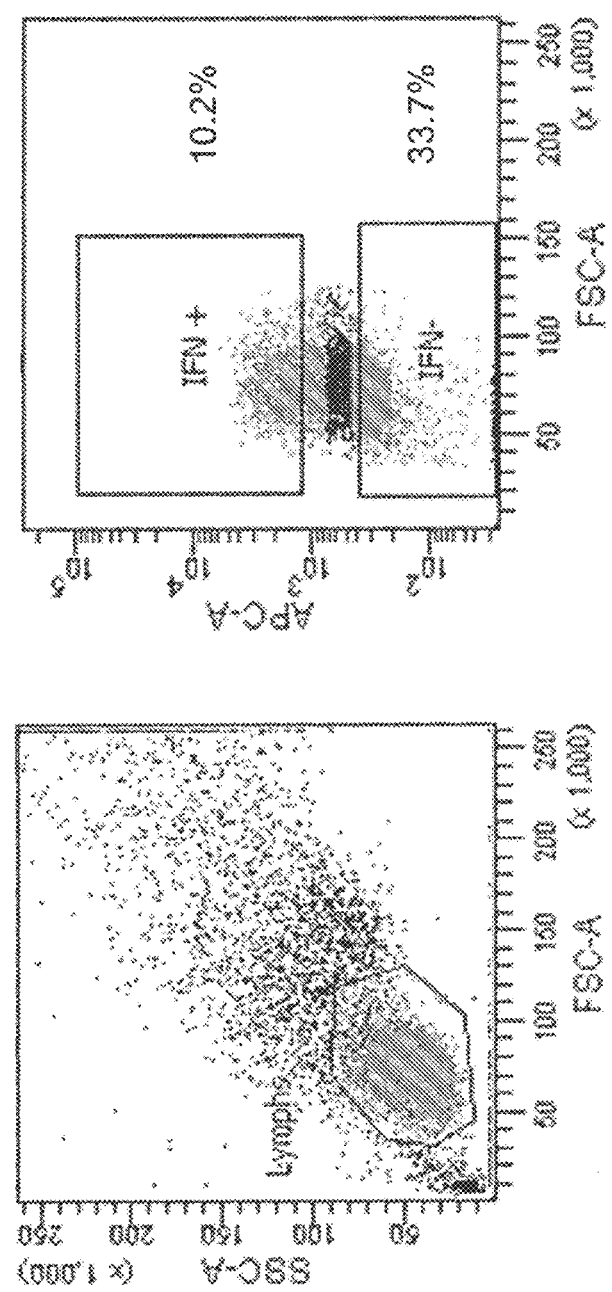

Stimulated human T cells were incubated either with Cy5-labeled DNA probes complementary to RNA specific for GFP and analyzed by FC as a control or with a mixture of several FISH probe sets (Table 3) reactive with IL-2, IFNγ, TNFα, and CCL3 mRNAs, all probes singly-labeled with Cy5. Results obtained with the GFP probes are shown in FIG. 7A. Results obtained with the probes mixture are shown in FIG. 7B. After gating for the lymphocyte population (left panel in each figure), conservative additional gating was applied to separate the analyzed lymphocytes into two distinct populations (right panel in each figure) that would distinguish cells expressing IFNγ (IFN+) from the non-expressing cells (IFN−). The gating set up for GFP-probed cells (FIG. 7A) defined two populations, 0.1% in the IFN+ population and 71.2% in the IFN− population, out of all analyzed lymphocytes. The IL-2:IFNγ:TNFα:CCL3-probed cells (FIG. 7B) were 10.2% IFN+ and 33.7% IFN− with the same gating. The latter FISH-probed cells (FIG. 7B) were separated into the positive and negative populations by fluorescence-activated cell sorting (FACS) in order to perform gene expression analysis on isolated activated and non-responding cells. The sorted cell populations were analyzed to demonstrate distinct gene expression profiles consistent with their reactivity with specific FISH probes. Expression of mRNAs encoded by two genes, IFNγ and "housekeeping" GAPDH (control), was chosen to exemplify an embodiment of this aspect of the invention. The sorted cell populations were subjected to RT-PCR using primers specific to one of the two genes. Quantitative measurement of amplified product was made by including SYBR Green dye in the amplification reaction mixture. Results, shown in FIG. 8A, demonstrate that IFNγ-specific primers detect a greater abundance of target in IFN+ cells that were identified with probes for IL-2, IFNγ, TNFα and CCL3 than in IFN− cells that were minimally labeled with those probes. Amplification of a control GAPDH signal that is unaltered by activation status is expected to be similar in both activated and non-responding cells. Slightly reduced amplification seen with GAPDH-specific primers in activated cells reflects the fact that this sorted population is significantly smaller, and, therefore, could yield less mRNA.

These results (confirmed by size analysis, FIG. 8B) demonstrate that gene expression may be further analyzed in desired subpopulations of cells identified using the FISH-flow platform of this invention by applying methods known to those well-versed in the art for sorting and obtaining subpopulations of cells, and methods for gene expression measurement such as RT-PCR or transcriptomic analysis. The subpopulation that can be identified and studied may contain one cell or more than one cell, including but not limited to 10, 100, 1000, 10,000, 100,000, or more cells.

EXAMPLES

Example 1. Demonstration of Induction and Probe Sets

This example demonstrates the use of artificial stimulation of cells to produce RNA, in this case mRNA, and the use of sets of singly labeled fluorescent probes to hybridize to expressed RNAs.

For this example, the technique of smFISH was used to visualize spots corresponding to individual molecules of mRNAs bound to the probes. See Raj et al., 2010, Methods in Enzymology 472:365-386; and Raj et al., 2008, Nature Methods 5: 877-879. The probe hybridization conditions and cell washing conditions are described in these references. The procedure departed in one important way. In order to avoid the loss of cells during washing steps 0.5% fetal bovine serum was included in the washing solutions. A set of nucleic acid probes, here DNA probes, were selected for TNFαmRNA, a key target for analysis of activated T cells and macrophages, and tested differentiated THP-1 cells stimulated with irradiated M. tuberculosis. Also included were a second set of DNA probes, labeled with a fluorophore of different color and designed to bind to ACSL1 mRNA (a lipid metabolism gene). The latter gene was also expected to be induced by the stimulus. The probe set specific for human TNFα comprised 48 probes, each about 20 nucleotides long and terminally labeled with a tetramethylrhodamine fluorophore. The probe set specific for human ACSL1 gene comprised 48 probes, each about 20 nucleotides long and labeled with an optically distinguishable fluorophore, namely, alexafluor 594. The sequences of the probes are listed in the sequence listing at the end of this description (Table 3). Although the probes listed in each set are suitable for detection of the target mRNA, alternative probes selected from different regions of the target RNAs can also be used as described in Raj et al., 2010, Methods in Enzymology 472:365-386; and Raj et al., 2008, Nature Methods 5: 877-879. As discussed above, spots corresponding to both mRNAs in the cells were detected. The number of TNFα RNA molecules increased from 0.24 per cell without induction to 14 per cell, on average, following stimulation.

Example 2. Use of FC to Detect Cells Expressing a Gene

In this experiment assays were carried out to detect HIV GAG mRNA in cell cultures expressing a lentiviral construct.

Briefly, 293T cells were transfected with three plasmids that together allow expression of a recombinant lentiviral construct and hybridized with probes specific for GAG region of HIV mRNA (GenBank Accession #AY835771.1). The sequences of the probes are listed at the end of this specification (Table 3). The probes were hybridized and the cells were washed according to the procedures described in Raj et al., 2010, Methods in Enzymology 472:365-386; and Raj et al., 2008, Nature Methods 5: 877-879, which are incorporated by reference herein in their entireties. Again, to avoid the loss of cells during washing steps, 0.5% fetal bovine serum was included in the washing solutions. FC was then performed to detect cells expressing the construct. A gate was established based on the fluorescence of cells that were not transfected. In cells that were transfected, about 25% of the cells expressed the construct as shown by signal of greater intensity than the level set by the gate. FC results are presented in FIG. 1, which shows two graphs of fluorescence intensity ("a.u.") versus forward scatter ("FSC-A"). The graph on the left (Lentivirus−) shows cells that were not transfected. The graph on the right (Lentivirus+) shows cells that were transfected with three plasmids from a lentiviral packaging system.

Example 3. Detection of Cytokine Gene Expression Stimulated by M-TB Derived Peptides PBMC are obtained from uninfected, asymptomatic latent infection (LTBI), and active TB donors. T cells are activated by addition of the peptide mixture used in the T-SPOT.TB IFNγ Release Assay (IGRA) (Oxford Immunotec, Marlborough, Mass.) according to the manufacturer's instructions, which is derived from immunodominant mycobacterial Ags Rv3875 (ESAT6) and Rv3874 (CFP10). At various times (4 to 120 h), stimulated cells are fixed and permeabilized and then hybridized with one or more of the probe sets described below. The cells are analyzed by FC to determine the frequency of cells that express the targets, individually and in combination, using available filter sets that distinguish among the fluorophores used to label the probes.

The probe set for TNFα is the probe set specified in Example 1. Two additional probe sets, one for TL-2 and one for IFNγ are prepared, each having 50 probes (Ensembl Sequence IDs ENST00000226730 and ENST00000229135 respectively). The probes in all three sets are linear (random coil) oligonucleotides 15-25 nucleotides long, labeled with a single fluorophore. The three fluorophores used for the three sets are optically distinguishable. These three cytokine genes are known markers for T-cell activation and proliferation that distinguish T-cell subtypes. The target transcripts are sufficiently long to permit the use of at least 50 probes for each.

To detect marker expression in a small fraction (≤0.01%) of cells by FC, results for $1\times10^6$ events are collected. To determine statistical significance for differences between donor groups, a threshold for separation of non-responsive from responsive cells is determined by ROC analysis (see, e.g., Zweig et al., 1993, Clinical Chemistry 39 (8): 561-577 and Pepe, 2003, The statistical evaluation of medical tests for classification and prediction. New York, N.Y.: Oxford), and the frequency of positive cells is determined. A mixed-model ANOVA can be used to analyze the data. Data is transformed (e.g., log-transformation), prior to analysis. In cases where a simple transformation is insufficient to address ANOVA assumptions, a non-parametric analog of the statistical approach is applied.

A detectable frequency of expression for all three markers is found in the activated cells. The frequencies of cells that express different combinations of the markers is the signature of the disease.

Example 4. Assay for M. Tuberculosis-Specific Effector T Cells

This example describes assays for detecting M. Tuberculosis-specific effector T cells.

a. Detection of CD8+ T Effectors.

TB patients are HLA typed by FC detection of PBMC immunostained with allele-specific mAbs BB7.2 and 0222, or by PCR confirmation. HLA-A*0201-based aAPC is loaded with known individual HLA-A*0201 epitopes (peptides) derived from Rv1886c, Rv3874 and Rv3875.

These peptides are derived from immunodominant Ags of M. tuberculosis. PBMC are isolated from HLA-A2-typed TB patients and are stimulated with the Ag-loaded, A2-based aAPC at 1:1 ratio under standard culture conditions. Alternatively, isolated PBMC are incubated with added peptides for T cell stimulation by endogenous APC. At various times from 4 to 120 h, cells are fixed and permeabilized and incubated with specific probes for IL-2, IFNγ, and TNFα. Negative controls include PBMC from healthy, non-infected (IGRA-negative) donors stimulated with the above-described Ag-loaded aAPC and PBMC from positive donors stimulated with aAPC loaded with the irrelevant melanoma-specific Mart 1 peptide (26-35 epitope)

and differentiation Ag gp100 peptide (44-59 epitope). Positive controls include PBMC non-specifically stimulated with anti-CD3 mAb+PHA.

b. Detection of CD4+ T Effectors.

First HLA-DRB1*04-based aAPC is constructed using the methodology described above for the assembly of HLA-A*0201-based aAPC. A major aspect of this approach is the expression of a soluble form of HLA-DR4 molecules, which requires pairing of the class II a and b polypeptides during biosynthesis. To facilitate subunit pairing of soluble analogs of MHC class II molecules, the IgG molecule is used as a molecular scaffold: it is divalent and can be readily modified to accommodate a wide variety of protein domains. Modified a and b chains are cloned in a dual promoter baculovirus expression vector. The cells infected with this vector secrete approximately 0.5-2.0 mg/ml of the soluble HLA-DR4-Ig-like material. To assemble soluble MHC class II HLA-DR4-Ig complexes using a generic cloning vector pZig, DNA encoding class II extracellular domains of α and β chains of DR4 proteins is ligated to DNA encoding Ig heavy and light chains using endonuclease restriction sites; and the chimeras are ligated sequentially to a modified pAcUW51 vector. The yield, purity, and integrity of secreted proteins is confirmed by biochemical analysis (SDS-PAGE and Western blotting) with HLA-DR4-specific mAb 0222HA (One Lambda). Purified soluble HLA-DR4-Ig proteins and anti-CD28 mAb at 1:1 ratio are conjugated to magnetic beads (M-450 Epoxy Dynabeads, Dynal Invitrogen).

Known peptides derived from Rv1886c, Rv3874 and Rv3875 and restricted by the HLA-DRB1*04 allele (Table 1) are loaded on HLA-DR4-based aAPC and used to stimulate PBMC derived from non-infected, LTBI and active TB donors. Alternatively, isolated PBMC are incubated with added peptides for T cell stimulation by endogenous APC. After stimulation for various times from 4 to 72 h, cells are probed for IL-2, IFNγ, and TNFα mRNA and analyzed by FC. Negative and positive controls are as described above for CD8+ T cells.

TABLE 1

HLA-A*0201- and HLA-DRB1*04-restricted epitopes

| M. tb protein | HLA-A2 epitope (SEQ ID NO.) | HLA-DR4 epitope (SEQ ID NO.) |
|---|---|---|
| Rv1886c | FIYAGSLSAL (1) | PVEYLQYPSPSMGRD (4) |
|  | KLVANNTRL (2) | LPVEYLQVPSPSMGR* (5) |
|  | GLAGGAATA (3) | PQQFIYAGSLSALLD* (6) |
| Rv1986 | ALGISLTV* (7) | AGRLRGLFTNPGSWR (10) |
|  | FLACFTLIAA* (8) | VGFLACFTLIAAIGA* (11) |
|  | FLIGYGLLA* (9) | LDTVVLLGALANEHS* (12) |
| Rv2220 | GLLHHAPSL (13) | -*** |
|  | SLWKDGAPL (14) |  |
| Rv2659c | RKAAGRPDLRV* (15) | PDPYQAFVLMAAWLA* (18) |
|  | KLLDNHILA* (16) | TMRAHSYSLLRAIMQ* (19) |
|  | FVLMAAWLA* (17) | RAHYRKLLDNHILAT* (20) |
| Rv2780 | VLMGGVPGVE (21) | -*** |
|  | LLDSGTTSI (22) |  |
| Rv3407 | ARVEAGEELGV* (23) | AIGIRELRQHASRYL* (26) |
|  | ALIESGVLIPA* (24) | RLVARLIPVQAAERS* (27) |
|  | RLVARLIPV* (25) | KRTLSDVLNEMRDEQ* (28) |
| Rv3874 | SGDLKTQIDQV* (29) | IRQAGVQYSR** (30) |
|  | IRQAGVQYSR** (30) | EISTNIRQA (31) |

TABLE 1-continued

HLA-A*0201- and HLA-DRB1*04-restricted epitopes

| M. tb protein | HLA-A2 epitope (SEQ ID NO.) | HLA-DR4 epitope (SEQ ID NO.) |
|---|---|---|
| Rv3875 | AMASTEGNV (32) | FAGIEAAASAIQGNV (34) |
|  | LLDEGKQSL (33) | SAIQGNVTSIHSLLD* (35) |

*predicted using software availabe from the website of Immune Epitope Datase And Analysis Resource at immuneepitope.org.
**this epitope is dually class I/II-restricted.
***not needed, only used with class I-based aAPC.

The methods of statistical analysis described in Example 3 are applied to these results. The multiple stimulation approaches in this example also require a mixed-model ANOVA for comparisons.

The foregoing test is able to detect both CD4+ and CD8+ effector T cells in the blood of TB patients based on stimulation with allele-specific HLA class I- or class II-restricted peptides. Activated effector T cells recognizing Rv1886c, Rv3874 and Rv3875 Ags and capable of producing at least a single cytokine, IFNγ or TNFα, are readily detectable. Co-production of two cytokines (IL-2+IFNγ+ and IL-2+ TNFα+) is less frequent in the terminally differentiated T cells that are the majority of effectors in the blood of patients with active TB.

Example 5. Single T Cell Cytokine Profiles Elicited by Infection Stage-Specific Ags PBMC from active TB, LTBI, and non-infected donors are stimulated at various times (4 to 120 h) with HLA-A2- and HLA-DR4-based aAPC loaded with peptide mixtures derived from Rv1886c (active TB stage), and Rv1986, Rv2659c and Rv3407 (LTBI stage). Alternatively, isolated PBMC are incubated with added peptides for T cell stimulation by endogenous APC. The read-out is expression of IL-2, IFNγ and TNFα using three sets of about 50 singly labeled fluorescent probes and FC detection of numbers of expressing cells. To identify Ag candidates that may discriminate between disease states, one-way ANOVAs was used and a generous p-value (p=0.25) as a cutoff. Selected Ags are used to develop a model of responses that distinguishes donor groups using generalizations of logistic regression such as polytomous or cumulative logistic regression.

Stimulation with Rv1886c produces a characteristic, infection stage-associated T-cell cytokine profile: single, double, and triple producers with TB patients and mostly IL-2 producers with LTBI patients.

Example 6. Identification of Functional Effector and Memory Signatures Associated with Infection Stage in Single T Cells Functional markers that are inducible by TCR activation can be measured by methods of this invention so as to accurately describe the main functional T-cell subsets. For this assay candidate markers that are inducible within 4-6 hours after TCR engagement and/or genes that reflect maturation stage and function of known T-cell subsets were selected. The resulting panel of activation and functional markers expressed in effector, effector memory and central memory T cells (Table 2) meets these considerations. The data in Table 2 was compiled from Zinkernagel R M. T cell activation. In: Mak T W, Saunders M E, editors. New York:

Elsevier; 2006. p. 373-401, and from Doherty P. T cell differentiation and effector function. In: Mak T W, Saunders M E, editors. New York: Elsevier; 2006. p. 403-432, and references therein.

TABLE 2

Key markers defining T cell signatures*

| Marker | Subset | Function |
| --- | --- | --- |
| CD27 | Naive, effector | Proliferation, memory response |
| CD40L | Effector | APC activation, primary response |
| CD44high | Effector, memory | Memory response |
| CD69high | Effector, memory | Activation, Th17 response |
| CD107a | CD8+ effector, memory | CTL degranulation |
| CD137 | Effector | CTL proliferation, IFN□ production |
| IL-2 | Effector, memory | Proliferation, Th1 response |
| IFNg | Effector, memory | Th1 response |
| TNFa | Effector, memory | Th1 response |
| MIP-1a | Effector, memory | Th1 response |
| IL-2Ra | Effector, memory | Proliferation |
| CCR1 | Effector | Homing |
| CCR5 | Effector | Homing, activated memory |
| CCR7 | Central memory | Homing, activated central memory |
| CXCR4 | Effector | Homing, migration |
| CXCR5 | CD4+ memory | Homing, migration, memory |
| LPAM-1 | Effector, memory | Homing, CTL differentiation, memory |
| VLA-4 | Effector, memory | Trafficking, adhesion, memory |
| Bcl-2 | Memory | Anti-apoptosis, cell survival |
| Bcl-xL | CD8+ memory | Anti-apoptosis, cell survival |
| Perforin | CD8+ effector | Cytotoxicity |
| Granzyme B | CD8+ effector | Cytotoxicity |

The use of aAPC loaded with peptides (as in Example 3 or 4) to provide stimulation via TCR and co-stimulation via CD28, or alternatively, anti-CD28 mAb combined with peptides (as in Example 3 or 4) for stimulation by endogenous APC, rapidly increases expression of key chemokines and cytokines (including but not limited to MIP-1α, IFNγ, and TNFα) and other co-stimulatory molecules (including but not limited to CD40L, CD137), which in turn further increases responsiveness. The positive feedback augments responses in the time frame utilized for detection and increases the sensitivity of FC results for multi-parameter analysis. The combinations of selected markers are chosen to enable reproducible identification and characterization of individual effector and memory cells and their quantitative analysis in the peripheral blood of donor groups. They serve as T-cell functional signatures. Four-color FC is used so that the signature(s) identified are suitable for analysis with instruments commonly used in clinical settings.

High donor reproducibility is found for data obtained with PBMC stimulated with the commercial mixture of ESAT6 and CFP10 peptides and HLA-A2- or HLA-DR4-based aAPC. The data obtained with this mixture of peptides are very accurate with conventional IGRA based on endogenous APC. The robust stimulation provided by aAPC extends to induction of multiple targets, as described above for standard cytokine targets. Cells expressing multiple markers are also detected at higher frequency than would be the case for conventional APC stimulation. The method of this example permits identification of marker sets that serve as signatures of distinct T cells that are present at different stages of infection, here TB infection.

Example 7. Simultaneous Detection of Two Cytokine mRNAs in Stimulated PBMC

This example shows that it is possible to detect a very small population of fluorescent cells. Briefly, CFSE-labeled PMBC was serially diluted into MITOTRACKER (Invitrogen)-labeled PBMC. It was found that the assay was able to detect the former at a frequency of 0.0013%, demonstrating sufficient sensitivity.

Figure 2:
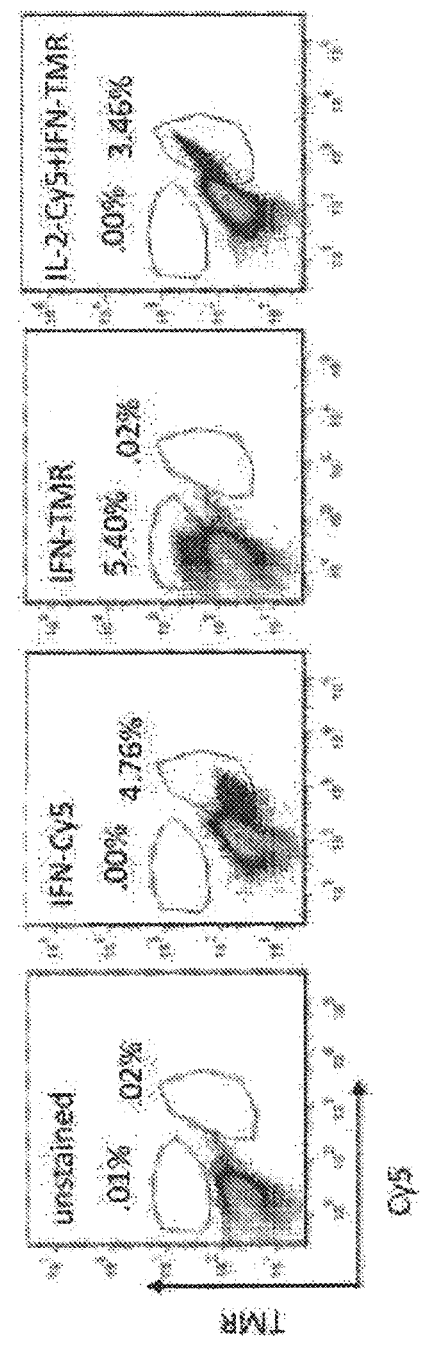
FIG. 2 is a set of four frequency plots from FC detection of samples described in Example 7.

For demonstrating the detection of IL-2, IFNγ and TNFα mRNA, PBMCs were stimulated non-specifically via TCR with anti-CD3 mAb and PHA that is known to induce expression of various cytokines in these cells. After stimulation, the cells were fixed and probed with pairwise combinations of probe sets against IL-2 and IFNγ, IL-2 and TNFα, and also IFNγ and TNFα. One probe set in each pair was labeled with Cy5 fluorophore and the other was labeled with TMR fluorophore. Specifically, PBMC were stimulated with anti-CD3 mAb OKT3 and PHA (both at 1 mg/ml) for 5 days, and then fixed with 4% paraformaldehyde and 70% ethanol. Fixed and washed cells were labeled by incubating with Cy5- or TMR-labeled RNA probes specific for IL-2 and IFNγ, washed again and analyzed by two-color FC (LSRII, Becton Dickinson). Results are shown in FIG. 2. The four plots in FIG. 2 are, from left to right, unstained/mock-hybridized control; single cytokine, IFNγ-Cy5-labeled cells; single cytokine, IFNγ-TMR-labeled cells; and double cytokine (IL-2, Cy5-labeled and IFNγ, TMR-labeled)-labeled cells. Gating shows cell populations expressing one or two cytokines and their frequencies.

Example 8. Detection of Cytokine mRNAs in *M. Tuberuclosis*-Specific Cells Stimulated Ex Vivo In this example, a method according to this invention was applied for the detection of *M. tuberculosis*-specific cells stimulated ex vivo. Circulating *M. tuberculosis*-specific cells are typically present at low frequencies in persons with latent TB infection (LTBI). Blood from an LTBI donor was obtained and stimulated for 5 hr with a mixture of peptides derived from *M. tuberculosis* Ag ESAT6 and CFP10 (commonly used in T-SPOT.TB test). PBMC were incubated for 5 h either in medium alone or with a mixture of ESAT6- and CFP10-derived peptides (T-SPOT.TB, Oxford Immunotec, UK) at 5 µg/ml. Fixed and washed cells were incubated with Cy5-labeled DNA probes complementary to RNA specific for GFP as a negative control, or for IL-2 and TNFα, and then analyzed by FC. The frequencies of cytokine producers are shown in FIG. 3, wherein the three upper plots are for PBMC incubated in medium alone, and the three lower plots are for PBMC incubated in medium containing the Ag mixture.

Example 9. IFNγ Detection in Co-Stimulated PBMC of LTBI Donor

PBMC were incubated for 5 h with a mixture of ESAT6- and CFP10-derived peptides (T-SPOT.TB, Oxford Immunotec, UK) at 5 µg/ml, with or without anti-CD28 mAb 53D10. Fixed and washed cells were incubated with Cy5-labeled DNA probes specific for GFP mRNA (GFP, negative control) (GFP sequence refers to pTREd2EGFP (Invitrogen) or IFNγ mRNA and then analyzed by FC. The frequencies of cytokine producers are shown in FIG. 4. Non-specific staining of control GFP was not affected by CD28 co-stimulation.

Example 10. Cytokine Induction in Activated Macrophages

This example illustrates the use of artificial stimulation of non-T cells, in this case, human macrophages obtained from peripheral blood by adherence to plastic and cultured for 2 weeks under standard conditions (RPMI 1640 media supplemented with 10% fetal bovine serum and antibiotics).

Briefly, activation was carried out with a mixture of lipopolysaccharide (LPS) (100 ng/ml) and IFNγ (20 ng/ml) or N-palmitoyl-S-[2,3-bis(palmitoyloxy)-propyl]-(R)-cysteinyl-(lysyl)3-lysine (Pam$_3$CSK$_4$) (100 ng/ml) for 4 hours or 1 day. Stimulated primary macrophages were removed from the plastic in 0.2-0.3% EDTA in PBS, fixed and permeabilized as described in Example 7, and then incubated with FISH probes specific for IFNγ and TNFα mRNAs (Table 3) and analyzed by flow cytometry. As in Example 8, fixed and washed cells were incubated with Cy5-labeled DNA probes complementary to RNA specific for GFP (Table 3) and analyzed by FC as a negative control. The frequencies of cells detected with the probes by FISH-flow analysis, described above, for instance in example 2, are shown in FIG. 5, wherein the top row is results with the GFP probes, the middle row is for the IFNγ probes, and the bottom row is for the TNFα probes. The first column in each row is stimulation with LPS and IFNγ for 4 hours, the second is stimulation with LPS and IFNγ for 1 day, the third is stimulation with Pam$_3$CSK$_4$ for 4 hours, and the fourth is stimulation with Pam$_3$CSK$_4$ for 1 day.

Example 11. Expression Kinetics of Cytokine and Activation Markers in Activated T Cells This example demonstrates identification of temporal profiles of gene expression for cytokines, chemokines, and chemokine receptors, which are markers of T cell activation, in response to stimulation with PMA (25 ng/ml) and ionomycin (350 ng/ml) of human T cells obtained from peripheral blood on Ficoll gradients. More specifically, after various periods of stimulation (2 hours, 1 day, 3 days), cells were fixed and permeabilized as described in Example 7, and then were either incubated with FISH probes specific for the indicated mRNAs (Table 3) or with mAbs recognizing their protein products followed by flow cytometric analysis. The frequencies of cells detected with the probes by FISH-flow analysis, described above, for instance in example 2, are presented in FIG. 6A, wherein the top row is results without stimulation and the subsequent rows are results after stimulation for 2 hours, 1 day and 3 days, respectively. The first column in each row is results using GFP probes; the second column, using IL-2 probes; the third column, using IFNγ probes; the fourth column, using TNFα probes; the fifth column, using CCL3 probes; the sixth column, using CCR7 probes, and the final column, using cFos probes. The top row is for the GFP probes, the middle row is for the IFNγ probes, and the bottom row is for the TNFα probes. The frequencies of cells detected with the mAbs by FC are presented in FIG. 6B, wherein the top row is results without stimulation and the subsequent rows are results after stimulation for 2 hours, 1 day and 3 days, respectively. The first column in each row is results using a negative control—isotype-matched (Iso) mAb; the second column, using mAb recognizing IL-2; the third column, using mAb recognizing IFNγ; the fourth column, using mAb recognizing TNFα.

Example 12. Separation and Analysis of Activated Fish-Probed T Cells into Cytokine-Expressing and Non-Expressing Populations This example demonstrates that the above-described FISH-Flow enables labeling of cells that express one or multiple targets in response to stimulation, and that such responders could be isolated from the whole cellular population for the purpose of interrogating their gene expression profiles.

Part I: Separation into Populations

Human T cells obtained from peripheral blood on Ficoll gradients and globally stimulated with PMA (25 ng/ml) and ionomycin (350 ng/ml) for 2 hours were incubated either with Cy5-labeled DNA probes complementary to RNA specific for GFP and analyzed by FC as a control or with a mixture of several FISH probe sets (Table 3) reactive with IL-2, IFNγ, TNFα, and CCL3 mRNAs, all probes singly-labeled with Cy5. The frequencies of the cells detected with the probes by FISH-Flow analysis, described above, for instance in example 2, are presented in FIG. 7A and FIG. 7B. Results obtained with the GFP probes are shown in FIG. 7A. Results obtained with the probes mixture are shown in FIG. 7B. After gating for the lymphocyte population based on FSC and SSC (left panel in each figure), conservative additional gating was applied to separate the analyzed lymphocytes into two distinct populations (right panel in each figure)—cytokine positive (denoted IFN+) and negative (denoted IFN−). The gating set up for GFP-probed cells (FIG. 7A) defined two populations, 0.1% IFN+ and 71.2% IFN−, out of all analyzed lymphocytes. The IL-2:IFNγ:TNFα:CCL3-probed (FIG. 7B) populations were 10.2% IFN+ and 33.7% IFN− with the same gating. The latter FISH-probed cells (FIG. 7B) were separated into the positive and negative populations by FACS in order to perform gene expression analysis on isolated cytokine-expressing and non-expressing cells as described below. This approach was also successful for stimulated T cells labeled with only an IFNγ-specific FISH probe that were distinguished and sorted into IFN+ and IFN-subpopulations.

Part II: Cytokine Gene Expression Analysis of FISH-Probed and Sorted into Activated and Non-Responding T Cell Populations.

Activated and non-responding T cells prepared and sorted into separate populations as described in Part I were analyzed to demonstrate distinct gene expression profiles consistent with their reactivity with specific FISH probes. Expression of mRNAs encoded by two genes, IFNγ and "housekeeping" GAPDH (control), was chosen to exemplify feasibility of this goal. RNA isolated from the sorted cell populations by standard methods was subjected to RT-PCR (reverse transcription followed by amplification of the resulting cDNA by the polymerase chain reaction) using a QIAGEN OneStep RT-PCR Kit following the protocol described by the vendor, and using primers specific to one of the two genes. Primer sequences for the amplification reactions were as follows:

```
IFNγ forward primer:
                        (SEQ ID NO.: 36)
5' GAGCATCCAAAAGAGTGTGGAG IFNγ reverse primer:
                        (SEQ ID NO.: 37)
5' TTCATGTATTGCTTTGCGTTGG GAPDH forward primer:
                        (SEQ ID NO.: 38)
5' CCAATATGATTCCACCCATGGC GAPDH reverse primer:
                        (SEQ ID NO.: 39)
5' TCCTGGAAGATGGTGATGGGAT
```

Following the RT incubation and initial denaturation for 15 min. at 94° C., the thermal cycling steps were: 0.5 min at 94°

Figure 8A:
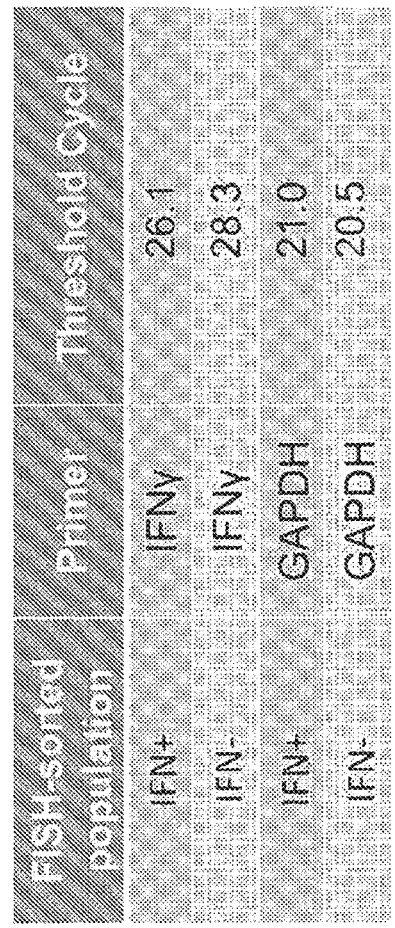
FIGS. 8A and 8B are (A) a table showing the threshold cycles of amplifications of two genes in the sorted (+/−) cell populations described in Example 12 and (B) a photograph showing an electrophoretic gel of the amplification products from the amplifications described in Example 12.
Figure 8B:
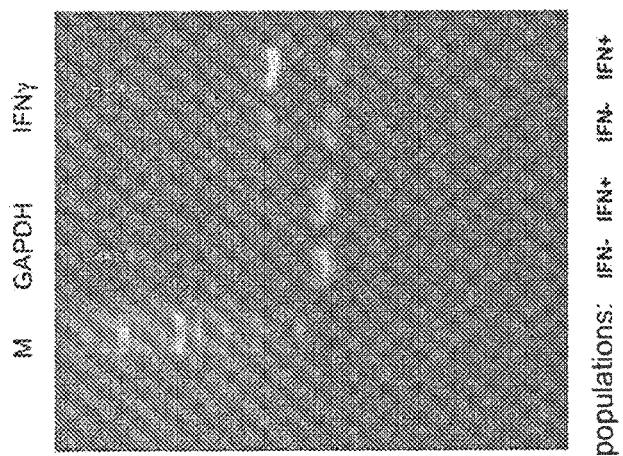

C., 0.5 min at 55° C., 1 min at 72° C. Forty cycles were performed. Detection of amplified products was by SYBR Green dye. Threshold cycles for the amplification reactions are shown in FIG. 8A. To validate the amplification results and exclude a possibility of artifact, the size of identified amplicons was verified with IFNγ- and GAPDH-specific primers by gel electrophoresis. Results are shown in FIG. 8B.

TABLE 3

Probe Sequences

| SEQ ID NO | | SEQ ID NO | |
|---|---|---|---|
| IFNγ probes | | | |
| 40 | atcagaacaatgtgctgcac | 64 | tctaatagctgatcttcaga |
| 41 | ccaaaggacttaactgatct | 65 | tcttgtatcaagctgatcag |
| 42 | gccaaagaagttgaaatcag | 66 | tcatcgtttccgagagaatt |
| 43 | gagctgaaaagccaagatat | 67 | caagagaacccaaaacgatg |
| 44 | tatgggtcctggcagtaaca | 68 | aaggttttctgcttcttta |
| 45 | gacctgcattaaaatatttc | 69 | ccattatccgctacatctga |
| 46 | caaaatgcctaagaaaagag | 70 | cactctcctctttccaattc |
| 47 | tggctctgcattattttct | 71 | gtttgaagtaaaaggagaca |
| 48 | gctctggtcatcttaaagt | 72 | atggtctccacactctttg |
| 49 | cttgacattcatgtcttcct | 73 | ctcgtttcttttgttgcta |
| 50 | ttagtcagcttttcgaagtc | 74 | gacattcaagtcagttaccg |
| 51 | gttcatgtattgctttgcgt | 75 | agttcagccatcacttggat |
| 52 | ttcgcttccctgttttagct | 76 | cgaaacagcatctgactcct |
| 53 | attactgggatgctcttcga | 77 | caaatattgcaggcaggaca |
| 54 | ccccatataaataatgttaa | 78 | cttatttgattgatgagtct |
| 55 | cattacacaaaagttgctat | 79 | gacagtcacaggatatagga |
| 56 | cagaaaacaaaggattaagt | 80 | cacatagccttgcctaatta |
| 57 | ccctgagataaagccttgta | 81 | ttaggttggctgcctagttg |
| 58 | aaacacacaacccatgggat | 82 | gttcattgtatcatcaagtg |
| 59 | ctggatagtatcacttcact | 83 | catattttcaaaccggcagt |
| 60 | aagcactggctcagattgca | 84 | agttctgtctgacatgccat |
| 61 | tcagggtcacctgacacatt | 85 | ctcctgagatgctatgtttt |
| 62 | ttggaagcaccaggcatgaa | 86 | cagtcacagttgtcaacaat |
| 63 | tgagttactttccatttggg | 87 | gtgaacttacactttattca |
| IL-2 Probes | | | |
| 88 | tagcccacacttaggtgata | 112 | gtgaaatccctctttgttac |
| 89 | agactgactgaatggatgta | 113 | ggaatttctttaaaccccca |
| 90 | ttcctcttctgatgactctt | 114 | gaaaaacattaccttcatt |
| 91 | tttcaaagactttacctgtc | 115 | tgttttacatattacacata |
| 92 | aatattatgggggtgtcaaa | 116 | ttatactgttaattctgaa |
| 93 | ctcttgaacaagagatgcaa | 117 | attaagagagtgataggga |
| 94 | ttgaggttactgtgagtagt | 118 | tcctgtacattgtggcagga |
| 95 | caatgcaagacaggagttgc | 119 | tgacaagtgcaagacttagt |
| 96 | ttgaagtaggtgcactgttt | 120 | gctgtgttttctttgtagaa |
| 97 | gcagtaaatgctccagttgt | 121 | tcaaaatcatctgtaaatcc |
| 98 | tcttgtaattattaattcca | 122 | gcatcctggtgagtttggga |
| 99 | gcatgtaaaacttaaatgtg | 123 | tcagttctgtggccttcttg |
| 100 | cttctagacactgaagatgt | 124 | cctccagagggtttgagttct |
| 101 | tttgagctaaatttagcact | 125 | gtcttaagtgaaagttttg |
| 102 | tattgctgattaagtccctg | 126 | gttccagaactattacgttg |
| 103 | atgttgtttcagatcccttt | 127 | catcagcatattcacacatg |
| 104 | attctacaatggttgctgtc | 128 | aggtaatccatctgttcaga |
| 105 | gttgagatgatgctttgaca | 129 | gcacttaattatcaagtcag |
| 106 | ctgatatgttttaagtggga | 130 | atatttaaataaatagaagg |
| 107 | caacaataaatataaaattt | 131 | ataggtagcaaaccatacat |
| 108 | agattaagaataatagttac | 132 | agatccatatttatagtttt |
| 109 | gggcttacaaaaagaatcat | 133 | gaaaccattttagagcccct |
| 110 | aatattttgggataaataag | 134 | ctatatttaacattcaacat |
| 111 | actaaccaatctacatagat | 135 | tcaaatttattaaatagttt |
| TNFα probes | | | |
| 136 | tcctctgctgtccttgctga | 160 | agttgcttctctccctctta |
| 137 | tctgagggttgttttcaggg | 161 | atgtgagaggaagagaacct |
| 138 | tgtccttttccaggggagaga | 162 | gatcatgctttcagtgctca |
| 139 | aagaggctgaggaacaagca | 163 | aaagtgcagcaggcagaaga |
| 140 | tgattagagagaggtccctg | 164 | agaagatgatctgactgcct |
| 141 | tgggctacaggcttgtcact | 165 | agcttgagggtttgctacaa |
| 142 | tggttatctctcagctccac | 166 | tgaggtacaggccctctgat |
| 143 | ttgaagaggacctgggagta | 167 | ttgaccttggtctggtagga |
| 144 | gctcttgatggcagagagga | 168 | agatagatgggctcatacca |
| 145 | acccttctccagctggaaga | 169 | attgatctcagcgctgagtc |
| 146 | tcggcaaagtcgagatagtc | 170 | atgatcccaaagtagacctg |
| 147 | tttgggaaggttggatgttc | 171 | taataaagggattggggcag |
| 148 | agaggttgagggtgtctgaa | 172 | cccaattctcttttgagcc |
| 149 | ttctaagctttgggttccgac | 173 | gtggtggtcttgttgcttaa |
| 150 | attcctgaatcccaggtttc | 174 | tagtggttgccagcacttca |
| 151 | tggaggccccagtttgaatt | 175 | aaagctgtaggccccagtga |
| 152 | tctccagattccagatgtca | 176 | attctggccagaaccaaagg |
| 153 | taggtgaggtcttctcaagt | 177 | ctaaggtccacttgtgtcaa |

TABLE 3-continued

Probe Sequences

| SEQ ID NO | | SEQ ID NO | |
|---|---|---|---|
| 154 | aaacatctggagagaggaag | 178 | tccgtgtctcaaggaagtct |
| 155 | ataaatagagggagctggct | 179 | ccggtctcccaaataaatac |
| 156 | acattgggtcccccaggata | 180 | aaaacatgtctgagccaagg |
| 157 | ttgttcagctccgttttcac | 181 | atcaaaagaaggcacagagg |
| 158 | ggtcaccaaatcagcattgt | 182 | aggctcagcaatgagtgaca |
| 159 | attacagacacaactcccct | 183 | ttctcgccactgaatagtag |
| ACSL1 probes | | | |
| 184 | tgcaatgtgatgcctttgac | 208 | gaaggccattgtcgatgaaa |
| 185 | ttcgccttcattgttggagt | 209 | tgaaatagttccgcagctct |
| 186 | tagaggtcatctatctgcga | 210 | acactaaaccttgatagtgg |
| 187 | ccatttcctctgagcttttct | 211 | gagaagagattgtggaactg |
| 188 | aacaacatgaaggccatcag | 212 | ccctacacttgctgtattca |
| 189 | aagtcaaacacgaacgcttc | 213 | tatgagaagaaccccgaatg |
| 190 | gtgttctctttcctctagca | 214 | aacatgaggtgactgtaagg |
| 191 | ggctcattttggaaagtgtg | 215 | gcacatttatagtatcccct |
| 192 | ctgaggaagtctcaaataac | 216 | gaaacagggagacagaagat |
| 193 | caaagtcctaacccccttgat | 217 | gtagcagacatctcagagat |
| 194 | agacagctgcagaatttgca | 218 | gcactgtactctttagagca |
| 195 | aaagggaacacttccctcta | 219 | gccaggacagttgttcttat |
| 196 | tggtccgcttgtgagattct | 220 | ggacagtagcagggatttaa |
| 197 | ttctgtgaatgcctgtgaga | 221 | cgtaacccttacgaatcaga |
| 198 | gactggagaagaacatgagt | 222 | atgctccaacagaaaccaca |
| 199 | atggttctgagttggatctg | 223 | attttgccagaggctcctat |
| 200 | aatccacgcgttctgatgag | 224 | agagcattctgccatgaaag |
| 201 | aaccctgaaaaggatgga | 225 | cactatagaatctaaggcag |
| 202 | ctgatccaggtaactctttc | 226 | acagttattcaggcgtcaca |
| 203 | gtgagtggttcagtgaagat | 227 | ggcaagttaatcccaacatg |
| 204 | gaaatgcttgcctgagagtt | 228 | gtactcaagtatatactccc |
| 205 | ccaggaaatgaactttccag | 229 | caaatgtggcaaagactcac |
| 206 | ccccaaaacagctgctttaa | 230 | gccctgttgtgcttgtatat |
| 207 | gttaggctaccaagtagtgt | 231 | caaaaccccaaggtgacaaa |
| CCL3 probes | | | |
| 232 | ctgctgcccgtgtcctt | 252 | agaaaggactgaccact |
| 233 | ctcgagtgtcagcgagag | 253 | agcaggtgacggaatg |
| 234 | agtggagacctgcatga | 254 | gaggacagcaagggcag |
| 235 | gagagccatggtgcaga | 255 | tgcagagaactggttgc |
| 236 | cgtgtcagcagcaagtg | 256 | gtagctgaagcagcagg |
| 237 | gtggaatctgccgggag | 257 | agtcagctatgaaattc |
| 238 | ggctgctcgtctcaaag | 258 | caccgggcttggagcac |
| 239 | gcttggttaggaagatg | 259 | cacagacctgccggctt |
| 240 | cactcctcactggggtc | 260 | cgctgacatatttctgg |
| 241 | ctcaggcactcagctcc | 261 | ctcgaagcttctggacc |
| 242 | ccaccgaggtcgctggg | 262 | tcaggctcctgctcctc |
| 243 | acacgcatgttcccaag | 263 | aagaggtagctgtggag |
| 244 | gcaacaaccagtccata | 264 | ccacagtgtggctgttt |
| 245 | tttaagttaagaagagt | 265 | agtataaataaattaaa |
| 246 | aaattacaaaaactaaa | 266 | acacactctgaaatcga |
| 247 | cagagcaaacaatcaca | 267 | aggggacaggggaactc |
| 248 | gttgtcaccagacgcgg | 268 | gctgatgacagccactc |
| 249 | gccatgactgcctacac | 269 | tcagtctggtggctttg |
| 250 | gcatccgatacacattt | 270 | tcacagccctgaacaaa |
| 251 | attatttccccaggccg | 271 | acctttaaaagagcat |
| CCR7 probes | | | |
| 272 | cggtaaaaccacacagga | 296 | caggtccatgacgctctc |
| 273 | cagcacgcttttcattgg | 297 | aatgacaaggagagccac |
| 274 | ttgacacaggcatacctg | 298 | tgtaatcgtccgtgacct |
| 275 | ccactgtggtgttgtctc | 299 | aagactcgaacaaagtgt |
| 276 | cgcacgtccttcttggag | 300 | ggaggaaccaggctttaa |
| 277 | acaaatgatggagtacat | 301 | attgcccagtaggcccac |
| 278 | ataggtcaacacgaccag | 302 | tggtcttgagcctcttga |
| 279 | ttgagcaggtaggtatcg | 303 | tgtagcccagaagggaa |
| 280 | cgaagacccaggacttgg | 304 | tgagcttgcaaaagtgga |
| 281 | gctcatcttgtagatggc | 305 | taggagcatgccactgaa |
| 282 | gtcaatgctgatgcaaag | 306 | ctggacgatggccacgta |
| 283 | ggacagcttgctgatgag | 307 | gcactgtggctagtatcc |
| 284 | tacaggagctctgggatg | 308 | ctgctcctctgaggtca |
| 285 | agagcatcgcatcgcttg | 309 | ctccacatgctctgtgat |
| 286 | ccacctggatggtgataa | 310 | cagaaagccgatcaccat |
| 287 | gaagctcatggccagcag | 311 | gcggatgatgacaaggta |
| 288 | ctcaaagttgcgtgcctg | 312 | atcaccttgatggccttg |
| 289 | atgaagaccacgaccaca | 313 | attgtagggcagctggaa |
| 290 | cgtctgggccaggaccac | 314 | gctactggtgatgttgaa |
| 291 | ttgcttactgagctcaca | 315 | gacgtcgtaggcgatgtt |
| 292 | gacgcaggccaggctgta | 316 | gaaagggttgacgcagca |

TABLE 3-continued

Probe Sequences

| SEQ ID NO | | SEQ ID NO | |
|---|---|---|---|
| 293 | gacgccgatgaaggcgta | 317 | gaagagatcgttgcggaa |
| 294 | gcccaggtccttgaagag | 318 | gagctgctcctggctgag |
| 295 | gatgtgccgacaggaaga | 319 | ctccacactcatggagga | cFos probes

| 320 | tctgcaaagcagacttctca | 344 | tctgcaaagcagacttctca |
|---|---|---|---|
| 321 | ttcagcaggttggcaatctc | 345 | actctagttttttccttctcc |
| 322 | tcggtgagctgccaggatga | 346 | aggtcatcagggatcttgca |
| 323 | agacatctcttctgggaagc | 347 | agtcagatcaagggaagcca |
| 324 | tgaaggcctcctcagactcc | 348 | agggtcattgaggagaggca |
| 325 | acaggttccactgagggctt | 349 | tccatgctgctgatgctctt |
| 326 | atcaaagggctcggtcttca | 350 | tgatgctgggaacaggaagt |
| 327 | tcagagccactgggcctgga | 351 | tcagagccactgggcctgga |
| 328 | tgctgcatagaaggacccag | 352 | actgtgcagaggctcccagt |
| 329 | tctgtggccatgggcccat | 353 | tacaggtgaccaccggagtg |
| 330 | tgtaagcagtgcagctggga | 354 | taggtgaagacgaaggaaga |
| 331 | acagctggggaaggagtcag | 355 | tcattgctgctgctgcccctt |
| 332 | agctgagcgagtcagaggaa | 356 | agtggcacttgtgggtgccg |
| 333 | tgtaatgcaccagctcgggc | 357 | gaagatgtgtttctcctctc |
| 334 | gtctacaggaaccctctagg | 358 | acagataaggtcctccctag |
| 335 | acagcctggtgtgtttcacg | 359 | cttttcaagtccttgaggccc |
| 336 | cttgagtccacacatggatg | 360 | atctccggaagaggtaagga |
| 337 | cactccatgcgttttgctac | 361 | gtgtcactgggaacaataca |
| 338 | ctaactaccagctctctgaa | 362 | aggcctggctcaacatgcta |
| 339 | agagaaaagagacacagacc | 363 | tatgagaagactaaggaga |
| 340 | cccaatagattagttaatgc | 364 | ccaggttaattccaataatg |
| 341 | caatttgaaaatatccagca | 365 | gttaaaatcagctgcactag |
| 342 | ccaggaacacagtagttatt | 366 | ctaatcagaacacactattg |
| 343 | cttagtataatattggtcat | 367 | ccagaaaataaagtcgtatc |

GFP probes

| 368 | tcgcccttgctcaccat | 392 | accccggtgaacagctc |
|---|---|---|---|
| 369 | tcgaccaggatgggcac | 393 | ttacgtcgccgtccagc |
| 370 | gctgaacttgtggccgt | 394 | tcgccctcgccggacac |
| 371 | cgtaggtggcatcgccc | 395 | cttcagggtcagcttgc |
| 372 | ccggtggtgcagatgaa | 396 | agggcacgggcagcttg |
| 373 | agggtggtcacgagggt | 397 | actgcacgccgtaggtc |
| 374 | tcggggtagcggctgaa | 398 | cgtgctgcttcatgtgg |
| 375 | ggcggacttgaagaagt | 399 | acgtagccttcgggcat |
| 376 | agatggtgcgctcctgg | 400 | gccgtcgtccttgaaga |
| 377 | gcgcggtcttgtagtt | 401 | cctcgaacttcacctcg |
| 378 | gttcaccagggtgtcgc | 402 | cccttcagctcgatgcg |
| 379 | cctccttgaagtcgatg | 403 | ccccaggatgttgccgt |
| 380 | ttgtactccagcttgtg | 404 | cgttgtggctgttgtag |
| 381 | gtcggccatgatataga | 405 | atgccgttcttctgctt |
| 382 | tcttgaagttcaccttg | 406 | ctcgatgttgtggcgga |
| 383 | agctgcacgctgccgtc | 407 | tgctggtagtggtcggc |
| 384 | tcgccgatgggggtgtt | 408 | ttgtcggcagcagcac |
| 385 | gggtgctcaggtagtgg | 409 | tttgctcagggcggact |
| 386 | cgcttctcgttggggtc | 410 | gcaggaccatgtgatcg |
| 387 | ggcggtcacgaactcca | 411 | atgccgagagtgatccc |
| 388 | tcttgtacagctcgtcc | 412 | gaagccatggctaagct |
| 389 | tcctgctcctccacctc | 413 | tgggcagcgtgccatca |
| 390 | ctcctgggcacaagaca | 414 | tgacggtccatcccgct |
| 391 | agaagcacaggctgcag | 415 | tacacattgatcctagc |

HIV Gag RNA probes

| 416 | ttaatactgacgctctcgca | 440 | catttatctaactctcccccc |
|---|---|---|---|
| 417 | ccctggtcttaaccgaattt | 441 | ctgcttgcccatactatatg |
| 418 | aactgcgaatcgttctagct | 442 | atgtttctaacaggccagga |
| 419 | ccagtatttgtctacagcct | 443 | tgtctgaagggatggttgta |
| 420 | gagggtggctactgtattat | 444 | ctatcctttgatgcacacaa |
| 421 | gcttccttggtgtcttttac | 445 | gctcttcctctatcttctct |
| 422 | gctgtgccttttttcttactt | 446 | ttttttcctgtgtcagctgct |
| 423 | gtaattttggctgacctggt | 447 | cctggatgttctgcactata |
| 424 | atggcctgatgtaccatttg | 448 | ctgaaagccttctcttctac |
| 425 | gctccttctgataatgctga | 449 | ggtgtttaaatcttgtgggg |
| 426 | tttgcatggctgcttgatgt | 450 | cttcctcattgatggtctct |
| 427 | tgcaatctatcccattctgc | 451 | tcatctggcctggtgcaata |
| 428 | tatgtcacttcccccttggtt | 452 | gaagggtactagtagttcct |
| 429 | gtcatccatcctatttgttc | 453 | ctactgggataggtggatta |

TABLE 3-continued

Probe Sequences

| SEQ ID NO | | SEQ ID NO | |
|---|---|---|---|
| 430 | cccaggattatccatctttt | 454 | gtagggctatacatccttac |
| 431 | gtccttgtcttatgtccaga | 455 | catagtctctaaagggttcc |
| 432 | agagttttatagaaccggtc | 456 | tttacctcctgtgaagcttg |
| 433 | caacaaggtttctgtcatcc | 457 | aatctgggttcgcatttttgg |
| 434 | gctggtcccaatgcttttaa | 458 | ggcatgctgtcatcatttct |
| 435 | aaactcttgctttatggccg | 459 | tacttggctcattgcttcag |
| 436 | ctgcatcattatggtagctg | 460 | cccttctttgccacaattga |
| 437 | ggctctgcaattttggcta | 461 | tccaacagcccttttcccta |
| 438 | tttggtgtccttcctttcca | 462 | cctgtctctcagtacaatct |
| 439 | gggccagattttccctaaaa | 463 | aagaaaattccctggccttc |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method for detecting copies of at least one RNA expressed in individual mammalian cells, comprising
   (a) providing a sample containing a population of mammalian cells;
   (b) inducing gene expression in the mammalian cells ex vivo, either immediately or after culturing, by incubating the mammalian cells with at least one antigen that will bind specific receptors of the mammalian cells and initiate gene expression;
   (c) fixing and permeabilizing the mammalian cells;
   (d) labeling copies of a first target RNA expressed by the mammalian cells with a first set of 10-100 fluorescently labeled oligonucleotide hybridization probes each singly labeled with the same fluorescent moiety, and washing away unbound probes, wherein the first set of probes bind simultaneously to said first target RNA; and
   (e) detecting cells having expression events using flow cytometry (FC), an expression event being one or more fluorescence measurements of bound fluorescently labeled oligonucleotide hybridization probes categorized by fluorescence intensity gating,
      wherein the step of inducing comprises stimulating T-cell receptor (TCR) signaling and down-stream gene expression by antigen presenting cells (APCs) that are present in the cell population or by an artificial APC (aAPC).

2. The method of claim 1 wherein stimulation by APC or aAPC induction is for a period selected from the group consisting of from 30 minutes to 6 hours, from 6 to 24 hours, and from 24 to 72 hours.

3. The method of claim 1 wherein the step of inducing includes co-stimulating with at least one monoclonal antibody (mAb).

4. The method of claim 1, wherein the step of inducing includes co-stimulating with at least one monoclonal antibody (mAb) that is bound to the aAPC.

5. The method of claim 1 wherein the antigen is derived from a microorganism.

6. The method of claim 1 wherein the antigen comprises a peptide or mixture of peptides.

7. The method of claim 1 wherein a peptide or mixture of peptides that associate with MHC class I or MHC class II molecules is added to the APC or aAPC.

8. The method of claim 7, wherein the peptide or peptide mixture is present at a concentration between 1-20 µg/ml.

9. The method of claim 1 wherein the at least one RNA is encoded by a cytokine gene.

10. The method of claim 9 wherein the gene encodes IL-2, TNFα, or IFNγ.

11. The method of claim 1 wherein the antigen is a *M. tuberculosis*-derived immunogenic peptide.

12. The method of claim 1 wherein the probe set comprises 20-60 probes that bind simultaneously to the at least one RNA molecule.

13. The method of claim 1 wherein the cell population comprises T cells obtained from human PBMCs, the at least one RNA molecule is encoded by a cytokine gene, cells in the cell population are induced by aAPC with one or more peptide-loaded MHC molecules that interact with TCR, and the probe set comprises 20-60 probes.

14. The method of claim 1, wherein at least one detected cell having expression events is separated from cells not having expression events by fluorescence-activated cell sorting.

15. The method of claim 14, wherein gene expression is measured in the separated cells.

16. The method of claim 15, wherein measurement of gene expression is accomplished by RT-PCR or a transcriptomic analysis of RNA in the cells.

17. The method of claim 1 wherein the step of inducing comprises stimulating toll-like receptor signaling and down-stream gene expression with a microbial product or a synthetic compound, wherein the microbial product is a lipid, glycan, glycolipid, sulfolipid, glycoprotein, protein, peptide, or nucleic acid and wherein the stimulus is present at a concentration between 1-100 ng/ml, 100-1000 ng/ml, or 1-20 µg/ml.

18. The method of claim 17, wherein stimulation is for a period selected from the group consisting of from 30 minutes to 6 hours, from 6 to 24 hours, and from 24 to 72 hours.

19. The method of claim 1, wherein the antigen is a cytokine.

20. The method of claim 19, wherein the cytokine is one selected from the group consisting of IFNγ, IL-2, IL-15 and TNFα.

21. The method of claim 1 wherein more than one antigen or stimulus is provided.

22. The method of claim 21 wherein different stimuli are provided at different times.

23. The method of claim 1, wherein the receptors are selected from the group consisting of toll-like receptors, NOD and NOD-Like receptors, G protein coupled receptors, polypeptide hormone receptors, cytokine receptors, B cell receptors, and T cell receptors.

24. The method of claim 1, wherein the population comprises cells selected from the group consisting of PBMCs, T-cells, lymphocytes, $CD3^+CD4^+$ T cells (T helper 1 or Th1 cells), $CD3^+CD4^+$ T cells (T helper 2 or Th2 cells), $CD3^+CD8^+$ T cells, Th17, Treg cells, NK cells, NKT cells, macrophages, dendritic cells, cells of endothelia and epithelia of various body organs, and cells of the nervous system.

25. The method of claim 1, wherein the probes are 15-25 nucleotides long.

26. The method of claim 1, further comprising
labeling copies of a second target RNA expressed by the mammalian cells with a second set of fluorescently labeled oligonucleotide hybridization probes each singly labeled with a same second fluorescent moiety that is different from the first fluorescent moiety, and
washing away unbound probes,
wherein the second set of probes bind simultaneously to said second target RNA, said second target RNA being different from said first target RNA.

27. The method of claim 26, further comprising
labeling copies of a third target RNA expressed by the mammalian cells with a third set of fluorescently labeled oligonucleotide hybridization probes each singly labeled with a same third fluorescent moiety that is different from the first fluorescent moiety and the second fluorescent moiety, and
washing away unbound probes,
wherein the third set of probes bind simultaneously to said third target RNA, said third target RNA being different from said first target RNA and said second target RNA.

28. A method for detecting copies of at least one RNA molecule expressed in individual mammalian cells, comprising
(a) providing a sample containing a population of mammalian cells;
(b) fixing and permeabilizing the mammalian cells;
(c) labeling copies of a first target RNA expressed by the mammalian cells with a first set of 10-100 fluorescently labeled oligonucleotide hybridization probes each singly labeled with the same fluorescent moiety, and washing away unbound probes, wherein the first set of probes bind simultaneously to said first target RNA; and
(d) detecting cells having expression events using FC, an expression event being one or more fluorescence measurements of bound fluorescently labeled oligonucleotide hybridization probes categorized by fluorescence intensity gating.

29. A method for analysis of gene expression in mammalian cells present in a population comprising T cells by detecting copies of at least one RNA expressed in individual mammalian cells, comprising
(a) providing a sample containing a population of mammalian cells comprising T-cells;
(b) inducing gene expression in the mammalian cells ex vivo, either immediately or after culturing, by incubating the mammalian cells with at least one compound that will bind specific receptors of the mammalian cells and initiate gene expression;
(c) fixing and permeabilizing the mammalian cells;
(d) labeling copies of a first target RNA expressed by the mammalian cells with a first set of fluorescently labeled oligonucleotide hybridization probes each singly labeled with the same fluorescent moiety, and washing away unbound probes, wherein the first set of probes bind simultaneously to said first target RNA; and
(e) detecting cells having expression events using FC, an expression event being one or more fluorescence measurements of bound fluorescently labeled oligonucleotide hybridization probes categorized by fluorescence intensity gating,
wherein the step of inducing comprises stimulating T-cell receptor signaling and down-stream gene expression by antigen presenting cells that are present in the cell population or by an artificial APC.

30. The method of claim 29, wherein the population comprises cells selected from the group consisting of PBMCs, T-cells, lymphocytes, $CD3^+CD4^+$ T cells (T helper 1 or Th1 cells), $CD3^+CD4^+$ T cells (T helper 2 or Th2 cells), $CD3^+CD8^+$ T cells, Th17, Treg cells, NK cells, NKT cells, macrophages, dendritic cells, cells of endothelia and epithelia of various body organs, and cells of the nervous system.

* * * * *

SEQUENCE LISTING

```
<160> NUMBER OF SEQ ID NOS: 463

<210> SEQ ID NO 1
<211> LENGTH: 10
<212> TYPE: PRT
<213> ORGANISM: Homo sapiens

<400> SEQUENCE: 1

Phe Ile Tyr Ala Gly Ser Leu Ser Ala Leu
1               5                   10

<210> SEQ ID NO 2
<211> LENGTH: 9
<212> TYPE: PRT
<213> ORGANISM: Homo sapiens

<400> SEQUENCE: 2

Lys Leu Val Ala Asn Asn Thr Arg Leu
1               5

<210> SEQ ID NO 3
<211> LENGTH: 9
<212> TYPE: PRT
<213> ORGANISM: Homo sapiens

<400> SEQUENCE: 3

Gly Leu Ala Gly Gly Ala Ala Thr Ala
1               5

<210> SEQ ID NO 4
<211> LENGTH: 15
<212> TYPE: PRT
<213> ORGANISM: Homo sapiens

<400> SEQUENCE: 4

Pro Val Glu Tyr Leu Gln Tyr Pro Ser Pro Ser Met Gly Arg Asp
1               5                   10                  15

<210> SEQ ID NO 5
<211> LENGTH: 15
<212> TYPE: PRT
<213> ORGANISM: Homo sapiens
```

<400> SEQUENCE: 5

Leu Pro Val Glu Tyr Leu Gln Val Pro Ser Pro Ser Met Gly Arg
1               5                   10                  15

<210> SEQ ID NO 6
<211> LENGTH: 15
<212> TYPE: PRT
<213> ORGANISM: Homo sapiens

<400> SEQUENCE: 6

Pro Gln Gln Phe Ile Tyr Ala Gly Ser Leu Ser Ala Leu Leu Asp
1               5                   10                  15

<210> SEQ ID NO 7
<211> LENGTH: 8
<212> TYPE: PRT
<213> ORGANISM: Homo sapiens

<400> SEQUENCE: 7

Ala Leu Gly Ile Ser Leu Thr Val
1               5

<210> SEQ ID NO 8
<211> LENGTH: 10
<212> TYPE: PRT
<213> ORGANISM: Homo sapiens

<400> SEQUENCE: 8

Phe Leu Ala Cys Phe Thr Leu Ile Ala Ala
1               5                   10

<210> SEQ ID NO 9
<211> LENGTH: 9
<212> TYPE: PRT
<213> ORGANISM: Homo sapiens

<400> SEQUENCE: 9

Phe Leu Ile Gly Tyr Gly Leu Leu Ala
1               5

<210> SEQ ID NO 10
<211> LENGTH: 15
<212> TYPE: PRT
<213> ORGANISM: Homo sapiens

<400> SEQUENCE: 10

Ala Gly Arg Leu Arg Gly Leu Phe Thr Asn Pro Gly Ser Trp Arg
1               5                   10                  15

<210> SEQ ID NO 11
<211> LENGTH: 15
<212> TYPE: PRT
<213> ORGANISM: Homo sapiens

<400> SEQUENCE: 11

Val Gly Phe Leu Ala Cys Phe Thr Leu Ile Ala Ala Ile Gly Ala
1               5                   10                  15

<210> SEQ ID NO 12
<211> LENGTH: 15
<212> TYPE: PRT
<213> ORGANISM: Homo sapiens

<400> SEQUENCE: 12

```
Leu Asp Thr Val Val Leu Leu Gly Ala Leu Ala Asn Glu His Ser
1               5                   10                  15
```

<210> SEQ ID NO 13
<211> LENGTH: 9
<212> TYPE: PRT
<213> ORGANISM: Homo sapiens

<400> SEQUENCE: 13

```
Gly Leu Leu His His Ala Pro Ser Leu
1               5
```

<210> SEQ ID NO 14
<211> LENGTH: 9
<212> TYPE: PRT
<213> ORGANISM: Homo sapiens

<400> SEQUENCE: 14

```
Ser Leu Trp Lys Asp Gly Ala Pro Leu
1               5
```

<210> SEQ ID NO 15
<211> LENGTH: 11
<212> TYPE: PRT
<213> ORGANISM: Homo sapiens

<400> SEQUENCE: 15

```
Arg Lys Ala Ala Gly Arg Pro Asp Leu Arg Val
1               5                   10
```

<210> SEQ ID NO 16
<211> LENGTH: 9
<212> TYPE: PRT
<213> ORGANISM: Homo sapiens

<400> SEQUENCE: 16

```
Lys Leu Leu Asp Asn His Ile Leu Ala
1               5
```

<210> SEQ ID NO 17
<211> LENGTH: 9
<212> TYPE: PRT
<213> ORGANISM: Homo sapiens

<400> SEQUENCE: 17

```
Phe Val Leu Met Ala Ala Trp Leu Ala
1               5
```

<210> SEQ ID NO 18
<211> LENGTH: 15
<212> TYPE: PRT
<213> ORGANISM: Homo sapiens

<400> SEQUENCE: 18

```
Pro Asp Pro Tyr Gln Ala Phe Val Leu Met Ala Ala Trp Leu Ala
1               5                   10                  15
```

<210> SEQ ID NO 19
<211> LENGTH: 15
<212> TYPE: PRT
<213> ORGANISM: Homo sapiens

<400> SEQUENCE: 19

Thr Met Arg Ala His Ser Tyr Ser Leu Leu Arg Ala Ile Met Gln

-continued

```
                1               5                  10                 15
```

```
<210> SEQ ID NO 20
<211> LENGTH: 15
<212> TYPE: PRT
<213> ORGANISM: Homo sapiens

<400> SEQUENCE: 20

Arg Ala His Tyr Arg Lys Leu Leu Asp Asn His Ile Leu Ala Thr
1               5                  10                 15

<210> SEQ ID NO 21
<211> LENGTH: 10
<212> TYPE: PRT
<213> ORGANISM: Homo sapiens

<400> SEQUENCE: 21

Val Leu Met Gly Gly Val Pro Gly Val Glu
1               5                  10

<210> SEQ ID NO 22
<211> LENGTH: 9
<212> TYPE: PRT
<213> ORGANISM: Homo sapiens

<400> SEQUENCE: 22

Leu Leu Asp Ser Gly Thr Thr Ser Ile
1               5

<210> SEQ ID NO 23
<211> LENGTH: 11
<212> TYPE: PRT
<213> ORGANISM: Homo sapiens

<400> SEQUENCE: 23

Ala Arg Val Glu Ala Gly Glu Glu Leu Gly Val
1               5                  10

<210> SEQ ID NO 24
<211> LENGTH: 11
<212> TYPE: PRT
<213> ORGANISM: Homo sapiens

<400> SEQUENCE: 24

Ala Leu Ile Glu Ser Gly Val Leu Ile Pro Ala
1               5                  10

<210> SEQ ID NO 25
<211> LENGTH: 9
<212> TYPE: PRT
<213> ORGANISM: Homo sapiens

<400> SEQUENCE: 25

Arg Leu Val Ala Arg Leu Ile Pro Val
1               5

<210> SEQ ID NO 26
<211> LENGTH: 15
<212> TYPE: PRT
<213> ORGANISM: Homo sapiens

<400> SEQUENCE: 26

Ala Ile Gly Ile Arg Glu Leu Arg Gln His Ala Ser Arg Tyr Leu
1               5                  10                 15
```

<210> SEQ ID NO 27
<211> LENGTH: 15
<212> TYPE: PRT
<213> ORGANISM: Homo sapiens

<400> SEQUENCE: 27

Arg Leu Val Ala Arg Leu Ile Pro Val Gln Ala Ala Glu Arg Ser
1               5                   10                  15

<210> SEQ ID NO 28
<211> LENGTH: 15
<212> TYPE: PRT
<213> ORGANISM: Homo sapiens

<400> SEQUENCE: 28

Lys Arg Thr Leu Ser Asp Val Leu Asn Glu Met Arg Asp Glu Gln
1               5                   10                  15

<210> SEQ ID NO 29
<211> LENGTH: 11
<212> TYPE: PRT
<213> ORGANISM: Homo sapiens

<400> SEQUENCE: 29

Ser Gly Asp Leu Lys Thr Gln Ile Asp Gln Val
1               5                   10

<210> SEQ ID NO 30
<211> LENGTH: 10
<212> TYPE: PRT
<213> ORGANISM: Homo sapiens

<400> SEQUENCE: 30

Ile Arg Gln Ala Gly Val Gln Tyr Ser Arg
1               5                   10

<210> SEQ ID NO 31
<211> LENGTH: 9
<212> TYPE: PRT
<213> ORGANISM: Homo sapiens

<400> SEQUENCE: 31

Glu Ile Ser Thr Asn Ile Arg Gln Ala
1               5

<210> SEQ ID NO 32
<211> LENGTH: 9
<212> TYPE: PRT
<213> ORGANISM: Homo sapiens

<400> SEQUENCE: 32

Ala Met Ala Ser Thr Glu Gly Asn Val
1               5

<210> SEQ ID NO 33
<211> LENGTH: 9
<212> TYPE: PRT
<213> ORGANISM: Homo sapiens

<400> SEQUENCE: 33

Leu Leu Asp Glu Gly Lys Gln Ser Leu
1               5

<210> SEQ ID NO 34

```
<211> LENGTH: 15
<212> TYPE: PRT
<213> ORGANISM: Homo sapiens

<400> SEQUENCE: 34

Phe Ala Gly Ile Glu Ala Ala Ala Ser Ala Ile Gln Gly Asn Val
1               5                   10                  15

<210> SEQ ID NO 35
<211> LENGTH: 15
<212> TYPE: PRT
<213> ORGANISM: Homo sapiens

<400> SEQUENCE: 35

Ser Ala Ile Gln Gly Asn Val Thr Ser Ile His Ser Leu Leu Asp
1               5                   10                  15

<210> SEQ ID NO 36
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 36
gagcatccaa aagagtgtgg ag                                              22

<210> SEQ ID NO 37
<211> LENGTH: 22
<212> TYPE: DNA
<213> ORGANISM: Artificial
<220> FEATURE:
<223> OTHER INFORMATION: Synthetic Sequence

<400> SEQUENCE: 37
ttcatgtatt gctttgcgtt gg                                              22

<210> SEQ ID NO 38
<211> LENGTH: 22
<212> TYPE: DNA
<213> ORGANISM: Artificial
<220> FEATURE:
<223> OTHER INFORMATION: Synthetic Sequence

<400> SEQUENCE: 38
ccaatatgat tccacccatg gc                                              22

<210> SEQ ID NO 39
<211> LENGTH: 22
<212> TYPE: DNA
<213> ORGANISM: Artificial
<220> FEATURE:
<223> OTHER INFORMATION: Synthetic Sequence

<400> SEQUENCE: 39
tcctggaaga tggtgatggg at                                              22

<210> SEQ ID NO 40
<211> LENGTH: 20
<212> TYPE: DNA
<213> ORGANISM: Artificial
<220> FEATURE:
<223> OTHER INFORMATION: Synthetic Sequence

<400> SEQUENCE: 40
atcagaacaa tgtgctgcac                                                 20
```

<210> SEQ ID NO 41
<211> LENGTH: 20
<212> TYPE: DNA
<213> ORGANISM: Artificial
<220> FEATURE:
<223> OTHER INFORMATION: Synthetic Sequence

<400> SEQUENCE: 41
ccaaaggact taactgatct                                                    20

<210> SEQ ID NO 42
<211> LENGTH: 20
<212> TYPE: DNA
<213> ORGANISM: Artificial
<220> FEATURE:
<223> OTHER INFORMATION: Synthetic Sequence

<400> SEQUENCE: 42
gccaaagaag ttgaaatcag                                                    20

<210> SEQ ID NO 43
<211> LENGTH: 20
<212> TYPE: DNA
<213> ORGANISM: Artificial
<220> FEATURE:
<223> OTHER INFORMATION: Synthetic Sequence

<400> SEQUENCE: 43
gagctgaaaa gccaagatat                                                    20

<210> SEQ ID NO 44
<211> LENGTH: 20
<212> TYPE: DNA
<213> ORGANISM: Artificial
<220> FEATURE:
<223> OTHER INFORMATION: Synthetic Sequence

<400> SEQUENCE: 44
tatgggtcct ggcagtaaca                                                    20

<210> SEQ ID NO 45
<211> LENGTH: 20
<212> TYPE: DNA
<213> ORGANISM: Artificial
<220> FEATURE:
<223> OTHER INFORMATION: Synthetic Sequence

<400> SEQUENCE: 45
gacctgcatt aaaatatttc                                                    20

<210> SEQ ID NO 46
<211> LENGTH: 20
<212> TYPE: DNA
<213> ORGANISM: Artificial
<220> FEATURE:
<223> OTHER INFORMATION: Synthetic Sequence

<400> SEQUENCE: 46
caaaatgcct aagaaaagag                                                    20

<210> SEQ ID NO 47
<211> LENGTH: 20
<212> TYPE: DNA
<213> ORGANISM: Artificial
<220> FEATURE:

<223> OTHER INFORMATION: Synthetic Sequence

<400> SEQUENCE: 47
tggctctgca ttattttct                                              20

<210> SEQ ID NO 48
<211> LENGTH: 20
<212> TYPE: DNA
<213> ORGANISM: Artificial
<220> FEATURE:
<223> OTHER INFORMATION: Synthetic Sequence

<400> SEQUENCE: 48
gctctggtca tctttaaagt                                             20

<210> SEQ ID NO 49
<211> LENGTH: 20
<212> TYPE: DNA
<213> ORGANISM: Artificial
<220> FEATURE:
<223> OTHER INFORMATION: Synthetic Sequence

<400> SEQUENCE: 49
cttgacattc atgtcttcct                                             20

<210> SEQ ID NO 50
<211> LENGTH: 20
<212> TYPE: DNA
<213> ORGANISM: Artificial
<220> FEATURE:
<223> OTHER INFORMATION: Synthetic Sequence

<400> SEQUENCE: 50
ttagtcagct tttcgaagtc                                             20

<210> SEQ ID NO 51
<211> LENGTH: 20
<212> TYPE: DNA
<213> ORGANISM: Artificial
<220> FEATURE:
<223> OTHER INFORMATION: Synthetic Sequence

<400> SEQUENCE: 51
gttcatgtat tgctttgcgt                                             20

<210> SEQ ID NO 52
<211> LENGTH: 20
<212> TYPE: DNA
<213> ORGANISM: Artificial
<220> FEATURE:
<223> OTHER INFORMATION: Synthetic Sequence

<400> SEQUENCE: 52
ttcgcttccc tgttttagct                                             20

<210> SEQ ID NO 53
<211> LENGTH: 20
<212> TYPE: DNA
<213> ORGANISM: Artificial
<220> FEATURE:
<223> OTHER INFORMATION: Synthetic Sequence

<400> SEQUENCE: 53
attactggga tgctcttcga                                             20

<210> SEQ ID NO 54
<211> LENGTH: 20
<212> TYPE: DNA
<213> ORGANISM: Artificial
<220> FEATURE:
<223> OTHER INFORMATION: Synthetic Sequence

<400> SEQUENCE: 54
ccccatataa ataatgttaa                                              20

<210> SEQ ID NO 55
<211> LENGTH: 20
<212> TYPE: DNA
<213> ORGANISM: Artificial
<220> FEATURE:
<223> OTHER INFORMATION: Synthetic Sequence

<400> SEQUENCE: 55
cattacacaa aagttgctat                                              20

<210> SEQ ID NO 56
<211> LENGTH: 20
<212> TYPE: DNA
<213> ORGANISM: Artificial
<220> FEATURE:
<223> OTHER INFORMATION: Synthetic Sequence

<400> SEQUENCE: 56
cagaaaacaa aggattaagt                                              20

<210> SEQ ID NO 57
<211> LENGTH: 20
<212> TYPE: DNA
<213> ORGANISM: Artificial
<220> FEATURE:
<223> OTHER INFORMATION: Synthetic Sequence

<400> SEQUENCE: 57
ccctgagata aagccttgta                                              20

<210> SEQ ID NO 58
<211> LENGTH: 20
<212> TYPE: DNA
<213> ORGANISM: Artificial
<220> FEATURE:
<223> OTHER INFORMATION: Synthetic Sequence

<400> SEQUENCE: 58
aaacacacaa cccatgggat                                              20

<210> SEQ ID NO 59
<211> LENGTH: 20
<212> TYPE: DNA
<213> ORGANISM: Artificial
<220> FEATURE:
<223> OTHER INFORMATION: Synthetic Sequence

<400> SEQUENCE: 59
ctggatagta tcacttcact                                              20

<210> SEQ ID NO 60
<211> LENGTH: 20
<212> TYPE: DNA
<213> ORGANISM: Artificial
<220> FEATURE:
<223> OTHER INFORMATION: Synthetic Sequence

<400> SEQUENCE: 60
aagcactggc tcagattgca						20

<210> SEQ ID NO 61
<211> LENGTH: 20
<212> TYPE: DNA
<213> ORGANISM: Artificial
<220> FEATURE:
<223> OTHER INFORMATION: Synthetic Sequence

<400> SEQUENCE: 61
tcagggtcac ctgacacatt						20

<210> SEQ ID NO 62
<211> LENGTH: 20
<212> TYPE: DNA
<213> ORGANISM: Artificial
<220> FEATURE:
<223> OTHER INFORMATION: Synthetic Sequence

<400> SEQUENCE: 62
ttggaagcac caggcatgaa						20

<210> SEQ ID NO 63
<211> LENGTH: 20
<212> TYPE: DNA
<213> ORGANISM: Artificial
<220> FEATURE:
<223> OTHER INFORMATION: Synthetic Sequence

<400> SEQUENCE: 63
tgagttactt tccatttggg						20

<210> SEQ ID NO 64
<211> LENGTH: 20
<212> TYPE: DNA
<213> ORGANISM: Artificial
<220> FEATURE:
<223> OTHER INFORMATION: Synthetic Sequence

<400> SEQUENCE: 64
tctaatagct gatcttcaga						20

<210> SEQ ID NO 65
<211> LENGTH: 20
<212> TYPE: DNA
<213> ORGANISM: Artificial
<220> FEATURE:
<223> OTHER INFORMATION: Synthetic Sequence

<400> SEQUENCE: 65
tcttgtatca agctgatcag						20

<210> SEQ ID NO 66
<211> LENGTH: 20
<212> TYPE: DNA
<213> ORGANISM: Artificial
<220> FEATURE:
<223> OTHER INFORMATION: Synthetic Sequence

<400> SEQUENCE: 66
tcatcgtttc cgagagaatt						20

<210> SEQ ID NO 67
<211> LENGTH: 20

```
<212> TYPE: DNA
<213> ORGANISM: Artificial
<220> FEATURE:
<223> OTHER INFORMATION: Synthetic Sequence

<400> SEQUENCE: 67
caagagaacc caaaacgatg                                               20

<210> SEQ ID NO 68
<211> LENGTH: 20
<212> TYPE: DNA
<213> ORGANISM: Artificial
<220> FEATURE:
<223> OTHER INFORMATION: Synthetic Sequence

<400> SEQUENCE: 68
aaggttttct gcttcttta                                                20

<210> SEQ ID NO 69
<211> LENGTH: 20
<212> TYPE: DNA
<213> ORGANISM: Artificial
<220> FEATURE:
<223> OTHER INFORMATION: Synthetic Sequence

<400> SEQUENCE: 69
ccattatccg ctacatctga                                               20

<210> SEQ ID NO 70
<211> LENGTH: 20
<212> TYPE: DNA
<213> ORGANISM: Artificial
<220> FEATURE:
<223> OTHER INFORMATION: Synthetic Sequence

<400> SEQUENCE: 70
cactctcctc tttccaattc                                               20

<210> SEQ ID NO 71
<211> LENGTH: 20
<212> TYPE: DNA
<213> ORGANISM: Artificial
<220> FEATURE:
<223> OTHER INFORMATION: Synthetic Sequence

<400> SEQUENCE: 71
gtttgaagta aaaggagaca                                               20

<210> SEQ ID NO 72
<211> LENGTH: 20
<212> TYPE: DNA
<213> ORGANISM: Artificial
<220> FEATURE:
<223> OTHER INFORMATION: Synthetic Sequence

<400> SEQUENCE: 72
atggtctcca cactcttttg                                               20

<210> SEQ ID NO 73
<211> LENGTH: 20
<212> TYPE: DNA
<213> ORGANISM: Artificial
<220> FEATURE:
<223> OTHER INFORMATION: Synthetic Sequence

<400> SEQUENCE: 73
```
ctcgtttctt tttgttgcta                                              20

<210> SEQ ID NO 74
<211> LENGTH: 20
<212> TYPE: DNA
<213> ORGANISM: Artificial
<220> FEATURE:
<223> OTHER INFORMATION: Synthetic Sequence

<400> SEQUENCE: 74
gacattcaag tcagttaccg                                              20

<210> SEQ ID NO 75
<211> LENGTH: 20
<212> TYPE: DNA
<213> ORGANISM: Artificial
<220> FEATURE:
<223> OTHER INFORMATION: Synthetic Sequence

<400> SEQUENCE: 75
agttcagcca tcacttggat                                              20

<210> SEQ ID NO 76
<211> LENGTH: 20
<212> TYPE: DNA
<213> ORGANISM: Artificial
<220> FEATURE:
<223> OTHER INFORMATION: Synthetic Sequence

<400> SEQUENCE: 76
cgaaacagca tctgactcct                                              20

<210> SEQ ID NO 77
<211> LENGTH: 20
<212> TYPE: DNA
<213> ORGANISM: Artificial
<220> FEATURE:
<223> OTHER INFORMATION: Synthetic Sequence

<400> SEQUENCE: 77
caaatattgc aggcaggaca                                              20

<210> SEQ ID NO 78
<211> LENGTH: 20
<212> TYPE: DNA
<213> ORGANISM: Artificial
<220> FEATURE:
<223> OTHER INFORMATION: Synthetic Sequence

<400> SEQUENCE: 78
cttatttgat tgatgagtct                                              20

<210> SEQ ID NO 79
<211> LENGTH: 20
<212> TYPE: DNA
<213> ORGANISM: Artificial
<220> FEATURE:
<223> OTHER INFORMATION: Synthetic Sequence

<400> SEQUENCE: 79
gacagtcaca ggatatagga                                              20

<210> SEQ ID NO 80
<211> LENGTH: 20
<212> TYPE: DNA
<213> ORGANISM: Artificial

<220> FEATURE:
<223> OTHER INFORMATION: Synthetic Sequence

<400> SEQUENCE: 80
cacatagcct tgcctaatta                                               20

<210> SEQ ID NO 81
<211> LENGTH: 20
<212> TYPE: DNA
<213> ORGANISM: Artificial
<220> FEATURE:
<223> OTHER INFORMATION: Synthetic Sequence

<400> SEQUENCE: 81
ttaggttggc tgcctagttg                                               20

<210> SEQ ID NO 82
<211> LENGTH: 20
<212> TYPE: DNA
<213> ORGANISM: Artificial
<220> FEATURE:
<223> OTHER INFORMATION: Synthetic Sequence

<400> SEQUENCE: 82
gttcattgta tcatcaagtg                                               20

<210> SEQ ID NO 83
<211> LENGTH: 20
<212> TYPE: DNA
<213> ORGANISM: Artificial
<220> FEATURE:
<223> OTHER INFORMATION: Synthetic Sequence

<400> SEQUENCE: 83
catattttca aaccggcagt                                               20

<210> SEQ ID NO 84
<211> LENGTH: 20
<212> TYPE: DNA
<213> ORGANISM: Artificial
<220> FEATURE:
<223> OTHER INFORMATION: Synthetic Sequence

<400> SEQUENCE: 84
agttctgtct gacatgccat                                               20

<210> SEQ ID NO 85
<211> LENGTH: 20
<212> TYPE: DNA
<213> ORGANISM: Artificial
<220> FEATURE:
<223> OTHER INFORMATION: Synthetic Sequence

<400> SEQUENCE: 85
ctcctgagat gctatgtttt                                               20

<210> SEQ ID NO 86
<211> LENGTH: 20
<212> TYPE: DNA
<213> ORGANISM: Artificial
<220> FEATURE:
<223> OTHER INFORMATION: Synthetic Sequence

<400> SEQUENCE: 86
cagtcacagt tgtcaacaat                                               20

<210> SEQ ID NO 87
<211> LENGTH: 20
<212> TYPE: DNA
<213> ORGANISM: Artificial
<220> FEATURE:
<223> OTHER INFORMATION: Synthetic Sequence

<400> SEQUENCE: 87
gtgaacttac actttattca                                              20

<210> SEQ ID NO 88
<211> LENGTH: 20
<212> TYPE: DNA
<213> ORGANISM: Artificial
<220> FEATURE:
<223> OTHER INFORMATION: Synthetic Sequence

<400> SEQUENCE: 88
tagcccacac ttaggtgata                                              20

<210> SEQ ID NO 89
<211> LENGTH: 20
<212> TYPE: DNA
<213> ORGANISM: Artificial
<220> FEATURE:
<223> OTHER INFORMATION: Synthetic Sequence

<400> SEQUENCE: 89
agactgactg aatggatgta                                              20

<210> SEQ ID NO 90
<211> LENGTH: 20
<212> TYPE: DNA
<213> ORGANISM: Artificial
<220> FEATURE:
<223> OTHER INFORMATION: Synthetic Sequence

<400> SEQUENCE: 90
ttcctcttct gatgactctt                                              20

<210> SEQ ID NO 91
<211> LENGTH: 20
<212> TYPE: DNA
<213> ORGANISM: Artificial
<220> FEATURE:
<223> OTHER INFORMATION: Synthetic Sequence

<400> SEQUENCE: 91
tttcaaagac tttacctgtc                                              20

<210> SEQ ID NO 92
<211> LENGTH: 20
<212> TYPE: DNA
<213> ORGANISM: Artificial
<220> FEATURE:
<223> OTHER INFORMATION: Synthetic Sequence

<400> SEQUENCE: 92
aatattatgg gggtgtcaaa                                              20

<210> SEQ ID NO 93
<211> LENGTH: 20
<212> TYPE: DNA
<213> ORGANISM: Artificial
<220> FEATURE:
<223> OTHER INFORMATION: Synthetic Sequence

```
<400> SEQUENCE: 93
ctcttgaaca agagatgcaa                                              20

<210> SEQ ID NO 94
<211> LENGTH: 20
<212> TYPE: DNA
<213> ORGANISM: Artificial
<220> FEATURE:
<223> OTHER INFORMATION: Synthetic Sequence

<400> SEQUENCE: 94
ttgaggttac tgtgagtagt                                              20

<210> SEQ ID NO 95
<211> LENGTH: 20
<212> TYPE: DNA
<213> ORGANISM: Artificial
<220> FEATURE:
<223> OTHER INFORMATION: Synthetic Sequence

<400> SEQUENCE: 95
caatgcaaga caggagttgc                                              20

<210> SEQ ID NO 96
<211> LENGTH: 20
<212> TYPE: DNA
<213> ORGANISM: Artificial
<220> FEATURE:
<223> OTHER INFORMATION: Synthetic Sequence

<400> SEQUENCE: 96
ttgaagtagg tgcactgttt                                              20

<210> SEQ ID NO 97
<211> LENGTH: 20
<212> TYPE: DNA
<213> ORGANISM: Artificial
<220> FEATURE:
<223> OTHER INFORMATION: Synthetic Sequence

<400> SEQUENCE: 97
gcagtaaatg ctccagttgt                                              20

<210> SEQ ID NO 98
<211> LENGTH: 20
<212> TYPE: DNA
<213> ORGANISM: Artificial
<220> FEATURE:
<223> OTHER INFORMATION: Synthetic Sequence

<400> SEQUENCE: 98
tcttgtaatt attaattcca                                              20

<210> SEQ ID NO 99
<211> LENGTH: 20
<212> TYPE: DNA
<213> ORGANISM: Artificial
<220> FEATURE:
<223> OTHER INFORMATION: Synthetic Sequence

<400> SEQUENCE: 99
gcatgtaaaa cttaaatgtg                                              20

<210> SEQ ID NO 100
```

```
<211> LENGTH: 20
<212> TYPE: DNA
<213> ORGANISM: Artificial
<220> FEATURE:
<223> OTHER INFORMATION: Synthetic Sequence

<400> SEQUENCE: 100
cttctagaca ctgaagatgt                                              20

<210> SEQ ID NO 101
<211> LENGTH: 20
<212> TYPE: DNA
<213> ORGANISM: Artificial
<220> FEATURE:
<223> OTHER INFORMATION: Synthetic Sequence

<400> SEQUENCE: 101
tttgagctaa atttagcact                                              20

<210> SEQ ID NO 102
<211> LENGTH: 20
<212> TYPE: DNA
<213> ORGANISM: Artificial
<220> FEATURE:
<223> OTHER INFORMATION: Synthetic Sequence

<400> SEQUENCE: 102
tattgctgat taagtccctg                                              20

<210> SEQ ID NO 103
<211> LENGTH: 20
<212> TYPE: DNA
<213> ORGANISM: Artificial
<220> FEATURE:
<223> OTHER INFORMATION: Synthetic Sequence

<400> SEQUENCE: 103
atgttgtttc agatcccttt                                              20

<210> SEQ ID NO 104
<211> LENGTH: 20
<212> TYPE: DNA
<213> ORGANISM: Artificial
<220> FEATURE:
<223> OTHER INFORMATION: Synthetic Sequence

<400> SEQUENCE: 104
attctacaat ggttgctgtc                                              20

<210> SEQ ID NO 105
<211> LENGTH: 20
<212> TYPE: DNA
<213> ORGANISM: Artificial
<220> FEATURE:
<223> OTHER INFORMATION: Synthetic Sequence

<400> SEQUENCE: 105
gttgagatga tgctttgaca                                              20

<210> SEQ ID NO 106
<211> LENGTH: 20
<212> TYPE: DNA
<213> ORGANISM: Artificial
<220> FEATURE:
<223> OTHER INFORMATION: Synthetic Sequence

<400> SEQUENCE: 106
```
ctgatatgtt ttaagtggga                                              20

<210> SEQ ID NO 107
<211> LENGTH: 20
<212> TYPE: DNA
<213> ORGANISM: Artificial
<220> FEATURE:
<223> OTHER INFORMATION: Synthetic Sequence

<400> SEQUENCE: 107
caacaataaa tataaaattt                                              20

<210> SEQ ID NO 108
<211> LENGTH: 20
<212> TYPE: DNA
<213> ORGANISM: Artificial
<220> FEATURE:
<223> OTHER INFORMATION: Synthetic Sequence

<400> SEQUENCE: 108
agattaagaa taatagttac                                              20

<210> SEQ ID NO 109
<211> LENGTH: 20
<212> TYPE: DNA
<213> ORGANISM: Artificial
<220> FEATURE:
<223> OTHER INFORMATION: Synthetic Sequence

<400> SEQUENCE: 109
gggcttacaa aaagaatcat                                              20

<210> SEQ ID NO 110
<211> LENGTH: 20
<212> TYPE: DNA
<213> ORGANISM: Artificial
<220> FEATURE:
<223> OTHER INFORMATION: Synthetic Sequence

<400> SEQUENCE: 110
aatattttgg gataaataag                                              20

<210> SEQ ID NO 111
<211> LENGTH: 20
<212> TYPE: DNA
<213> ORGANISM: Artificial
<220> FEATURE:
<223> OTHER INFORMATION: Synthetic Sequence

<400> SEQUENCE: 111
actaaccaat ctacatagat                                              20

<210> SEQ ID NO 112
<211> LENGTH: 20
<212> TYPE: DNA
<213> ORGANISM: Artificial
<220> FEATURE:
<223> OTHER INFORMATION: Synthetic Sequence

<400> SEQUENCE: 112
gtgaaatccc tctttgttac                                              20

<210> SEQ ID NO 113
<211> LENGTH: 20
<212> TYPE: DNA

<213> ORGANISM: Artificial
<220> FEATURE:
<223> OTHER INFORMATION: Synthetic Sequence

<400> SEQUENCE: 113
ggaatttctt taaaccccca                                           20

<210> SEQ ID NO 114
<211> LENGTH: 20
<212> TYPE: DNA
<213> ORGANISM: Artificial
<220> FEATURE:
<223> OTHER INFORMATION: Synthetic Sequence

<400> SEQUENCE: 114
gaaaaaacat taccttcatt                                           20

<210> SEQ ID NO 115
<211> LENGTH: 20
<212> TYPE: DNA
<213> ORGANISM: Artificial
<220> FEATURE:
<223> OTHER INFORMATION: Synthetic Sequence

<400> SEQUENCE: 115
tgttttacat attacacata                                           20

<210> SEQ ID NO 116
<211> LENGTH: 20
<212> TYPE: DNA
<213> ORGANISM: Artificial
<220> FEATURE:
<223> OTHER INFORMATION: Synthetic Sequence

<400> SEQUENCE: 116
ttatactgtt aattctggaa                                           20

<210> SEQ ID NO 117
<211> LENGTH: 20
<212> TYPE: DNA
<213> ORGANISM: Artificial
<220> FEATURE:
<223> OTHER INFORMATION: Synthetic Sequence

<400> SEQUENCE: 117
attaaagaga gtgataggga                                           20

<210> SEQ ID NO 118
<211> LENGTH: 20
<212> TYPE: DNA
<213> ORGANISM: Artificial
<220> FEATURE:
<223> OTHER INFORMATION: Synthetic Sequence

<400> SEQUENCE: 118
tcctgtacat tgtggcagga                                           20

<210> SEQ ID NO 119
<211> LENGTH: 20
<212> TYPE: DNA
<213> ORGANISM: Artificial
<220> FEATURE:
<223> OTHER INFORMATION: Synthetic Sequence

<400> SEQUENCE: 119
tgacaagtgc aagacttagt                                           20

<210> SEQ ID NO 120
<211> LENGTH: 20
<212> TYPE: DNA
<213> ORGANISM: Artificial
<220> FEATURE:
<223> OTHER INFORMATION: Synthetic Sequence

<400> SEQUENCE: 120
gctgtgtttt ctttgtagaa                                        20

<210> SEQ ID NO 121
<211> LENGTH: 20
<212> TYPE: DNA
<213> ORGANISM: Artificial
<220> FEATURE:
<223> OTHER INFORMATION: Synthetic Sequence

<400> SEQUENCE: 121
tcaaaatcat ctgtaaatcc                                        20

<210> SEQ ID NO 122
<211> LENGTH: 20
<212> TYPE: DNA
<213> ORGANISM: Artificial
<220> FEATURE:
<223> OTHER INFORMATION: Synthetic Sequence

<400> SEQUENCE: 122
gcatcctggt gagtttggga                                        20

<210> SEQ ID NO 123
<211> LENGTH: 20
<212> TYPE: DNA
<213> ORGANISM: Artificial
<220> FEATURE:
<223> OTHER INFORMATION: Synthetic Sequence

<400> SEQUENCE: 123
tcagttctgt ggccttcttg                                        20

<210> SEQ ID NO 124
<211> LENGTH: 20
<212> TYPE: DNA
<213> ORGANISM: Artificial
<220> FEATURE:
<223> OTHER INFORMATION: Synthetic Sequence

<400> SEQUENCE: 124
cctccagagg tttgagttct                                        20

<210> SEQ ID NO 125
<211> LENGTH: 20
<212> TYPE: DNA
<213> ORGANISM: Artificial
<220> FEATURE:
<223> OTHER INFORMATION: Synthetic Sequence

<400> SEQUENCE: 125
gtcttaagtg aaagtttttg                                        20

<210> SEQ ID NO 126
<211> LENGTH: 20
<212> TYPE: DNA
<213> ORGANISM: Artificial
<220> FEATURE:

<223> OTHER INFORMATION: Synthetic Sequence

<400> SEQUENCE: 126
gttccagaac tattacgttg                                           20

<210> SEQ ID NO 127
<211> LENGTH: 20
<212> TYPE: DNA
<213> ORGANISM: Artificial
<220> FEATURE:
<223> OTHER INFORMATION: Synthetic Sequence

<400> SEQUENCE: 127
catcagcata ttcacacatg                                           20

<210> SEQ ID NO 128
<211> LENGTH: 20
<212> TYPE: DNA
<213> ORGANISM: Artificial
<220> FEATURE:
<223> OTHER INFORMATION: Synthetic Sequence

<400> SEQUENCE: 128
aggtaatcca tctgttcaga                                           20

<210> SEQ ID NO 129
<211> LENGTH: 20
<212> TYPE: DNA
<213> ORGANISM: Artificial
<220> FEATURE:
<223> OTHER INFORMATION: Synthetic Sequence

<400> SEQUENCE: 129
gcacttaatt atcaagtcag                                           20

<210> SEQ ID NO 130
<211> LENGTH: 20
<212> TYPE: DNA
<213> ORGANISM: Artificial
<220> FEATURE:
<223> OTHER INFORMATION: Synthetic Sequence

<400> SEQUENCE: 130
atatttaaat aaatagaagg                                           20

<210> SEQ ID NO 131
<211> LENGTH: 20
<212> TYPE: DNA
<213> ORGANISM: Artificial
<220> FEATURE:
<223> OTHER INFORMATION: Synthetic Sequence

<400> SEQUENCE: 131
ataggtagca aaccatacat                                           20

<210> SEQ ID NO 132
<211> LENGTH: 20
<212> TYPE: DNA
<213> ORGANISM: Artificial
<220> FEATURE:
<223> OTHER INFORMATION: Synthetic Sequence

<400> SEQUENCE: 132
agatccatat ttatagtttt                                           20

```
<210> SEQ ID NO 133
<211> LENGTH: 20
<212> TYPE: DNA
<213> ORGANISM: Artificial
<220> FEATURE:
<223> OTHER INFORMATION: Synthetic Sequence

<400> SEQUENCE: 133
gaaaccattt tagagcccct                                              20

<210> SEQ ID NO 134
<211> LENGTH: 20
<212> TYPE: DNA
<213> ORGANISM: Artificial
<220> FEATURE:
<223> OTHER INFORMATION: Synthetic Sequence

<400> SEQUENCE: 134
ctatatttaa cattcaacat                                              20

<210> SEQ ID NO 135
<211> LENGTH: 20
<212> TYPE: DNA
<213> ORGANISM: Artificial
<220> FEATURE:
<223> OTHER INFORMATION: Synthetic Sequence

<400> SEQUENCE: 135
tcaaatttat taaatagttt                                              20

<210> SEQ ID NO 136
<211> LENGTH: 20
<212> TYPE: DNA
<213> ORGANISM: Artificial
<220> FEATURE:
<223> OTHER INFORMATION: Synthetic Sequence

<400> SEQUENCE: 136
tcctctgctg tccttgctga                                              20

<210> SEQ ID NO 137
<211> LENGTH: 20
<212> TYPE: DNA
<213> ORGANISM: Artificial
<220> FEATURE:
<223> OTHER INFORMATION: Synthetic Sequence

<400> SEQUENCE: 137
tctgagggtt gttttcaggg                                              20

<210> SEQ ID NO 138
<211> LENGTH: 20
<212> TYPE: DNA
<213> ORGANISM: Artificial
<220> FEATURE:
<223> OTHER INFORMATION: Synthetic Sequence

<400> SEQUENCE: 138
tgtcctttcc aggggagaga                                              20

<210> SEQ ID NO 139
<211> LENGTH: 20
<212> TYPE: DNA
<213> ORGANISM: Artificial
<220> FEATURE:
<223> OTHER INFORMATION: Synthetic Sequence
```

<400> SEQUENCE: 139
aagaggctga ggaacaagca                                               20

<210> SEQ ID NO 140
<211> LENGTH: 20
<212> TYPE: DNA
<213> ORGANISM: Artificial
<220> FEATURE:
<223> OTHER INFORMATION: Synthetic Sequence

<400> SEQUENCE: 140
tgattagaga gaggtccctg                                               20

<210> SEQ ID NO 141
<211> LENGTH: 20
<212> TYPE: DNA
<213> ORGANISM: Artificial
<220> FEATURE:
<223> OTHER INFORMATION: Synthetic Sequence

<400> SEQUENCE: 141
tgggctacag gcttgtcact                                               20

<210> SEQ ID NO 142
<211> LENGTH: 20
<212> TYPE: DNA
<213> ORGANISM: Artificial
<220> FEATURE:
<223> OTHER INFORMATION: Synthetic Sequence

<400> SEQUENCE: 142
tggttatctc tcagctccac                                               20

<210> SEQ ID NO 143
<211> LENGTH: 20
<212> TYPE: DNA
<213> ORGANISM: Artificial
<220> FEATURE:
<223> OTHER INFORMATION: Synthetic Sequence

<400> SEQUENCE: 143
ttgaagagga cctgggagta                                               20

<210> SEQ ID NO 144
<211> LENGTH: 20
<212> TYPE: DNA
<213> ORGANISM: Artificial
<220> FEATURE:
<223> OTHER INFORMATION: Synthetic Sequence

<400> SEQUENCE: 144
gctcttgatg gcagagagga                                               20

<210> SEQ ID NO 145
<211> LENGTH: 20
<212> TYPE: DNA
<213> ORGANISM: Artificial
<220> FEATURE:
<223> OTHER INFORMATION: Synthetic Sequence

<400> SEQUENCE: 145
acccttctcc agctggaaga                                               20

<210> SEQ ID NO 146
<211> LENGTH: 20

```
<212> TYPE: DNA
<213> ORGANISM: Artificial
<220> FEATURE:
<223> OTHER INFORMATION: Synthetic Sequence

<400> SEQUENCE: 146
tcggcaaagt cgagatagtc                                               20

<210> SEQ ID NO 147
<211> LENGTH: 20
<212> TYPE: DNA
<213> ORGANISM: Artificial
<220> FEATURE:
<223> OTHER INFORMATION: Synthetic Sequence

<400> SEQUENCE: 147
tttgggaagg ttggatgttc                                               20

<210> SEQ ID NO 148
<211> LENGTH: 20
<212> TYPE: DNA
<213> ORGANISM: Artificial
<220> FEATURE:
<223> OTHER INFORMATION: Synthetic Sequence

<400> SEQUENCE: 148
agaggttgag ggtgtctgaa                                               20

<210> SEQ ID NO 149
<211> LENGTH: 20
<212> TYPE: DNA
<213> ORGANISM: Artificial
<220> FEATURE:
<223> OTHER INFORMATION: Synthetic Sequence

<400> SEQUENCE: 149
ttctaagctt gggttccgac                                               20

<210> SEQ ID NO 150
<211> LENGTH: 20
<212> TYPE: DNA
<213> ORGANISM: Artificial
<220> FEATURE:
<223> OTHER INFORMATION: Synthetic Sequence

<400> SEQUENCE: 150
attcctgaat cccaggtttc                                               20

<210> SEQ ID NO 151
<211> LENGTH: 20
<212> TYPE: DNA
<213> ORGANISM: Artificial
<220> FEATURE:
<223> OTHER INFORMATION: Synthetic Sequence

<400> SEQUENCE: 151
tggaggcccc agtttgaatt                                               20

<210> SEQ ID NO 152
<211> LENGTH: 20
<212> TYPE: DNA
<213> ORGANISM: Artificial
<220> FEATURE:
<223> OTHER INFORMATION: Synthetic Sequence

<400> SEQUENCE: 152
```
tctccagatt ccagatgtca                                          20

<210> SEQ ID NO 153
<211> LENGTH: 20
<212> TYPE: DNA
<213> ORGANISM: Artificial
<220> FEATURE:
<223> OTHER INFORMATION: Synthetic Sequence

<400> SEQUENCE: 153
taggtgaggt cttctcaagt                                          20

<210> SEQ ID NO 154
<211> LENGTH: 20
<212> TYPE: DNA
<213> ORGANISM: Artificial
<220> FEATURE:
<223> OTHER INFORMATION: Synthetic Sequence

<400> SEQUENCE: 154
aaacatctgg agagaggaag                                          20

<210> SEQ ID NO 155
<211> LENGTH: 20
<212> TYPE: DNA
<213> ORGANISM: Artificial
<220> FEATURE:
<223> OTHER INFORMATION: Synthetic Sequence

<400> SEQUENCE: 155
ataaatagag ggagctggct                                          20

<210> SEQ ID NO 156
<211> LENGTH: 20
<212> TYPE: DNA
<213> ORGANISM: Artificial
<220> FEATURE:
<223> OTHER INFORMATION: Synthetic Sequence

<400> SEQUENCE: 156
acattgggtc ccccaggata                                          20

<210> SEQ ID NO 157
<211> LENGTH: 20
<212> TYPE: DNA
<213> ORGANISM: Artificial
<220> FEATURE:
<223> OTHER INFORMATION: Synthetic Sequence

<400> SEQUENCE: 157
ttgttcagct ccgttttcac                                          20

<210> SEQ ID NO 158
<211> LENGTH: 20
<212> TYPE: DNA
<213> ORGANISM: Artificial
<220> FEATURE:
<223> OTHER INFORMATION: Synthetic Sequence

<400> SEQUENCE: 158
ggtcaccaaa tcagcattgt                                          20

<210> SEQ ID NO 159
<211> LENGTH: 20
<212> TYPE: DNA
<213> ORGANISM: Artificial

```
<220> FEATURE:
<223> OTHER INFORMATION: Synthetic Sequence

<400> SEQUENCE: 159
attacagaca caactcccct                                          20

<210> SEQ ID NO 160
<211> LENGTH: 20
<212> TYPE: DNA
<213> ORGANISM: Artificial
<220> FEATURE:
<223> OTHER INFORMATION: Synthetic Sequence

<400> SEQUENCE: 160
agttgcttct ctccctctta                                          20

<210> SEQ ID NO 161
<211> LENGTH: 20
<212> TYPE: DNA
<213> ORGANISM: Artificial
<220> FEATURE:
<223> OTHER INFORMATION: Synthetic Sequence

<400> SEQUENCE: 161
atgtgagagg aagagaacct                                          20

<210> SEQ ID NO 162
<211> LENGTH: 20
<212> TYPE: DNA
<213> ORGANISM: Artificial
<220> FEATURE:
<223> OTHER INFORMATION: Synthetic Sequence

<400> SEQUENCE: 162
gatcatgctt tcagtgctca                                          20

<210> SEQ ID NO 163
<211> LENGTH: 20
<212> TYPE: DNA
<213> ORGANISM: Artificial
<220> FEATURE:
<223> OTHER INFORMATION: Synthetic Sequence

<400> SEQUENCE: 163
aaagtgcagc aggcagaaga                                          20

<210> SEQ ID NO 164
<211> LENGTH: 20
<212> TYPE: DNA
<213> ORGANISM: Artificial
<220> FEATURE:
<223> OTHER INFORMATION: Synthetic Sequence

<400> SEQUENCE: 164
agaagatgat ctgactgcct                                          20

<210> SEQ ID NO 165
<211> LENGTH: 20
<212> TYPE: DNA
<213> ORGANISM: Artificial
<220> FEATURE:
<223> OTHER INFORMATION: Synthetic Sequence

<400> SEQUENCE: 165
agcttgaggg tttgctacaa                                          20
```

```
<210> SEQ ID NO 166
<211> LENGTH: 20
<212> TYPE: DNA
<213> ORGANISM: Artificial
<220> FEATURE:
<223> OTHER INFORMATION: Synthetic Sequence

<400> SEQUENCE: 166
tgaggtacag gccctctgat                                               20

<210> SEQ ID NO 167
<211> LENGTH: 20
<212> TYPE: DNA
<213> ORGANISM: Artificial
<220> FEATURE:
<223> OTHER INFORMATION: Synthetic Sequence

<400> SEQUENCE: 167
ttgaccttgg tctggtagga                                               20

<210> SEQ ID NO 168
<211> LENGTH: 20
<212> TYPE: DNA
<213> ORGANISM: Artificial
<220> FEATURE:
<223> OTHER INFORMATION: Synthetic Sequence

<400> SEQUENCE: 168
agatagatgg gctcatacca                                               20

<210> SEQ ID NO 169
<211> LENGTH: 20
<212> TYPE: DNA
<213> ORGANISM: Artificial
<220> FEATURE:
<223> OTHER INFORMATION: Synthetic Sequence

<400> SEQUENCE: 169
attgatctca gcgctgagtc                                               20

<210> SEQ ID NO 170
<211> LENGTH: 20
<212> TYPE: DNA
<213> ORGANISM: Artificial
<220> FEATURE:
<223> OTHER INFORMATION: Synthetic Sequence

<400> SEQUENCE: 170
atgatcccaa agtagacctg                                               20

<210> SEQ ID NO 171
<211> LENGTH: 20
<212> TYPE: DNA
<213> ORGANISM: Artificial
<220> FEATURE:
<223> OTHER INFORMATION: Synthetic Sequence

<400> SEQUENCE: 171
taataaaggg attggggcag                                               20

<210> SEQ ID NO 172
<211> LENGTH: 20
<212> TYPE: DNA
<213> ORGANISM: Artificial
<220> FEATURE:
<223> OTHER INFORMATION: Synthetic Sequence
```

```
<400> SEQUENCE: 172
cccaattctc tttttgagcc                                              20

<210> SEQ ID NO 173
<211> LENGTH: 20
<212> TYPE: DNA
<213> ORGANISM: Artificial
<220> FEATURE:
<223> OTHER INFORMATION: Synthetic Sequence

<400> SEQUENCE: 173
gtggtggtct tgttgcttaa                                              20

<210> SEQ ID NO 174
<211> LENGTH: 20
<212> TYPE: DNA
<213> ORGANISM: Artificial
<220> FEATURE:
<223> OTHER INFORMATION: Synthetic Sequence

<400> SEQUENCE: 174
tagtggttgc cagcacttca                                              20

<210> SEQ ID NO 175
<211> LENGTH: 20
<212> TYPE: DNA
<213> ORGANISM: Artificial
<220> FEATURE:
<223> OTHER INFORMATION: Synthetic Sequence

<400> SEQUENCE: 175
aaagctgtag gccccagtga                                              20

<210> SEQ ID NO 176
<211> LENGTH: 20
<212> TYPE: DNA
<213> ORGANISM: Artificial
<220> FEATURE:
<223> OTHER INFORMATION: Synthetic Sequence

<400> SEQUENCE: 176
attctggcca gaaccaaagg                                              20

<210> SEQ ID NO 177
<211> LENGTH: 20
<212> TYPE: DNA
<213> ORGANISM: Artificial
<220> FEATURE:
<223> OTHER INFORMATION: Synthetic Sequence

<400> SEQUENCE: 177
ctaaggtcca cttgtgtcaa                                              20

<210> SEQ ID NO 178
<211> LENGTH: 20
<212> TYPE: DNA
<213> ORGANISM: Artificial
<220> FEATURE:
<223> OTHER INFORMATION: Synthetic Sequence

<400> SEQUENCE: 178
tccgtgtctc aaggaagtct                                              20

<210> SEQ ID NO 179
```

```
<211> LENGTH: 20
<212> TYPE: DNA
<213> ORGANISM: Artificial
<220> FEATURE:
<223> OTHER INFORMATION: Synthetic Sequence

<400> SEQUENCE: 179
ccggtctccc aaataaatac                                               20

<210> SEQ ID NO 180
<211> LENGTH: 20
<212> TYPE: DNA
<213> ORGANISM: Artificial
<220> FEATURE:
<223> OTHER INFORMATION: Synthetic Sequence

<400> SEQUENCE: 180
aaaacatgtc tgagccaagg                                               20

<210> SEQ ID NO 181
<211> LENGTH: 20
<212> TYPE: DNA
<213> ORGANISM: Artificial
<220> FEATURE:
<223> OTHER INFORMATION: Synthetic Sequence

<400> SEQUENCE: 181
atcaaaagaa ggcacagagg                                               20

<210> SEQ ID NO 182
<211> LENGTH: 20
<212> TYPE: DNA
<213> ORGANISM: Artificial
<220> FEATURE:
<223> OTHER INFORMATION: Synthetic Sequence

<400> SEQUENCE: 182
aggctcagca atgagtgaca                                               20

<210> SEQ ID NO 183
<211> LENGTH: 20
<212> TYPE: DNA
<213> ORGANISM: Artificial
<220> FEATURE:
<223> OTHER INFORMATION: Synthetic Sequence

<400> SEQUENCE: 183
ttctcgccac tgaatagtag                                               20

<210> SEQ ID NO 184
<211> LENGTH: 20
<212> TYPE: DNA
<213> ORGANISM: Artificial
<220> FEATURE:
<223> OTHER INFORMATION: Synthetic Sequence

<400> SEQUENCE: 184
tgcaatgtga tgcctttgac                                               20

<210> SEQ ID NO 185
<211> LENGTH: 20
<212> TYPE: DNA
<213> ORGANISM: Artificial
<220> FEATURE:
<223> OTHER INFORMATION: Synthetic Sequence

<400> SEQUENCE: 185
```
ttcgccttca ttgttggagt                                          20

<210> SEQ ID NO 186
<211> LENGTH: 20
<212> TYPE: DNA
<213> ORGANISM: Artificial
<220> FEATURE:
<223> OTHER INFORMATION: Synthetic Sequence

<400> SEQUENCE: 186
tagaggtcat ctatctgcga                                          20

<210> SEQ ID NO 187
<211> LENGTH: 20
<212> TYPE: DNA
<213> ORGANISM: Artificial
<220> FEATURE:
<223> OTHER INFORMATION: Synthetic Sequence

<400> SEQUENCE: 187
ccatttcctc tgagctttct                                          20

<210> SEQ ID NO 188
<211> LENGTH: 20
<212> TYPE: DNA
<213> ORGANISM: Artificial
<220> FEATURE:
<223> OTHER INFORMATION: Synthetic Sequence

<400> SEQUENCE: 188
aacaacatga aggccatcag                                          20

<210> SEQ ID NO 189
<211> LENGTH: 20
<212> TYPE: DNA
<213> ORGANISM: Artificial
<220> FEATURE:
<223> OTHER INFORMATION: Synthetic Sequence

<400> SEQUENCE: 189
aagtcaaaca cgaacgcttc                                          20

<210> SEQ ID NO 190
<211> LENGTH: 20
<212> TYPE: DNA
<213> ORGANISM: Artificial
<220> FEATURE:
<223> OTHER INFORMATION: Synthetic Sequence

<400> SEQUENCE: 190
gtgttctctt tcctctagca                                          20

<210> SEQ ID NO 191
<211> LENGTH: 20
<212> TYPE: DNA
<213> ORGANISM: Artificial
<220> FEATURE:
<223> OTHER INFORMATION: Synthetic Sequence

<400> SEQUENCE: 191
ggctcatttt ggaaagtgtg                                          20

<210> SEQ ID NO 192
<211> LENGTH: 20
<212> TYPE: DNA

```
<213> ORGANISM: Artificial
<220> FEATURE:
<223> OTHER INFORMATION: Synthetic Sequence

<400> SEQUENCE: 192
ctgaggaagt ctcaaataac                                              20

<210> SEQ ID NO 193
<211> LENGTH: 20
<212> TYPE: DNA
<213> ORGANISM: Artificial
<220> FEATURE:
<223> OTHER INFORMATION: Synthetic Sequence

<400> SEQUENCE: 193
caaagtccta accccttgat                                              20

<210> SEQ ID NO 194
<211> LENGTH: 20
<212> TYPE: DNA
<213> ORGANISM: Artificial
<220> FEATURE:
<223> OTHER INFORMATION: Synthetic Sequence

<400> SEQUENCE: 194
agacagctgc agaatttgca                                              20

<210> SEQ ID NO 195
<211> LENGTH: 20
<212> TYPE: DNA
<213> ORGANISM: Artificial
<220> FEATURE:
<223> OTHER INFORMATION: Synthetic Sequence

<400> SEQUENCE: 195
aaagggaaca cttccctcta                                              20

<210> SEQ ID NO 196
<211> LENGTH: 20
<212> TYPE: DNA
<213> ORGANISM: Artificial
<220> FEATURE:
<223> OTHER INFORMATION: Synthetic Sequence

<400> SEQUENCE: 196
tggtccgctt gtgagattct                                              20

<210> SEQ ID NO 197
<211> LENGTH: 20
<212> TYPE: DNA
<213> ORGANISM: Artificial
<220> FEATURE:
<223> OTHER INFORMATION: Synthetic Sequence

<400> SEQUENCE: 197
ttctgtgaat gcctgtgaga                                              20

<210> SEQ ID NO 198
<211> LENGTH: 20
<212> TYPE: DNA
<213> ORGANISM: Artificial
<220> FEATURE:
<223> OTHER INFORMATION: Synthetic Sequence

<400> SEQUENCE: 198
gactggagaa gaacatgagt                                              20
```

```
<210> SEQ ID NO 199
<211> LENGTH: 20
<212> TYPE: DNA
<213> ORGANISM: Artificial
<220> FEATURE:
<223> OTHER INFORMATION: Synthetic Sequence

<400> SEQUENCE: 199
atggttctga gttggatctg                                              20

<210> SEQ ID NO 200
<211> LENGTH: 20
<212> TYPE: DNA
<213> ORGANISM: Artificial
<220> FEATURE:
<223> OTHER INFORMATION: Synthetic Sequence

<400> SEQUENCE: 200
aatccacgcg ttctgatgag                                              20

<210> SEQ ID NO 201
<211> LENGTH: 20
<212> TYPE: DNA
<213> ORGANISM: Artificial
<220> FEATURE:
<223> OTHER INFORMATION: Synthetic Sequence

<400> SEQUENCE: 201
aacccctgaa aaaggatgga                                              20

<210> SEQ ID NO 202
<211> LENGTH: 20
<212> TYPE: DNA
<213> ORGANISM: Artificial
<220> FEATURE:
<223> OTHER INFORMATION: Synthetic Sequence

<400> SEQUENCE: 202
ctgatccagg taactctttc                                              20

<210> SEQ ID NO 203
<211> LENGTH: 20
<212> TYPE: DNA
<213> ORGANISM: Artificial
<220> FEATURE:
<223> OTHER INFORMATION: Synthetic Sequence

<400> SEQUENCE: 203
gtgagtggtt cagtgaagat                                              20

<210> SEQ ID NO 204
<211> LENGTH: 20
<212> TYPE: DNA
<213> ORGANISM: Artificial
<220> FEATURE:
<223> OTHER INFORMATION: Synthetic Sequence

<400> SEQUENCE: 204
gaaatgcttg cctgagagtt                                              20

<210> SEQ ID NO 205
<211> LENGTH: 20
<212> TYPE: DNA
<213> ORGANISM: Artificial
<220> FEATURE:
```

<223> OTHER INFORMATION: Synthetic Sequence

<400> SEQUENCE: 205
ccaggaaatg aactttccag                                              20

<210> SEQ ID NO 206
<211> LENGTH: 20
<212> TYPE: DNA
<213> ORGANISM: Artificial
<220> FEATURE:
<223> OTHER INFORMATION: Synthetic Sequence

<400> SEQUENCE: 206
ccccaaaaca gctgctttaa                                              20

<210> SEQ ID NO 207
<211> LENGTH: 20
<212> TYPE: DNA
<213> ORGANISM: Artificial
<220> FEATURE:
<223> OTHER INFORMATION: Synthetic Sequence

<400> SEQUENCE: 207
gttaggctac caagtagtgt                                              20

<210> SEQ ID NO 208
<211> LENGTH: 20
<212> TYPE: DNA
<213> ORGANISM: Artificial
<220> FEATURE:
<223> OTHER INFORMATION: Synthetic Sequence

<400> SEQUENCE: 208
gaaggccatt gtcgatagaa                                              20

<210> SEQ ID NO 209
<211> LENGTH: 20
<212> TYPE: DNA
<213> ORGANISM: Artificial
<220> FEATURE:
<223> OTHER INFORMATION: Synthetic Sequence

<400> SEQUENCE: 209
tgaaatagtt ccgcagctct                                              20

<210> SEQ ID NO 210
<211> LENGTH: 20
<212> TYPE: DNA
<213> ORGANISM: Artificial
<220> FEATURE:
<223> OTHER INFORMATION: Synthetic Sequence

<400> SEQUENCE: 210
acactaaacc ttgatagtgg                                              20

<210> SEQ ID NO 211
<211> LENGTH: 20
<212> TYPE: DNA
<213> ORGANISM: Artificial
<220> FEATURE:
<223> OTHER INFORMATION: Synthetic Sequence

<400> SEQUENCE: 211
gagaagagat tgtggaactg                                              20

```
<210> SEQ ID NO 212
<211> LENGTH: 20
<212> TYPE: DNA
<213> ORGANISM: Artificial
<220> FEATURE:
<223> OTHER INFORMATION: Synthetic Sequence

<400> SEQUENCE: 212
ccctacactt gctgtattca                                               20

<210> SEQ ID NO 213
<211> LENGTH: 20
<212> TYPE: DNA
<213> ORGANISM: Artificial
<220> FEATURE:
<223> OTHER INFORMATION: Synthetic Sequence

<400> SEQUENCE: 213
tatgagaaga accccgaatg                                               20

<210> SEQ ID NO 214
<211> LENGTH: 20
<212> TYPE: DNA
<213> ORGANISM: Artificial
<220> FEATURE:
<223> OTHER INFORMATION: Synthetic Sequence

<400> SEQUENCE: 214
aacatgaggt gactgtaagg                                               20

<210> SEQ ID NO 215
<211> LENGTH: 20
<212> TYPE: DNA
<213> ORGANISM: Artificial
<220> FEATURE:
<223> OTHER INFORMATION: Synthetic Sequence

<400> SEQUENCE: 215
gcacatttat agtatcccct                                               20

<210> SEQ ID NO 216
<211> LENGTH: 20
<212> TYPE: DNA
<213> ORGANISM: Artificial
<220> FEATURE:
<223> OTHER INFORMATION: Synthetic Sequence

<400> SEQUENCE: 216
gaaacaggga gacagaagat                                               20

<210> SEQ ID NO 217
<211> LENGTH: 20
<212> TYPE: DNA
<213> ORGANISM: Artificial
<220> FEATURE:
<223> OTHER INFORMATION: Synthetic Sequence

<400> SEQUENCE: 217
gtagcagaca tctcagagat                                               20

<210> SEQ ID NO 218
<211> LENGTH: 20
<212> TYPE: DNA
<213> ORGANISM: Artificial
<220> FEATURE:
<223> OTHER INFORMATION: Synthetic Sequence
```

<400> SEQUENCE: 218
gcactgtact ctttagagca                                              20

<210> SEQ ID NO 219
<211> LENGTH: 20
<212> TYPE: DNA
<213> ORGANISM: Artificial
<220> FEATURE:
<223> OTHER INFORMATION: Synthetic Sequence

<400> SEQUENCE: 219
gccaggacag ttgttcttat                                              20

<210> SEQ ID NO 220
<211> LENGTH: 20
<212> TYPE: DNA
<213> ORGANISM: Artificial
<220> FEATURE:
<223> OTHER INFORMATION: Synthetic Sequence

<400> SEQUENCE: 220
ggacagtagc agggatttaa                                              20

<210> SEQ ID NO 221
<211> LENGTH: 20
<212> TYPE: DNA
<213> ORGANISM: Artificial
<220> FEATURE:
<223> OTHER INFORMATION: Synthetic Sequence

<400> SEQUENCE: 221 cgtaacccatt acgaatcaga                                             20

<210> SEQ ID NO 222
<211> LENGTH: 20
<212> TYPE: DNA
<213> ORGANISM: Artificial
<220> FEATURE:
<223> OTHER INFORMATION: Synthetic Sequence

<400> SEQUENCE: 222
atgctccaac agaaaccaca                                              20

<210> SEQ ID NO 223
<211> LENGTH: 20
<212> TYPE: DNA
<213> ORGANISM: Artificial
<220> FEATURE:
<223> OTHER INFORMATION: Synthetic Sequence

<400> SEQUENCE: 223
atttgccaga ggctccttat                                              20

<210> SEQ ID NO 224
<211> LENGTH: 20
<212> TYPE: DNA
<213> ORGANISM: Artificial
<220> FEATURE:
<223> OTHER INFORMATION: Synthetic Sequence

<400> SEQUENCE: 224
agagcattct gccatgaaag                                              20

<210> SEQ ID NO 225
<211> LENGTH: 20

```
<212> TYPE: DNA
<213> ORGANISM: Artificial
<220> FEATURE:
<223> OTHER INFORMATION: Synthetic Sequence

<400> SEQUENCE: 225
cactatagaa tctaaggcag                                              20

<210> SEQ ID NO 226
<211> LENGTH: 20
<212> TYPE: DNA
<213> ORGANISM: Artificial
<220> FEATURE:
<223> OTHER INFORMATION: Synthetic Sequence

<400> SEQUENCE: 226
acagttattc aggcgtcaca                                              20

<210> SEQ ID NO 227
<211> LENGTH: 20
<212> TYPE: DNA
<213> ORGANISM: Artificial
<220> FEATURE:
<223> OTHER INFORMATION: Synthetic Sequence

<400> SEQUENCE: 227
ggcaagttaa tcccaacatg                                              20

<210> SEQ ID NO 228
<211> LENGTH: 20
<212> TYPE: DNA
<213> ORGANISM: Artificial
<220> FEATURE:
<223> OTHER INFORMATION: Synthetic Sequence

<400> SEQUENCE: 228
gtactcaagt atatactccc                                              20

<210> SEQ ID NO 229
<211> LENGTH: 20
<212> TYPE: DNA
<213> ORGANISM: Artificial
<220> FEATURE:
<223> OTHER INFORMATION: Synthetic Sequence

<400> SEQUENCE: 229
caaatgtggc aaagactcac                                              20

<210> SEQ ID NO 230
<211> LENGTH: 20
<212> TYPE: DNA
<213> ORGANISM: Artificial
<220> FEATURE:
<223> OTHER INFORMATION: Synthetic Sequence

<400> SEQUENCE: 230
gccctgttgt gcttgtatat                                              20

<210> SEQ ID NO 231
<211> LENGTH: 20
<212> TYPE: DNA
<213> ORGANISM: Artificial
<220> FEATURE:
<223> OTHER INFORMATION: Synthetic Sequence

<400> SEQUENCE: 231
```
caaaacccca aggtgacaaa                                               20

<210> SEQ ID NO 232
<211> LENGTH: 17
<212> TYPE: DNA
<213> ORGANISM: Artificial
<220> FEATURE:
<223> OTHER INFORMATION: Synthetic Sequence

<400> SEQUENCE: 232
ctgctgcccg tgtcctt                                                  17

<210> SEQ ID NO 233
<211> LENGTH: 17
<212> TYPE: DNA
<213> ORGANISM: Artificial
<220> FEATURE:
<223> OTHER INFORMATION: Synthetic Sequence

<400> SEQUENCE: 233
ctcgagtgtc agcagag                                                  17

<210> SEQ ID NO 234
<211> LENGTH: 17
<212> TYPE: DNA
<213> ORGANISM: Artificial
<220> FEATURE:
<223> OTHER INFORMATION: Synthetic Sequence

<400> SEQUENCE: 234
agtggagacc tgcatga                                                  17

<210> SEQ ID NO 235
<211> LENGTH: 17
<212> TYPE: DNA
<213> ORGANISM: Artificial
<220> FEATURE:
<223> OTHER INFORMATION: Synthetic Sequence

<400> SEQUENCE: 235
gagagccatg gtgcaga                                                  17

<210> SEQ ID NO 236
<211> LENGTH: 17
<212> TYPE: DNA
<213> ORGANISM: Artificial
<220> FEATURE:
<223> OTHER INFORMATION: Synthetic Sequence

<400> SEQUENCE: 236
cgtgtcagca gcaagtg                                                  17

<210> SEQ ID NO 237
<211> LENGTH: 17
<212> TYPE: DNA
<213> ORGANISM: Artificial
<220> FEATURE:
<223> OTHER INFORMATION: Synthetic Sequence

<400> SEQUENCE: 237
gtggaatctg ccgggag                                                  17

<210> SEQ ID NO 238
<211> LENGTH: 17
<212> TYPE: DNA
<213> ORGANISM: Artificial

```
<220> FEATURE:
<223> OTHER INFORMATION: Synthetic Sequence

<400> SEQUENCE: 238
ggctgctcgt ctcaaag                                              17

<210> SEQ ID NO 239
<211> LENGTH: 17
<212> TYPE: DNA
<213> ORGANISM: Artificial
<220> FEATURE:
<223> OTHER INFORMATION: Synthetic Sequence

<400> SEQUENCE: 239
gcttggttag gaagatg                                              17

<210> SEQ ID NO 240
<211> LENGTH: 17
<212> TYPE: DNA
<213> ORGANISM: Artificial
<220> FEATURE:
<223> OTHER INFORMATION: Synthetic Sequence

<400> SEQUENCE: 240
cactcctcac tggggtc                                              17

<210> SEQ ID NO 241
<211> LENGTH: 17
<212> TYPE: DNA
<213> ORGANISM: Artificial
<220> FEATURE:
<223> OTHER INFORMATION: Synthetic Sequence

<400> SEQUENCE: 241
ctcaggcact cagctcc                                              17

<210> SEQ ID NO 242
<211> LENGTH: 17
<212> TYPE: DNA
<213> ORGANISM: Artificial
<220> FEATURE:
<223> OTHER INFORMATION: Synthetic Sequence

<400> SEQUENCE: 242
ccaccgaggt cgctggg                                              17

<210> SEQ ID NO 243
<211> LENGTH: 17
<212> TYPE: DNA
<213> ORGANISM: Artificial
<220> FEATURE:
<223> OTHER INFORMATION: Synthetic Sequence

<400> SEQUENCE: 243
acacgcatgt tcccaag                                              17

<210> SEQ ID NO 244
<211> LENGTH: 17
<212> TYPE: DNA
<213> ORGANISM: Artificial
<220> FEATURE:
<223> OTHER INFORMATION: Synthetic Sequence

<400> SEQUENCE: 244
gcaacaacca gtccata                                              17
```

```
<210> SEQ ID NO 245
<211> LENGTH: 17
<212> TYPE: DNA
<213> ORGANISM: Artificial
<220> FEATURE:
<223> OTHER INFORMATION: Synthetic Sequence

<400> SEQUENCE: 245
tttaagttaa gaagagt                                                        17

<210> SEQ ID NO 246
<211> LENGTH: 17
<212> TYPE: DNA
<213> ORGANISM: Artificial
<220> FEATURE:
<223> OTHER INFORMATION: Synthetic Sequence

<400> SEQUENCE: 246
aaattacaaa aactaaa                                                        17

<210> SEQ ID NO 247
<211> LENGTH: 17
<212> TYPE: DNA
<213> ORGANISM: Artificial
<220> FEATURE:
<223> OTHER INFORMATION: Synthetic Sequence

<400> SEQUENCE: 247
cagagcaaac aatcaca                                                        17

<210> SEQ ID NO 248
<211> LENGTH: 17
<212> TYPE: DNA
<213> ORGANISM: Artificial
<220> FEATURE:
<223> OTHER INFORMATION: Synthetic Sequence

<400> SEQUENCE: 248
gttgtcacca gacgcgg                                                        17

<210> SEQ ID NO 249
<211> LENGTH: 17
<212> TYPE: DNA
<213> ORGANISM: Artificial
<220> FEATURE:
<223> OTHER INFORMATION: Synthetic Sequence

<400> SEQUENCE: 249
gccatgactg cctacac                                                        17

<210> SEQ ID NO 250
<211> LENGTH: 17
<212> TYPE: DNA
<213> ORGANISM: Artificial
<220> FEATURE:
<223> OTHER INFORMATION: Synthetic Sequence

<400> SEQUENCE: 250
gcatccgata cacattt                                                        17

<210> SEQ ID NO 251
<211> LENGTH: 17
<212> TYPE: DNA
<213> ORGANISM: Artificial
<220> FEATURE:
<223> OTHER INFORMATION: Synthetic Sequence
```

-continued

<400> SEQUENCE: 251
attatttccc caggccg                                                  17

<210> SEQ ID NO 252
<211> LENGTH: 17
<212> TYPE: DNA
<213> ORGANISM: Artificial
<220> FEATURE:
<223> OTHER INFORMATION: Synthetic Sequence

<400> SEQUENCE: 252
agaaaggact gaccact                                                  17

<210> SEQ ID NO 253
<211> LENGTH: 17
<212> TYPE: DNA
<213> ORGANISM: Artificial
<220> FEATURE:
<223> OTHER INFORMATION: Synthetic Sequence

<400> SEQUENCE: 253
gagcaggtga cggaatg                                                  17

<210> SEQ ID NO 254
<211> LENGTH: 17
<212> TYPE: DNA
<213> ORGANISM: Artificial
<220> FEATURE:
<223> OTHER INFORMATION: Synthetic Sequence

<400> SEQUENCE: 254
gaggacagca agggcag                                                  17

<210> SEQ ID NO 255
<211> LENGTH: 17
<212> TYPE: DNA
<213> ORGANISM: Artificial
<220> FEATURE:
<223> OTHER INFORMATION: Synthetic Sequence

<400> SEQUENCE: 255
tgcagagaac tggttgc                                                  17

<210> SEQ ID NO 256
<211> LENGTH: 17
<212> TYPE: DNA
<213> ORGANISM: Artificial
<220> FEATURE:
<223> OTHER INFORMATION: Synthetic Sequence

<400> SEQUENCE: 256
gtagctgaag cagcagg                                                  17

<210> SEQ ID NO 257
<211> LENGTH: 17
<212> TYPE: DNA
<213> ORGANISM: Artificial
<220> FEATURE:
<223> OTHER INFORMATION: Synthetic Sequence

<400> SEQUENCE: 257
agtcagctat gaaattc                                                  17

<210> SEQ ID NO 258

```
<211> LENGTH: 17
<212> TYPE: DNA
<213> ORGANISM: Artificial
<220> FEATURE:
<223> OTHER INFORMATION: Synthetic Sequence

<400> SEQUENCE: 258
caccgggctt ggagcac                                                    17

<210> SEQ ID NO 259
<211> LENGTH: 17
<212> TYPE: DNA
<213> ORGANISM: Artificial
<220> FEATURE:
<223> OTHER INFORMATION: Synthetic Sequence

<400> SEQUENCE: 259
cacagacctg ccggctt                                                    17

<210> SEQ ID NO 260
<211> LENGTH: 17
<212> TYPE: DNA
<213> ORGANISM: Artificial
<220> FEATURE:
<223> OTHER INFORMATION: Synthetic Sequence

<400> SEQUENCE: 260
cgctgacata tttctgg                                                    17

<210> SEQ ID NO 261
<211> LENGTH: 17
<212> TYPE: DNA
<213> ORGANISM: Artificial
<220> FEATURE:
<223> OTHER INFORMATION: Synthetic Sequence

<400> SEQUENCE: 261
ctcgaagctt ctggacc                                                    17

<210> SEQ ID NO 262
<211> LENGTH: 17
<212> TYPE: DNA
<213> ORGANISM: Artificial
<220> FEATURE:
<223> OTHER INFORMATION: Synthetic Sequence

<400> SEQUENCE: 262
tcaggctcct gctcctc                                                    17

<210> SEQ ID NO 263
<211> LENGTH: 17
<212> TYPE: DNA
<213> ORGANISM: Artificial
<220> FEATURE:
<223> OTHER INFORMATION: Synthetic Sequence

<400> SEQUENCE: 263
aagaggtagc tgtggag                                                    17

<210> SEQ ID NO 264
<211> LENGTH: 17
<212> TYPE: DNA
<213> ORGANISM: Artificial
<220> FEATURE:
<223> OTHER INFORMATION: Synthetic Sequence

<400> SEQUENCE: 264
```
ccacagtgtg gctgttt 17

<210> SEQ ID NO 265
<211> LENGTH: 17
<212> TYPE: DNA
<213> ORGANISM: Artificial
<220> FEATURE:
<223> OTHER INFORMATION: Synthetic Sequence

<400> SEQUENCE: 265
agtataaata aattaaa 17

<210> SEQ ID NO 266
<211> LENGTH: 17
<212> TYPE: DNA
<213> ORGANISM: Artificial
<220> FEATURE:
<223> OTHER INFORMATION: Synthetic Sequence

<400> SEQUENCE: 266
acacactgtg aaatcga 17

<210> SEQ ID NO 267
<211> LENGTH: 17
<212> TYPE: DNA
<213> ORGANISM: Artificial
<220> FEATURE:
<223> OTHER INFORMATION: Synthetic Sequence

<400> SEQUENCE: 267
aggggacagg ggaactc 17

<210> SEQ ID NO 268
<211> LENGTH: 17
<212> TYPE: DNA
<213> ORGANISM: Artificial
<220> FEATURE:
<223> OTHER INFORMATION: Synthetic Sequence

<400> SEQUENCE: 268
gctgatgaca gccactc 17

<210> SEQ ID NO 269
<211> LENGTH: 17
<212> TYPE: DNA
<213> ORGANISM: Artificial
<220> FEATURE:
<223> OTHER INFORMATION: Synthetic Sequence

<400> SEQUENCE: 269
tcagtctggt ggctttg 17

<210> SEQ ID NO 270
<211> LENGTH: 17
<212> TYPE: DNA
<213> ORGANISM: Artificial
<220> FEATURE:
<223> OTHER INFORMATION: Synthetic Sequence

<400> SEQUENCE: 270
tcacagccct gaacaaa 17

<210> SEQ ID NO 271
<211> LENGTH: 17
<212> TYPE: DNA

```
<213> ORGANISM: Artificial
<220> FEATURE:
<223> OTHER INFORMATION: Synthetic Sequence

<400> SEQUENCE: 271
accttttaaa agagcat                                                  17

<210> SEQ ID NO 272
<211> LENGTH: 18
<212> TYPE: DNA
<213> ORGANISM: Artificial
<220> FEATURE:
<223> OTHER INFORMATION: Synthetic Sequence

<400> SEQUENCE: 272
cggtaaaacc acacagga                                                 18

<210> SEQ ID NO 273
<211> LENGTH: 18
<212> TYPE: DNA
<213> ORGANISM: Artificial
<220> FEATURE:
<223> OTHER INFORMATION: Synthetic Sequence

<400> SEQUENCE: 273
cagcacgctt ttcattgg                                                 18

<210> SEQ ID NO 274
<211> LENGTH: 18
<212> TYPE: DNA
<213> ORGANISM: Artificial
<220> FEATURE:
<223> OTHER INFORMATION: Synthetic Sequence

<400> SEQUENCE: 274
ttgacacagg catacctg                                                 18

<210> SEQ ID NO 275
<211> LENGTH: 18
<212> TYPE: DNA
<213> ORGANISM: Artificial
<220> FEATURE:
<223> OTHER INFORMATION: Synthetic Sequence

<400> SEQUENCE: 275
ccactgtggt gttgtctc                                                 18

<210> SEQ ID NO 276
<211> LENGTH: 18
<212> TYPE: DNA
<213> ORGANISM: Artificial
<220> FEATURE:
<223> OTHER INFORMATION: Synthetic Sequence

<400> SEQUENCE: 276
cgcacgtcct tcttggag                                                 18

<210> SEQ ID NO 277
<211> LENGTH: 18
<212> TYPE: DNA
<213> ORGANISM: Artificial
<220> FEATURE:
<223> OTHER INFORMATION: Synthetic Sequence

<400> SEQUENCE: 277
acaaatgatg gagtacat                                                 18
```

```
<210> SEQ ID NO 278
<211> LENGTH: 18
<212> TYPE: DNA
<213> ORGANISM: Artificial
<220> FEATURE:
<223> OTHER INFORMATION: Synthetic Sequence

<400> SEQUENCE: 278
ataggtcaac acgaccag                                                  18

<210> SEQ ID NO 279
<211> LENGTH: 18
<212> TYPE: DNA
<213> ORGANISM: Artificial
<220> FEATURE:
<223> OTHER INFORMATION: Synthetic Sequence

<400> SEQUENCE: 279
ttgagcaggt aggtatcg                                                  18

<210> SEQ ID NO 280
<211> LENGTH: 18
<212> TYPE: DNA
<213> ORGANISM: Artificial
<220> FEATURE:
<223> OTHER INFORMATION: Synthetic Sequence

<400> SEQUENCE: 280
cgaagaccca ggacttgg                                                  18

<210> SEQ ID NO 281
<211> LENGTH: 18
<212> TYPE: DNA
<213> ORGANISM: Artificial
<220> FEATURE:
<223> OTHER INFORMATION: Synthetic Sequence

<400> SEQUENCE: 281
gctcatcttg tagatggc                                                  18

<210> SEQ ID NO 282
<211> LENGTH: 18
<212> TYPE: DNA
<213> ORGANISM: Artificial
<220> FEATURE:
<223> OTHER INFORMATION: Synthetic Sequence

<400> SEQUENCE: 282
gtcaatgctg atgcaaag                                                  18

<210> SEQ ID NO 283
<211> LENGTH: 18
<212> TYPE: DNA
<213> ORGANISM: Artificial
<220> FEATURE:
<223> OTHER INFORMATION: Synthetic Sequence

<400> SEQUENCE: 283
ggacagcttg ctgatgag                                                  18

<210> SEQ ID NO 284
<211> LENGTH: 18
<212> TYPE: DNA
<213> ORGANISM: Artificial
<220> FEATURE:
```

<223> OTHER INFORMATION: Synthetic Sequence

<400> SEQUENCE: 284
tacaggagct ctgggatg                                                 18

<210> SEQ ID NO 285
<211> LENGTH: 18
<212> TYPE: DNA
<213> ORGANISM: Artificial
<220> FEATURE:
<223> OTHER INFORMATION: Synthetic Sequence

<400> SEQUENCE: 285
agagcatcgc atcgcttg                                                 18

<210> SEQ ID NO 286
<211> LENGTH: 18
<212> TYPE: DNA
<213> ORGANISM: Artificial
<220> FEATURE:
<223> OTHER INFORMATION: Synthetic Sequence

<400> SEQUENCE: 286
ccacctggat ggtgataa                                                 18

<210> SEQ ID NO 287
<211> LENGTH: 18
<212> TYPE: DNA
<213> ORGANISM: Artificial
<220> FEATURE:
<223> OTHER INFORMATION: Synthetic Sequence

<400> SEQUENCE: 287
gaagctcatg gccagcag                                                 18

<210> SEQ ID NO 288
<211> LENGTH: 18
<212> TYPE: DNA
<213> ORGANISM: Artificial
<220> FEATURE:
<223> OTHER INFORMATION: Synthetic Sequence

<400> SEQUENCE: 288
ctcaaagttg cgtgcctg                                                 18

<210> SEQ ID NO 289
<211> LENGTH: 18
<212> TYPE: DNA
<213> ORGANISM: Artificial
<220> FEATURE:
<223> OTHER INFORMATION: Synthetic Sequence

<400> SEQUENCE: 289
atgaagacca cgaccaca                                                 18

<210> SEQ ID NO 290
<211> LENGTH: 18
<212> TYPE: DNA
<213> ORGANISM: Artificial
<220> FEATURE:
<223> OTHER INFORMATION: Synthetic Sequence

<400> SEQUENCE: 290
cgtctgggcc aggaccac                                                 18

```
<210> SEQ ID NO 291
<211> LENGTH: 18
<212> TYPE: DNA
<213> ORGANISM: Artificial
<220> FEATURE:
<223> OTHER INFORMATION: Synthetic Sequence

<400> SEQUENCE: 291
ttgcttactg agctcaca                                                 18

<210> SEQ ID NO 292
<211> LENGTH: 18
<212> TYPE: DNA
<213> ORGANISM: Artificial
<220> FEATURE:
<223> OTHER INFORMATION: Synthetic Sequence

<400> SEQUENCE: 292
gacgcaggcc aggctgta                                                 18

<210> SEQ ID NO 293
<211> LENGTH: 18
<212> TYPE: DNA
<213> ORGANISM: Artificial
<220> FEATURE:
<223> OTHER INFORMATION: Synthetic Sequence

<400> SEQUENCE: 293
gacgccgatg aaggcgta                                                 18

<210> SEQ ID NO 294
<211> LENGTH: 18
<212> TYPE: DNA
<213> ORGANISM: Artificial
<220> FEATURE:
<223> OTHER INFORMATION: Synthetic Sequence

<400> SEQUENCE: 294
gcccaggtcc ttgaagag                                                 18

<210> SEQ ID NO 295
<211> LENGTH: 18
<212> TYPE: DNA
<213> ORGANISM: Artificial
<220> FEATURE:
<223> OTHER INFORMATION: Synthetic Sequence

<400> SEQUENCE: 295
gatgtgccga caggaaga                                                 18

<210> SEQ ID NO 296
<211> LENGTH: 18
<212> TYPE: DNA
<213> ORGANISM: Artificial
<220> FEATURE:
<223> OTHER INFORMATION: Synthetic Sequence

<400> SEQUENCE: 296
caggtccatg acgctctc                                                 18

<210> SEQ ID NO 297
<211> LENGTH: 18
<212> TYPE: DNA
<213> ORGANISM: Artificial
<220> FEATURE:
<223> OTHER INFORMATION: Synthetic Sequence
```

-continued

<400> SEQUENCE: 297
aatgacaagg agagccac					18

<210> SEQ ID NO 298
<211> LENGTH: 18
<212> TYPE: DNA
<213> ORGANISM: Artificial
<220> FEATURE:
<223> OTHER INFORMATION: Synthetic Sequence

<400> SEQUENCE: 298
tgtaatcgtc cgtgacct					18

<210> SEQ ID NO 299
<211> LENGTH: 18
<212> TYPE: DNA
<213> ORGANISM: Artificial
<220> FEATURE:
<223> OTHER INFORMATION: Synthetic Sequence

<400> SEQUENCE: 299
aagactcgaa caaagtgt					18

<210> SEQ ID NO 300
<211> LENGTH: 18
<212> TYPE: DNA
<213> ORGANISM: Artificial
<220> FEATURE:
<223> OTHER INFORMATION: Synthetic Sequence

<400> SEQUENCE: 300
ggaggaacca ggcttaa					18

<210> SEQ ID NO 301
<211> LENGTH: 18
<212> TYPE: DNA
<213> ORGANISM: Artificial
<220> FEATURE:
<223> OTHER INFORMATION: Synthetic Sequence

<400> SEQUENCE: 301
attgcccagt aggcccac					18

<210> SEQ ID NO 302
<211> LENGTH: 18
<212> TYPE: DNA
<213> ORGANISM: Artificial
<220> FEATURE:
<223> OTHER INFORMATION: Synthetic Sequence

<400> SEQUENCE: 302
tggtcttgag cctcttga					18

<210> SEQ ID NO 303
<211> LENGTH: 18
<212> TYPE: DNA
<213> ORGANISM: Artificial
<220> FEATURE:
<223> OTHER INFORMATION: Synthetic Sequence

<400> SEQUENCE: 303
tgtaggccca gaagggaa					18

<210> SEQ ID NO 304
<211> LENGTH: 18

```
<212> TYPE: DNA
<213> ORGANISM: Artificial
<220> FEATURE:
<223> OTHER INFORMATION: Synthetic Sequence

<400> SEQUENCE: 304
tgagcttgca aaagtgga                                              18

<210> SEQ ID NO 305
<211> LENGTH: 18
<212> TYPE: DNA
<213> ORGANISM: Artificial
<220> FEATURE:
<223> OTHER INFORMATION: Synthetic Sequence

<400> SEQUENCE: 305
taggagcatg ccactgaa                                              18

<210> SEQ ID NO 306
<211> LENGTH: 18
<212> TYPE: DNA
<213> ORGANISM: Artificial
<220> FEATURE:
<223> OTHER INFORMATION: Synthetic Sequence

<400> SEQUENCE: 306
ctggacgatg gccacgta                                              18

<210> SEQ ID NO 307
<211> LENGTH: 18
<212> TYPE: DNA
<213> ORGANISM: Artificial
<220> FEATURE:
<223> OTHER INFORMATION: Synthetic Sequence

<400> SEQUENCE: 307
gcactgtggc tagtatcc                                              18

<210> SEQ ID NO 308
<211> LENGTH: 18
<212> TYPE: DNA
<213> ORGANISM: Artificial
<220> FEATURE:
<223> OTHER INFORMATION: Synthetic Sequence

<400> SEQUENCE: 308
ctgctcctct ggaggtca                                              18

<210> SEQ ID NO 309
<211> LENGTH: 18
<212> TYPE: DNA
<213> ORGANISM: Artificial
<220> FEATURE:
<223> OTHER INFORMATION: Synthetic Sequence

<400> SEQUENCE: 309
ctccacatgc tctgtgat                                              18

<210> SEQ ID NO 310
<211> LENGTH: 18
<212> TYPE: DNA
<213> ORGANISM: Artificial
<220> FEATURE:
<223> OTHER INFORMATION: Synthetic Sequence

<400> SEQUENCE: 310
```
cagaaagccg atcaccat                                                 18

<210> SEQ ID NO 311
<211> LENGTH: 18
<212> TYPE: DNA
<213> ORGANISM: Artificial
<220> FEATURE:
<223> OTHER INFORMATION: Synthetic Sequence

<400> SEQUENCE: 311
gcggatgatg acaaggta                                                 18

<210> SEQ ID NO 312
<211> LENGTH: 18
<212> TYPE: DNA
<213> ORGANISM: Artificial
<220> FEATURE:
<223> OTHER INFORMATION: Synthetic Sequence

<400> SEQUENCE: 312
atcaccttga tggcctttg                                                18

<210> SEQ ID NO 313
<211> LENGTH: 18
<212> TYPE: DNA
<213> ORGANISM: Artificial
<220> FEATURE:
<223> OTHER INFORMATION: Synthetic Sequence

<400> SEQUENCE: 313
attgtagggc agctggaa                                                 18

<210> SEQ ID NO 314
<211> LENGTH: 18
<212> TYPE: DNA
<213> ORGANISM: Artificial
<220> FEATURE:
<223> OTHER INFORMATION: Synthetic Sequence

<400> SEQUENCE: 314
gctactggtg atgttgaa                                                 18

<210> SEQ ID NO 315
<211> LENGTH: 18
<212> TYPE: DNA
<213> ORGANISM: Artificial
<220> FEATURE:
<223> OTHER INFORMATION: Synthetic Sequence

<400> SEQUENCE: 315
gacgtcgtag gcgatgtt                                                 18

<210> SEQ ID NO 316
<211> LENGTH: 18
<212> TYPE: DNA
<213> ORGANISM: Artificial
<220> FEATURE:
<223> OTHER INFORMATION: Synthetic Sequence

<400> SEQUENCE: 316
gaaagggttg acgcagca                                                 18

<210> SEQ ID NO 317
<211> LENGTH: 18
<212> TYPE: DNA
<213> ORGANISM: Artificial

```
<220> FEATURE:
<223> OTHER INFORMATION: Synthetic Sequence

<400> SEQUENCE: 317
gaagagatcg ttgcggaa                                                       18

<210> SEQ ID NO 318
<211> LENGTH: 18
<212> TYPE: DNA
<213> ORGANISM: Artificial
<220> FEATURE:
<223> OTHER INFORMATION: Synthetic Sequence

<400> SEQUENCE: 318
gagctgctcc tggctgag                                                       18

<210> SEQ ID NO 319
<211> LENGTH: 18
<212> TYPE: DNA
<213> ORGANISM: Artificial
<220> FEATURE:
<223> OTHER INFORMATION: Synthetic Sequence

<400> SEQUENCE: 319
ctccacactc atggagga                                                       18

<210> SEQ ID NO 320
<211> LENGTH: 20
<212> TYPE: DNA
<213> ORGANISM: Artificial
<220> FEATURE:
<223> OTHER INFORMATION: Synthetic Sequence

<400> SEQUENCE: 320
tctgcaaagc agacttctca                                                     20

<210> SEQ ID NO 321
<211> LENGTH: 20
<212> TYPE: DNA
<213> ORGANISM: Artificial
<220> FEATURE:
<223> OTHER INFORMATION: Synthetic Sequence

<400> SEQUENCE: 321
ttcagcaggt tggcaatctc                                                     20

<210> SEQ ID NO 322
<211> LENGTH: 20
<212> TYPE: DNA
<213> ORGANISM: Artificial
<220> FEATURE:
<223> OTHER INFORMATION: Synthetic Sequence

<400> SEQUENCE: 322
tcggtgagct gccaggatga                                                     20

<210> SEQ ID NO 323
<211> LENGTH: 20
<212> TYPE: DNA
<213> ORGANISM: Artificial
<220> FEATURE:
<223> OTHER INFORMATION: Synthetic Sequence

<400> SEQUENCE: 323
agacatctct tctgggaagc                                                     20
```

```
<210> SEQ ID NO 324
<211> LENGTH: 20
<212> TYPE: DNA
<213> ORGANISM: Artificial
<220> FEATURE:
<223> OTHER INFORMATION: Synthetic Sequence

<400> SEQUENCE: 324
tgaaggcctc ctcagactcc                                                  20

<210> SEQ ID NO 325
<211> LENGTH: 20
<212> TYPE: DNA
<213> ORGANISM: Artificial
<220> FEATURE:
<223> OTHER INFORMATION: Synthetic Sequence

<400> SEQUENCE: 325
acaggttcca ctgagggctt                                                  20

<210> SEQ ID NO 326
<211> LENGTH: 20
<212> TYPE: DNA
<213> ORGANISM: Artificial
<220> FEATURE:
<223> OTHER INFORMATION: Synthetic Sequence

<400> SEQUENCE: 326
atcaaagggc tcggtcttca                                                  20

<210> SEQ ID NO 327
<211> LENGTH: 20
<212> TYPE: DNA
<213> ORGANISM: Artificial
<220> FEATURE:
<223> OTHER INFORMATION: Synthetic Sequence

<400> SEQUENCE: 327
tcagagccac tgggcctgga                                                  20

<210> SEQ ID NO 328
<211> LENGTH: 20
<212> TYPE: DNA
<213> ORGANISM: Artificial
<220> FEATURE:
<223> OTHER INFORMATION: Synthetic Sequence

<400> SEQUENCE: 328
tgctgcatag aaggacccag                                                  20

<210> SEQ ID NO 329
<211> LENGTH: 20
<212> TYPE: DNA
<213> ORGANISM: Artificial
<220> FEATURE:
<223> OTHER INFORMATION: Synthetic Sequence

<400> SEQUENCE: 329
tctgtggcca tgggccccat                                                  20

<210> SEQ ID NO 330
<211> LENGTH: 20
<212> TYPE: DNA
<213> ORGANISM: Artificial
<220> FEATURE:
<223> OTHER INFORMATION: Synthetic Sequence
```

-continued

<400> SEQUENCE: 330
tgtaagcagt gcagctggga                                            20

<210> SEQ ID NO 331
<211> LENGTH: 20
<212> TYPE: DNA
<213> ORGANISM: Artificial
<220> FEATURE:
<223> OTHER INFORMATION: Synthetic Sequence

<400> SEQUENCE: 331
acagctgggg aaggagtcag                                            20

<210> SEQ ID NO 332
<211> LENGTH: 20
<212> TYPE: DNA
<213> ORGANISM: Artificial
<220> FEATURE:
<223> OTHER INFORMATION: Synthetic Sequence

<400> SEQUENCE: 332
agctgagcga gtcagaggaa                                            20

<210> SEQ ID NO 333
<211> LENGTH: 20
<212> TYPE: DNA
<213> ORGANISM: Artificial
<220> FEATURE:
<223> OTHER INFORMATION: Synthetic Sequence

<400> SEQUENCE: 333
tgtaatgcac cagctcgggc                                            20

<210> SEQ ID NO 334
<211> LENGTH: 20
<212> TYPE: DNA
<213> ORGANISM: Artificial
<220> FEATURE:
<223> OTHER INFORMATION: Synthetic Sequence

<400> SEQUENCE: 334
gtctacagga accctctagg                                            20

<210> SEQ ID NO 335
<211> LENGTH: 20
<212> TYPE: DNA
<213> ORGANISM: Artificial
<220> FEATURE:
<223> OTHER INFORMATION: Synthetic Sequence

<400> SEQUENCE: 335
acagcctggt gtgtttcacg                                            20

<210> SEQ ID NO 336
<211> LENGTH: 20
<212> TYPE: DNA
<213> ORGANISM: Artificial
<220> FEATURE:
<223> OTHER INFORMATION: Synthetic Sequence

<400> SEQUENCE: 336
cttgagtcca cacatggatg                                            20

<210> SEQ ID NO 337

```
<211> LENGTH: 20
<212> TYPE: DNA
<213> ORGANISM: Artificial
<220> FEATURE:
<223> OTHER INFORMATION: Synthetic Sequence

<400> SEQUENCE: 337
cactccatgc gttttgctac                                               20

<210> SEQ ID NO 338
<211> LENGTH: 20
<212> TYPE: DNA
<213> ORGANISM: Artificial
<220> FEATURE:
<223> OTHER INFORMATION: Synthetic Sequence

<400> SEQUENCE: 338
ctaactacca gctctctgaa                                               20

<210> SEQ ID NO 339
<211> LENGTH: 20
<212> TYPE: DNA
<213> ORGANISM: Artificial
<220> FEATURE:
<223> OTHER INFORMATION: Synthetic Sequence

<400> SEQUENCE: 339
agagaaaaga gacacagacc                                               20

<210> SEQ ID NO 340
<211> LENGTH: 20
<212> TYPE: DNA
<213> ORGANISM: Artificial
<220> FEATURE:
<223> OTHER INFORMATION: Synthetic Sequence

<400> SEQUENCE: 340
cccaatagat tagttaatgc                                               20

<210> SEQ ID NO 341
<211> LENGTH: 20
<212> TYPE: DNA
<213> ORGANISM: Artificial
<220> FEATURE:
<223> OTHER INFORMATION: Synthetic Sequence

<400> SEQUENCE: 341
caatttgaaa atatccagca                                               20

<210> SEQ ID NO 342
<211> LENGTH: 20
<212> TYPE: DNA
<213> ORGANISM: Artificial
<220> FEATURE:
<223> OTHER INFORMATION: Synthetic Sequence

<400> SEQUENCE: 342
ccaggaacac agtagttatt                                               20

<210> SEQ ID NO 343
<211> LENGTH: 20
<212> TYPE: DNA
<213> ORGANISM: Artificial
<220> FEATURE:
<223> OTHER INFORMATION: Synthetic Sequence

<400> SEQUENCE: 343
```
cttagtataa tattggtcat		20

<210> SEQ ID NO 344
<211> LENGTH: 20
<212> TYPE: DNA
<213> ORGANISM: Artificial
<220> FEATURE:
<223> OTHER INFORMATION: Synthetic Sequence

<400> SEQUENCE: 344
tctgcaaagc agacttctca		20

<210> SEQ ID NO 345
<211> LENGTH: 20
<212> TYPE: DNA
<213> ORGANISM: Artificial
<220> FEATURE:
<223> OTHER INFORMATION: Synthetic Sequence

<400> SEQUENCE: 345
actctagttt ttccttctcc		20

<210> SEQ ID NO 346
<211> LENGTH: 20
<212> TYPE: DNA
<213> ORGANISM: Artificial
<220> FEATURE:
<223> OTHER INFORMATION: Synthetic Sequence

<400> SEQUENCE: 346
aggtcatcag ggatcttgca		20

<210> SEQ ID NO 347
<211> LENGTH: 20
<212> TYPE: DNA
<213> ORGANISM: Artificial
<220> FEATURE:
<223> OTHER INFORMATION: Synthetic Sequence

<400> SEQUENCE: 347
agtcagatca agggaagcca		20

<210> SEQ ID NO 348
<211> LENGTH: 20
<212> TYPE: DNA
<213> ORGANISM: Artificial
<220> FEATURE:
<223> OTHER INFORMATION: Synthetic Sequence

<400> SEQUENCE: 348
agggtcattg aggagaggca		20

<210> SEQ ID NO 349
<211> LENGTH: 20
<212> TYPE: DNA
<213> ORGANISM: Artificial
<220> FEATURE:
<223> OTHER INFORMATION: Synthetic Sequence

<400> SEQUENCE: 349
tccatgctgc tgatgctctt		20

<210> SEQ ID NO 350
<211> LENGTH: 20
<212> TYPE: DNA

-continued

```
<213> ORGANISM: Artificial
<220> FEATURE:
<223> OTHER INFORMATION: Synthetic Sequence

<400> SEQUENCE: 350
tgatgctggg aacaggaagt                                                   20

<210> SEQ ID NO 351
<211> LENGTH: 20
<212> TYPE: DNA
<213> ORGANISM: Artificial
<220> FEATURE:
<223> OTHER INFORMATION: Synthetic Sequence

<400> SEQUENCE: 351
tcagagccac tgggcctgga                                                   20

<210> SEQ ID NO 352
<211> LENGTH: 20
<212> TYPE: DNA
<213> ORGANISM: Artificial
<220> FEATURE:
<223> OTHER INFORMATION: Synthetic Sequence

<400> SEQUENCE: 352
actgtgcaga ggctcccagt                                                   20

<210> SEQ ID NO 353
<211> LENGTH: 20
<212> TYPE: DNA
<213> ORGANISM: Artificial
<220> FEATURE:
<223> OTHER INFORMATION: Synthetic Sequence

<400> SEQUENCE: 353
tacaggtgac caccggagtg                                                   20

<210> SEQ ID NO 354
<211> LENGTH: 20
<212> TYPE: DNA
<213> ORGANISM: Artificial
<220> FEATURE:
<223> OTHER INFORMATION: Synthetic Sequence

<400> SEQUENCE: 354
taggtgaaga cgaaggaaga                                                   20

<210> SEQ ID NO 355
<211> LENGTH: 20
<212> TYPE: DNA
<213> ORGANISM: Artificial
<220> FEATURE:
<223> OTHER INFORMATION: Synthetic Sequence

<400> SEQUENCE: 355
tcattgctgc tgctgccctt                                                   20

<210> SEQ ID NO 356
<211> LENGTH: 20
<212> TYPE: DNA
<213> ORGANISM: Artificial
<220> FEATURE:
<223> OTHER INFORMATION: Synthetic Sequence

<400> SEQUENCE: 356
agtggcactt gtgggtgccg                                                   20
```

<210> SEQ ID NO 357
<211> LENGTH: 20
<212> TYPE: DNA
<213> ORGANISM: Artificial
<220> FEATURE:
<223> OTHER INFORMATION: Synthetic Sequence

<400> SEQUENCE: 357
gaagatgtgt ttctcctctc                                               20

<210> SEQ ID NO 358
<211> LENGTH: 20
<212> TYPE: DNA
<213> ORGANISM: Artificial
<220> FEATURE:
<223> OTHER INFORMATION: Synthetic Sequence

<400> SEQUENCE: 358
acagataagg tcctccctag                                               20

<210> SEQ ID NO 359
<211> LENGTH: 20
<212> TYPE: DNA
<213> ORGANISM: Artificial
<220> FEATURE:
<223> OTHER INFORMATION: Synthetic Sequence

<400> SEQUENCE: 359
ctttcaagtc cttgaggccc                                               20

<210> SEQ ID NO 360
<211> LENGTH: 20
<212> TYPE: DNA
<213> ORGANISM: Artificial
<220> FEATURE:
<223> OTHER INFORMATION: Synthetic Sequence

<400> SEQUENCE: 360
atctccggaa gaggtaagga                                               20

<210> SEQ ID NO 361
<211> LENGTH: 20
<212> TYPE: DNA
<213> ORGANISM: Artificial
<220> FEATURE:
<223> OTHER INFORMATION: Synthetic Sequence

<400> SEQUENCE: 361
gtgtcactgg gaacaataca                                               20

<210> SEQ ID NO 362
<211> LENGTH: 20
<212> TYPE: DNA
<213> ORGANISM: Artificial
<220> FEATURE:
<223> OTHER INFORMATION: Synthetic Sequence

<400> SEQUENCE: 362
aggcctggct caacatgcta                                               20

<210> SEQ ID NO 363
<211> LENGTH: 19
<212> TYPE: DNA
<213> ORGANISM: Artificial
<220> FEATURE:

<223> OTHER INFORMATION: Synthetic Sequence

<400> SEQUENCE: 363
tatgagaaga ctaaggaga                                                    19

<210> SEQ ID NO 364
<211> LENGTH: 20
<212> TYPE: DNA
<213> ORGANISM: Artificial
<220> FEATURE:
<223> OTHER INFORMATION: Synthetic Sequence

<400> SEQUENCE: 364
ccaggttaat tccaataatg                                                   20

<210> SEQ ID NO 365
<211> LENGTH: 20
<212> TYPE: DNA
<213> ORGANISM: Artificial
<220> FEATURE:
<223> OTHER INFORMATION: Synthetic Sequence

<400> SEQUENCE: 365
gttaaaatca gctgcactag                                                   20

<210> SEQ ID NO 366
<211> LENGTH: 20
<212> TYPE: DNA
<213> ORGANISM: Artificial
<220> FEATURE:
<223> OTHER INFORMATION: Synthetic Sequence

<400> SEQUENCE: 366
ctaatcagaa cacactattg                                                   20

<210> SEQ ID NO 367
<211> LENGTH: 20
<212> TYPE: DNA
<213> ORGANISM: Artificial
<220> FEATURE:
<223> OTHER INFORMATION: Synthetic Sequence

<400> SEQUENCE: 367
ccagaaaata aagtcgtatc                                                   20

<210> SEQ ID NO 368
<211> LENGTH: 17
<212> TYPE: DNA
<213> ORGANISM: Artificial
<220> FEATURE:
<223> OTHER INFORMATION: Synthetic Sequence

<400> SEQUENCE: 368
tcgcccttgc tcaccat                                                      17

<210> SEQ ID NO 369
<211> LENGTH: 17
<212> TYPE: DNA
<213> ORGANISM: Artificial
<220> FEATURE:
<223> OTHER INFORMATION: Synthetic Sequence

<400> SEQUENCE: 369
tcgaccagga tgggcac                                                      17

```
<210> SEQ ID NO 370
<211> LENGTH: 17
<212> TYPE: DNA
<213> ORGANISM: Artificial
<220> FEATURE:
<223> OTHER INFORMATION: Synthetic Sequence

<400> SEQUENCE: 370
gctgaacttg tggccgt                                                  17

<210> SEQ ID NO 371
<211> LENGTH: 17
<212> TYPE: DNA
<213> ORGANISM: Artificial
<220> FEATURE:
<223> OTHER INFORMATION: Synthetic Sequence

<400> SEQUENCE: 371
cgtaggtggc atcgccc                                                  17

<210> SEQ ID NO 372
<211> LENGTH: 17
<212> TYPE: DNA
<213> ORGANISM: Artificial
<220> FEATURE:
<223> OTHER INFORMATION: Synthetic Sequence

<400> SEQUENCE: 372
ccggtggtgc agatgaa                                                  17

<210> SEQ ID NO 373
<211> LENGTH: 17
<212> TYPE: DNA
<213> ORGANISM: Artificial
<220> FEATURE:
<223> OTHER INFORMATION: Synthetic Sequence

<400> SEQUENCE: 373
agggtggtca cgagggt                                                  17

<210> SEQ ID NO 374
<211> LENGTH: 17
<212> TYPE: DNA
<213> ORGANISM: Artificial
<220> FEATURE:
<223> OTHER INFORMATION: Synthetic Sequence

<400> SEQUENCE: 374
tcggggtagc ggctgaa                                                  17

<210> SEQ ID NO 375
<211> LENGTH: 17
<212> TYPE: DNA
<213> ORGANISM: Artificial
<220> FEATURE:
<223> OTHER INFORMATION: Synthetic Sequence

<400> SEQUENCE: 375
ggcggacttg aagaagt                                                  17

<210> SEQ ID NO 376
<211> LENGTH: 17
<212> TYPE: DNA
<213> ORGANISM: Artificial
<220> FEATURE:
<223> OTHER INFORMATION: Synthetic Sequence
```

```
<400> SEQUENCE: 376
agatggtgcg ctcctgg                                                    17

<210> SEQ ID NO 377
<211> LENGTH: 17
<212> TYPE: DNA
<213> ORGANISM: Artificial
<220> FEATURE:
<223> OTHER INFORMATION: Synthetic Sequence

<400> SEQUENCE: 377
gcgcgggtct tgtagtt                                                    17

<210> SEQ ID NO 378
<211> LENGTH: 17
<212> TYPE: DNA
<213> ORGANISM: Artificial
<220> FEATURE:
<223> OTHER INFORMATION: Synthetic Sequence

<400> SEQUENCE: 378
gttcaccagg gtgtcgc                                                    17

<210> SEQ ID NO 379
<211> LENGTH: 17
<212> TYPE: DNA
<213> ORGANISM: Artificial
<220> FEATURE:
<223> OTHER INFORMATION: Synthetic Sequence

<400> SEQUENCE: 379
cctccttgaa gtcgatg                                                    17

<210> SEQ ID NO 380
<211> LENGTH: 17
<212> TYPE: DNA
<213> ORGANISM: Artificial
<220> FEATURE:
<223> OTHER INFORMATION: Synthetic Sequence

<400> SEQUENCE: 380
ttgtactcca gcttgtg                                                    17

<210> SEQ ID NO 381
<211> LENGTH: 17
<212> TYPE: DNA
<213> ORGANISM: Artificial
<220> FEATURE:
<223> OTHER INFORMATION: Synthetic Sequence

<400> SEQUENCE: 381
gtcggccatg atataga                                                    17

<210> SEQ ID NO 382
<211> LENGTH: 17
<212> TYPE: DNA
<213> ORGANISM: Artificial
<220> FEATURE:
<223> OTHER INFORMATION: Synthetic Sequence

<400> SEQUENCE: 382
tcttgaagtt caccttg                                                    17

<210> SEQ ID NO 383
<211> LENGTH: 17
```

```
<212> TYPE: DNA
<213> ORGANISM: Artificial
<220> FEATURE:
<223> OTHER INFORMATION: Synthetic Sequence

<400> SEQUENCE: 383
agctgcacgc tgccgtc                                                17

<210> SEQ ID NO 384
<211> LENGTH: 17
<212> TYPE: DNA
<213> ORGANISM: Artificial
<220> FEATURE:
<223> OTHER INFORMATION: Synthetic Sequence

<400> SEQUENCE: 384
tcgccgatgg gggtgtt                                                17

<210> SEQ ID NO 385
<211> LENGTH: 17
<212> TYPE: DNA
<213> ORGANISM: Artificial
<220> FEATURE:
<223> OTHER INFORMATION: Synthetic Sequence

<400> SEQUENCE: 385
gggtgctcag gtagtgg                                                17

<210> SEQ ID NO 386
<211> LENGTH: 17
<212> TYPE: DNA
<213> ORGANISM: Artificial
<220> FEATURE:
<223> OTHER INFORMATION: Synthetic Sequence

<400> SEQUENCE: 386
cgcttctcgt tggggtc                                                17

<210> SEQ ID NO 387
<211> LENGTH: 17
<212> TYPE: DNA
<213> ORGANISM: Artificial
<220> FEATURE:
<223> OTHER INFORMATION: Synthetic Sequence

<400> SEQUENCE: 387
ggcggtcacg aactcca                                                17

<210> SEQ ID NO 388
<211> LENGTH: 17
<212> TYPE: DNA
<213> ORGANISM: Artificial
<220> FEATURE:
<223> OTHER INFORMATION: Synthetic Sequence

<400> SEQUENCE: 388
tcttgtacag ctcgtcc                                                17

<210> SEQ ID NO 389
<211> LENGTH: 17
<212> TYPE: DNA
<213> ORGANISM: Artificial
<220> FEATURE:
<223> OTHER INFORMATION: Synthetic Sequence

<400> SEQUENCE: 389
```
tcctgctcct ccacctc                                                        17

<210> SEQ ID NO 390
<211> LENGTH: 17
<212> TYPE: DNA
<213> ORGANISM: Artificial
<220> FEATURE:
<223> OTHER INFORMATION: Synthetic Sequence

<400> SEQUENCE: 390
ctcctgggca caagaca                                                        17

<210> SEQ ID NO 391
<211> LENGTH: 17
<212> TYPE: DNA
<213> ORGANISM: Artificial
<220> FEATURE:
<223> OTHER INFORMATION: Synthetic Sequence

<400> SEQUENCE: 391
agaagcacag gctgcag                                                        17

<210> SEQ ID NO 392
<211> LENGTH: 17
<212> TYPE: DNA
<213> ORGANISM: Artificial
<220> FEATURE:
<223> OTHER INFORMATION: Synthetic Sequence

<400> SEQUENCE: 392
accccggtga acagctc                                                        17

<210> SEQ ID NO 393
<211> LENGTH: 17
<212> TYPE: DNA
<213> ORGANISM: Artificial
<220> FEATURE:
<223> OTHER INFORMATION: Synthetic Sequence

<400> SEQUENCE: 393
ttacgtcgcc gtccagc                                                        17

<210> SEQ ID NO 394
<211> LENGTH: 17
<212> TYPE: DNA
<213> ORGANISM: Artificial
<220> FEATURE:
<223> OTHER INFORMATION: Synthetic Sequence

<400> SEQUENCE: 394
tcgccctcgc cggacac                                                        17

<210> SEQ ID NO 395
<211> LENGTH: 17
<212> TYPE: DNA
<213> ORGANISM: Artificial
<220> FEATURE:
<223> OTHER INFORMATION: Synthetic Sequence

<400> SEQUENCE: 395
cttcagggtc agcttgc                                                        17

<210> SEQ ID NO 396
<211> LENGTH: 17
<212> TYPE: DNA
<213> ORGANISM: Artificial

```
<220> FEATURE:
<223> OTHER INFORMATION: Synthetic Sequence

<400> SEQUENCE: 396
agggcacggg cagcttg                                                  17

<210> SEQ ID NO 397
<211> LENGTH: 17
<212> TYPE: DNA
<213> ORGANISM: Artificial
<220> FEATURE:
<223> OTHER INFORMATION: Synthetic Sequence

<400> SEQUENCE: 397
actgcacgcc gtaggtc                                                  17

<210> SEQ ID NO 398
<211> LENGTH: 17
<212> TYPE: DNA
<213> ORGANISM: Artificial
<220> FEATURE:
<223> OTHER INFORMATION: Synthetic Sequence

<400> SEQUENCE: 398
cgtgctgctt catgtgg                                                  17

<210> SEQ ID NO 399
<211> LENGTH: 17
<212> TYPE: DNA
<213> ORGANISM: Artificial
<220> FEATURE:
<223> OTHER INFORMATION: Synthetic Sequence

<400> SEQUENCE: 399
acgtagcctt cgggcat                                                  17

<210> SEQ ID NO 400
<211> LENGTH: 17
<212> TYPE: DNA
<213> ORGANISM: Artificial
<220> FEATURE:
<223> OTHER INFORMATION: Synthetic Sequence

<400> SEQUENCE: 400
gccgtcgtcc ttgaaga                                                  17

<210> SEQ ID NO 401
<211> LENGTH: 17
<212> TYPE: DNA
<213> ORGANISM: Artificial
<220> FEATURE:
<223> OTHER INFORMATION: Synthetic Sequence

<400> SEQUENCE: 401
cctcgaactt cacctcg                                                  17

<210> SEQ ID NO 402
<211> LENGTH: 17
<212> TYPE: DNA
<213> ORGANISM: Artificial
<220> FEATURE:
<223> OTHER INFORMATION: Synthetic Sequence

<400> SEQUENCE: 402
cccttcagct cgatgcg                                                  17
```

<210> SEQ ID NO 403
<211> LENGTH: 17
<212> TYPE: DNA
<213> ORGANISM: Artificial
<220> FEATURE:
<223> OTHER INFORMATION: Synthetic Sequence

<400> SEQUENCE: 403
ccccaggatg ttgccgt                                                    17

<210> SEQ ID NO 404
<211> LENGTH: 17
<212> TYPE: DNA
<213> ORGANISM: Artificial
<220> FEATURE:
<223> OTHER INFORMATION: Synthetic Sequence

<400> SEQUENCE: 404
cgttgtggct gttgtag                                                    17

<210> SEQ ID NO 405
<211> LENGTH: 17
<212> TYPE: DNA
<213> ORGANISM: Artificial
<220> FEATURE:
<223> OTHER INFORMATION: Synthetic Sequence

<400> SEQUENCE: 405
atgccgttct tctgctt                                                    17

<210> SEQ ID NO 406
<211> LENGTH: 17
<212> TYPE: DNA
<213> ORGANISM: Artificial
<220> FEATURE:
<223> OTHER INFORMATION: Synthetic Sequence

<400> SEQUENCE: 406
ctcgatgttg tggcgga                                                    17

<210> SEQ ID NO 407
<211> LENGTH: 17
<212> TYPE: DNA
<213> ORGANISM: Artificial
<220> FEATURE:
<223> OTHER INFORMATION: Synthetic Sequence

<400> SEQUENCE: 407
tgctggtagt ggtcggc                                                    17

<210> SEQ ID NO 408
<211> LENGTH: 17
<212> TYPE: DNA
<213> ORGANISM: Artificial
<220> FEATURE:
<223> OTHER INFORMATION: Synthetic Sequence

<400> SEQUENCE: 408
ttgtcgggca gcagcac                                                    17

<210> SEQ ID NO 409
<211> LENGTH: 17
<212> TYPE: DNA
<213> ORGANISM: Artificial
<220> FEATURE:
<223> OTHER INFORMATION: Synthetic Sequence

<400> SEQUENCE: 409
tttgctcagg gcggact                                                        17

<210> SEQ ID NO 410
<211> LENGTH: 17
<212> TYPE: DNA
<213> ORGANISM: Artificial
<220> FEATURE:
<223> OTHER INFORMATION: Synthetic Sequence

<400> SEQUENCE: 410
gcaggaccat gtgatcg                                                        17

<210> SEQ ID NO 411
<211> LENGTH: 17
<212> TYPE: DNA
<213> ORGANISM: Artificial
<220> FEATURE:
<223> OTHER INFORMATION: Synthetic Sequence

<400> SEQUENCE: 411
atgccgagag tgatccc                                                        17

<210> SEQ ID NO 412
<211> LENGTH: 17
<212> TYPE: DNA
<213> ORGANISM: Artificial
<220> FEATURE:
<223> OTHER INFORMATION: Synthetic Sequence

<400> SEQUENCE: 412
gaagccatgg ctaagct                                                        17

<210> SEQ ID NO 413
<211> LENGTH: 17
<212> TYPE: DNA
<213> ORGANISM: Artificial
<220> FEATURE:
<223> OTHER INFORMATION: Synthetic Sequence

<400> SEQUENCE: 413
tgggcagcgt gccatca                                                        17

<210> SEQ ID NO 414
<211> LENGTH: 17
<212> TYPE: DNA
<213> ORGANISM: Artificial
<220> FEATURE:
<223> OTHER INFORMATION: Synthetic Sequence

<400> SEQUENCE: 414
tgacggtcca tcccgct                                                        17

<210> SEQ ID NO 415
<211> LENGTH: 17
<212> TYPE: DNA
<213> ORGANISM: Artificial
<220> FEATURE:
<223> OTHER INFORMATION: Synthetic Sequence

<400> SEQUENCE: 415
tacacattga tcctagc                                                        17

<210> SEQ ID NO 416

```
<211> LENGTH: 20
<212> TYPE: DNA
<213> ORGANISM: Artificial
<220> FEATURE:
<223> OTHER INFORMATION: Synthetic Sequence

<400> SEQUENCE: 416
ttaatactga cgctctcgca                                               20

<210> SEQ ID NO 417
<211> LENGTH: 20
<212> TYPE: DNA
<213> ORGANISM: Artificial
<220> FEATURE:
<223> OTHER INFORMATION: Synthetic Sequence

<400> SEQUENCE: 417
ccctggtctt aaccgaattt                                               20

<210> SEQ ID NO 418
<211> LENGTH: 20
<212> TYPE: DNA
<213> ORGANISM: Artificial
<220> FEATURE:
<223> OTHER INFORMATION: Synthetic Sequence

<400> SEQUENCE: 418
aactgcgaat cgttctagct                                               20

<210> SEQ ID NO 419
<211> LENGTH: 20
<212> TYPE: DNA
<213> ORGANISM: Artificial
<220> FEATURE:
<223> OTHER INFORMATION: Synthetic Sequence

<400> SEQUENCE: 419
ccagtatttg tctacagcct                                               20

<210> SEQ ID NO 420
<211> LENGTH: 20
<212> TYPE: DNA
<213> ORGANISM: Artificial
<220> FEATURE:
<223> OTHER INFORMATION: Synthetic Sequence

<400> SEQUENCE: 420
gagggtggct actgtattat                                               20

<210> SEQ ID NO 421
<211> LENGTH: 20
<212> TYPE: DNA
<213> ORGANISM: Artificial
<220> FEATURE:
<223> OTHER INFORMATION: Synthetic Sequence

<400> SEQUENCE: 421
gcttccttgg tgtcttttac                                               20

<210> SEQ ID NO 422
<211> LENGTH: 20
<212> TYPE: DNA
<213> ORGANISM: Artificial
<220> FEATURE:
<223> OTHER INFORMATION: Synthetic Sequence

<400> SEQUENCE: 422
```
gctgtgcctt tttcttactt                                            20

<210> SEQ ID NO 423
<211> LENGTH: 20
<212> TYPE: DNA
<213> ORGANISM: Artificial
<220> FEATURE:
<223> OTHER INFORMATION: Synthetic Sequence

<400> SEQUENCE: 423
gtaattttgg ctgacctggt                                            20

<210> SEQ ID NO 424
<211> LENGTH: 20
<212> TYPE: DNA
<213> ORGANISM: Artificial
<220> FEATURE:
<223> OTHER INFORMATION: Synthetic Sequence

<400> SEQUENCE: 424
atggcctgat gtaccatttg                                            20

<210> SEQ ID NO 425
<211> LENGTH: 20
<212> TYPE: DNA
<213> ORGANISM: Artificial
<220> FEATURE:
<223> OTHER INFORMATION: Synthetic Sequence

<400> SEQUENCE: 425
gctccttctg ataatgctga                                            20

<210> SEQ ID NO 426
<211> LENGTH: 20
<212> TYPE: DNA
<213> ORGANISM: Artificial
<220> FEATURE:
<223> OTHER INFORMATION: Synthetic Sequence

<400> SEQUENCE: 426
tttgcatggc tgcttgatgt                                            20

<210> SEQ ID NO 427
<211> LENGTH: 20
<212> TYPE: DNA
<213> ORGANISM: Artificial
<220> FEATURE:
<223> OTHER INFORMATION: Synthetic Sequence

<400> SEQUENCE: 427
tgcaatctat cccattctgc                                            20

<210> SEQ ID NO 428
<211> LENGTH: 20
<212> TYPE: DNA
<213> ORGANISM: Artificial
<220> FEATURE:
<223> OTHER INFORMATION: Synthetic Sequence

<400> SEQUENCE: 428
tatgtcactt cccctggtt                                             20

<210> SEQ ID NO 429
<211> LENGTH: 20
<212> TYPE: DNA

```
<213> ORGANISM: Artificial
<220> FEATURE:
<223> OTHER INFORMATION: Synthetic Sequence

<400> SEQUENCE: 429
gtcatccatc ctatttgttc                                               20

<210> SEQ ID NO 430
<211> LENGTH: 20
<212> TYPE: DNA
<213> ORGANISM: Artificial
<220> FEATURE:
<223> OTHER INFORMATION: Synthetic Sequence

<400> SEQUENCE: 430
cccaggatta tccatctttt                                               20

<210> SEQ ID NO 431
<211> LENGTH: 20
<212> TYPE: DNA
<213> ORGANISM: Artificial
<220> FEATURE:
<223> OTHER INFORMATION: Synthetic Sequence

<400> SEQUENCE: 431
gtccttgtct tatgtccaga                                               20

<210> SEQ ID NO 432
<211> LENGTH: 20
<212> TYPE: DNA
<213> ORGANISM: Artificial
<220> FEATURE:
<223> OTHER INFORMATION: Synthetic Sequence

<400> SEQUENCE: 432
agagttttat agaaccggtc                                               20

<210> SEQ ID NO 433
<211> LENGTH: 20
<212> TYPE: DNA
<213> ORGANISM: Artificial
<220> FEATURE:
<223> OTHER INFORMATION: Synthetic Sequence

<400> SEQUENCE: 433
caacaaggtt tctgtcatcc                                               20

<210> SEQ ID NO 434
<211> LENGTH: 20
<212> TYPE: DNA
<213> ORGANISM: Artificial
<220> FEATURE:
<223> OTHER INFORMATION: Synthetic Sequence

<400> SEQUENCE: 434
gctggtccca atgcttttaa                                               20

<210> SEQ ID NO 435
<211> LENGTH: 20
<212> TYPE: DNA
<213> ORGANISM: Artificial
<220> FEATURE:
<223> OTHER INFORMATION: Synthetic Sequence

<400> SEQUENCE: 435
aaactcttgc tttatggccg                                               20
```

<210> SEQ ID NO 436
<211> LENGTH: 20
<212> TYPE: DNA
<213> ORGANISM: Artificial
<220> FEATURE:
<223> OTHER INFORMATION: Synthetic Sequence

<400> SEQUENCE: 436
ctgcatcatt atggtagctg                                           20

<210> SEQ ID NO 437
<211> LENGTH: 20
<212> TYPE: DNA
<213> ORGANISM: Artificial
<220> FEATURE:
<223> OTHER INFORMATION: Synthetic Sequence

<400> SEQUENCE: 437
ggctctgcaa ttttggcta                                            20

<210> SEQ ID NO 438
<211> LENGTH: 20
<212> TYPE: DNA
<213> ORGANISM: Artificial
<220> FEATURE:
<223> OTHER INFORMATION: Synthetic Sequence

<400> SEQUENCE: 438
tttggtgtcc ttcctttcca                                           20

<210> SEQ ID NO 439
<211> LENGTH: 20
<212> TYPE: DNA
<213> ORGANISM: Artificial
<220> FEATURE:
<223> OTHER INFORMATION: Synthetic Sequence

<400> SEQUENCE: 439
gggccagatt ttccctaaaa                                           20

<210> SEQ ID NO 440
<211> LENGTH: 20
<212> TYPE: DNA
<213> ORGANISM: Artificial
<220> FEATURE:
<223> OTHER INFORMATION: Synthetic Sequence

<400> SEQUENCE: 440
catttatcta actctccccc                                           20

<210> SEQ ID NO 441
<211> LENGTH: 20
<212> TYPE: DNA
<213> ORGANISM: Artificial
<220> FEATURE:
<223> OTHER INFORMATION: Synthetic Sequence

<400> SEQUENCE: 441
ctgcttgccc atactatatg                                           20

<210> SEQ ID NO 442
<211> LENGTH: 20
<212> TYPE: DNA
<213> ORGANISM: Artificial
<220> FEATURE:

```
<223> OTHER INFORMATION: Synthetic Sequence

<400> SEQUENCE: 442
atgtttctaa caggccagga                                          20

<210> SEQ ID NO 443
<211> LENGTH: 20
<212> TYPE: DNA
<213> ORGANISM: Artificial
<220> FEATURE:
<223> OTHER INFORMATION: Synthetic Sequence

<400> SEQUENCE: 443
tgtctgaagg gatggttgta                                          20

<210> SEQ ID NO 444
<211> LENGTH: 20
<212> TYPE: DNA
<213> ORGANISM: Artificial
<220> FEATURE:
<223> OTHER INFORMATION: Synthetic Sequence

<400> SEQUENCE: 444
ctatcctttg atgcacacaa                                          20

<210> SEQ ID NO 445
<211> LENGTH: 20
<212> TYPE: DNA
<213> ORGANISM: Artificial
<220> FEATURE:
<223> OTHER INFORMATION: Synthetic Sequence

<400> SEQUENCE: 445
gctcttcctc tatcttctct                                          20

<210> SEQ ID NO 446
<211> LENGTH: 20
<212> TYPE: DNA
<213> ORGANISM: Artificial
<220> FEATURE:
<223> OTHER INFORMATION: Synthetic Sequence

<400> SEQUENCE: 446
tttttcctgt gtcagctgct                                          20

<210> SEQ ID NO 447
<211> LENGTH: 20
<212> TYPE: DNA
<213> ORGANISM: Artificial
<220> FEATURE:
<223> OTHER INFORMATION: Synthetic Sequence

<400> SEQUENCE: 447
cctggatgtt ctgcactata                                          20

<210> SEQ ID NO 448
<211> LENGTH: 20
<212> TYPE: DNA
<213> ORGANISM: Artificial
<220> FEATURE:
<223> OTHER INFORMATION: Synthetic Sequence

<400> SEQUENCE: 448
ctgaaagcct tctcttctac                                          20
```

```
<210> SEQ ID NO 449
<211> LENGTH: 20
<212> TYPE: DNA
<213> ORGANISM: Artificial
<220> FEATURE:
<223> OTHER INFORMATION: Synthetic Sequence

<400> SEQUENCE: 449
ggtgtttaaa tcttgtgggg                                              20

<210> SEQ ID NO 450
<211> LENGTH: 20
<212> TYPE: DNA
<213> ORGANISM: Artificial
<220> FEATURE:
<223> OTHER INFORMATION: Synthetic Sequence

<400> SEQUENCE: 450
cttcctcatt gatggtctct                                              20

<210> SEQ ID NO 451
<211> LENGTH: 20
<212> TYPE: DNA
<213> ORGANISM: Artificial
<220> FEATURE:
<223> OTHER INFORMATION: Synthetic Sequence

<400> SEQUENCE: 451
tcatctggcc tggtgcaata                                              20

<210> SEQ ID NO 452
<211> LENGTH: 20
<212> TYPE: DNA
<213> ORGANISM: Artificial
<220> FEATURE:
<223> OTHER INFORMATION: Synthetic Sequence

<400> SEQUENCE: 452
gaagggtact agtagttcct                                              20

<210> SEQ ID NO 453
<211> LENGTH: 20
<212> TYPE: DNA
<213> ORGANISM: Artificial
<220> FEATURE:
<223> OTHER INFORMATION: Synthetic Sequence

<400> SEQUENCE: 453
ctactgggat aggtggatta                                              20

<210> SEQ ID NO 454
<211> LENGTH: 20
<212> TYPE: DNA
<213> ORGANISM: Artificial
<220> FEATURE:
<223> OTHER INFORMATION: Synthetic Sequence

<400> SEQUENCE: 454
gtagggctat acatccttac                                              20

<210> SEQ ID NO 455
<211> LENGTH: 20
<212> TYPE: DNA
<213> ORGANISM: Artificial
<220> FEATURE:
<223> OTHER INFORMATION: Synthetic Sequence
```

<400> SEQUENCE: 455
catagtctct aaagggttcc                                                    20

<210> SEQ ID NO 456
<211> LENGTH: 20
<212> TYPE: DNA
<213> ORGANISM: Artificial
<220> FEATURE:
<223> OTHER INFORMATION: Synthetic Sequence

<400> SEQUENCE: 456
tttacctcct gtgaagcttg                                                    20

<210> SEQ ID NO 457
<211> LENGTH: 20
<212> TYPE: DNA
<213> ORGANISM: Artificial
<220> FEATURE:
<223> OTHER INFORMATION: Synthetic Sequence

<400> SEQUENCE: 457
aatctgggtt cgcattttgg                                                    20

<210> SEQ ID NO 458
<211> LENGTH: 20
<212> TYPE: DNA
<213> ORGANISM: Artificial
<220> FEATURE:
<223> OTHER INFORMATION: Synthetic Sequence

<400> SEQUENCE: 458
ggcatgctgt catcatttct                                                    20

<210> SEQ ID NO 459
<211> LENGTH: 20
<212> TYPE: DNA
<213> ORGANISM: Artificial
<220> FEATURE:
<223> OTHER INFORMATION: Synthetic Sequence

<400> SEQUENCE: 459
tacttggctc attgcttcag                                                    20

<210> SEQ ID NO 460
<211> LENGTH: 20
<212> TYPE: DNA
<213> ORGANISM: Artificial
<220> FEATURE:
<223> OTHER INFORMATION: Synthetic Sequence

<400> SEQUENCE: 460
cccttctttg ccacaattga                                                    20

<210> SEQ ID NO 461
<211> LENGTH: 20
<212> TYPE: DNA
<213> ORGANISM: Artificial
<220> FEATURE:
<223> OTHER INFORMATION: Synthetic Sequence

<400> SEQUENCE: 461
tccaacagcc cttttttccta                                                   20

<210> SEQ ID NO 462
<211> LENGTH: 20

```
<212> TYPE: DNA
<213> ORGANISM: Artificial
<220> FEATURE:
<223> OTHER INFORMATION: Synthetic Sequence

<400> SEQUENCE: 462
cctgtctctc agtacaatct                                              20

<210> SEQ ID NO 463
<211> LENGTH: 20
<212> TYPE: DNA
<213> ORGANISM: Artificial
<220> FEATURE:
<223> OTHER INFORMATION: Synthetic Sequence

<400> SEQUENCE: 463
aagaaaattc cctggccttc                                              20
```